(12) United States Patent
Tung et al.

(10) Patent No.: US 8,314,141 B2
(45) Date of Patent: *Nov. 20, 2012

(54) INHIBITORS OF SERINE PROTEASES, PARTICULARLY HEPATITIS C VIRUS NS3 PROTEASE

(75) Inventors: Roger D. Tung, Arlington, MA (US); Scott L. Harbeson, Cambridge, MA (US); David D. Deininger, Arlington, MA (US); Mark A. Murcko, Holliston, MA (US); Govinda R. Bhisetti, Lexington, MA (US); Luc J. Farmer, Foxboro, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 407 days.

This patent is subject to a terminal disclaimer.

(21) Appl. No.: 12/031,486

(22) Filed: Feb. 14, 2008

(65) Prior Publication Data
US 2009/0143312 A1 Jun. 4, 2009

Related U.S. Application Data

(60) Continuation of application No. 10/607,716, filed on Jun. 27, 2003, now Pat. No. 7,388,017, which is a division of application No. 09/875,390, filed on Jun. 6, 2001, now Pat. No. 6,617,309, which is a division of application No. 09/293,247, filed on Apr. 16, 1999, now Pat. No. 6,265,380, which is a continuation of application No. PCT/US97/18968, filed on Oct. 17, 1997.

(60) Provisional application No. 60/028,290, filed on Oct. 18, 1996.

(51) Int. Cl.
*A61K 31/40* (2006.01)
(52) U.S. Cl. ........................ 514/423; 548/538
(58) Field of Classification Search .................. 514/423; 548/538
See application file for complete search history.

(56) References Cited

U.S. PATENT DOCUMENTS

| | | | |
|---|---|---|---|
| 4,499,082 A | 2/1985 | Shenvi et al. | |
| 4,720,484 A | 1/1988 | Vincent et al. | |
| 4,880,780 A | 11/1989 | Trainor et al. | |
| 5,053,519 A | 10/1991 | Teetz et al. | |
| 5,231,084 A | 7/1993 | Hock et al. | |
| 5,371,072 A | 12/1994 | Webb et al. | |
| 5,384,410 A | 1/1995 | Kettner | |
| 5,468,858 A | 11/1995 | Berlin et al. | |
| 5,484,801 A | 1/1996 | Al-Razzak et al. | |
| 5,496,927 A | 3/1996 | Kolb et al. | |
| 5,502,061 A | 3/1996 | Hui et al. | |
| 5,559,158 A | 9/1996 | Al-Razzak et al. | |
| 5,610,193 A | 3/1997 | Al-Razzak et al. | |
| 5,656,600 A | 8/1997 | Abelman et al. | |
| 5,656,627 A | 8/1997 | Bemis et al. | |
| 5,672,582 A | 9/1997 | Veber et al. | |
| 5,716,929 A | 2/1998 | Bemis et al. | |
| 5,725,878 A | 3/1998 | Al-Razzak et al. | |
| 5,736,520 A | 4/1998 | Bey et al. | |
| 5,756,466 A | 5/1998 | Bemis et al. | |
| 5,760,029 A | 6/1998 | Jadhav et al. | |
| 5,807,876 A | 9/1998 | Armistead et al. | |
| 5,847,135 A | 12/1998 | Bemis et al. | |
| 5,849,866 A | 12/1998 | Kolb et al. | |
| 5,861,267 A | 1/1999 | Su | |
| 5,866,684 A | 2/1999 | Attwood et al. | |
| 5,948,436 A | 9/1999 | Al-Razzak et al. | |
| 5,973,111 A | 10/1999 | Bemis et al. | |
| 5,990,276 A | 11/1999 | Zhang et al. | |
| 6,018,020 A | 1/2000 | Attwood et al. | |
| 6,025,147 A | 2/2000 | Bemis et al. | |
| 6,025,516 A | 2/2000 | Ramaswamy et al. | |
| 6,037,157 A | 3/2000 | Norbeck et al. | |
| 6,046,195 A | 4/2000 | Haworth et al. | |
| 6,054,472 A | 4/2000 | Armistead et al. | |
| 6,060,469 A | 5/2000 | Baker et al. | |
| 6,103,711 A | 8/2000 | Bemis et al. | |
| 6,117,639 A | 9/2000 | Germann et al. | |
| 6,130,315 A | 10/2000 | Kolb et al. | |
| 6,143,715 A | 11/2000 | Llinas-Brunet et al. | |
| 6,153,579 A | 11/2000 | Kim et al. | |
| 6,172,077 B1 | 1/2001 | Curtis et al. | |
| 6,183,121 B1 | 2/2001 | Kim et al. | |
| 6,211,338 B1 | 4/2001 | Malcolm et al. | |
| 6,225,320 B1 | 5/2001 | Kulagowski et al. | |

(Continued)

FOREIGN PATENT DOCUMENTS

DE  3211676 A1  10/1983

(Continued)

OTHER PUBLICATIONS

Martell et al., "High-Throughput Real-Time Reverse Transcription-PCR Quantitation of Hepatitis C Virus RNA," Journal of Clinical Microbiology, pp. 327-332 (1999). Mehdi et al., "The Inhibition of Human Neutrophil Elastase and Cathepsin C by Peptidyl 1,2-Dicarbonyl Derivatives", Biochemical and Biophysical Research Communications, 166(2), pp. 595-600 (Jan. 30, 1990).

Lehmann et al., "Über die chemischen und biologischen Eigenschaften einiger α-Aminoketone" Helvetica Chimica Acta, vol. 33, pp. 1217-1226 (1950).

(Continued)

*Primary Examiner* — Douglas M Willis
(74) *Attorney, Agent, or Firm* — Ropes & Gray LLP

(57) ABSTRACT

The present invention relates to Formula (II) compounds having the structure

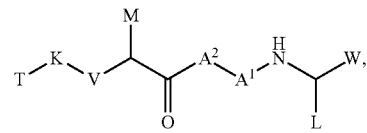

as well as to their use in methods and pharmaceutical compositions for inhibiting proteases, particularly serine proteases, and more particularly HCV NS3 proteases.

9 Claims, No Drawings

U.S. PATENT DOCUMENTS

| | | |
|---|---|---|
| 6,251,583 B1 | 6/2001 | Zhang et al. |
| 6,265,380 B1 | 7/2001 | Tung et al. |
| 6,268,207 B1 | 7/2001 | Bailey |
| 6,274,613 B1 | 8/2001 | Plant et al. |
| 6,303,287 B1 | 10/2001 | Kim et al. |
| 6,323,180 B1 | 11/2001 | Llinas-Brunet et al. |
| 6,329,379 B1 | 12/2001 | Llinas-Brunet et al. |
| 6,329,417 B1 | 12/2001 | Llinas-Brunet et al. |
| 6,344,465 B1 | 2/2002 | Armistead et al. |
| 6,348,608 B1 | 2/2002 | Shi |
| 6,399,771 B1 | 6/2002 | Plant et al. |
| 6,410,531 B1 | 6/2002 | Llinas-Brunet et al. |
| 6,420,380 B2 | 7/2002 | Llinas-Brunet et al. |
| 6,420,522 B1 | 7/2002 | Bemis et al. |
| 6,498,178 B2 | 12/2002 | Stamos et al. |
| 6,528,276 B1 | 3/2003 | Germann et al. |
| 6,534,523 B1 | 3/2003 | Llinas-Brunet et al. |
| 6,541,496 B1 | 4/2003 | Armistead et al. |
| 6,548,555 B1 | 4/2003 | Curatolo et al. |
| 6,602,718 B1 | 8/2003 | Augello et al. |
| 6,608,027 B1 | 8/2003 | Tsantrizos et al. |
| 6,608,067 B1 | 8/2003 | Tung et al. |
| 6,617,309 B2 | 9/2003 | Tung et al. |
| 6,653,127 B1 | 11/2003 | Malcolm et al. |
| 6,653,295 B2 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,800,434 B2 | 10/2004 | Saksena et al. |
| 6,824,769 B2 | 11/2004 | Chaturvedi et al. |
| 6,833,442 B2 | 12/2004 | Shibasaki et al. |
| 6,838,475 B2 | 1/2005 | Arasappan et al. |
| 6,846,802 B2 | 1/2005 | Chen et al. |
| 6,846,806 B2 | 1/2005 | Priestley |
| 6,867,284 B1 | 3/2005 | Matassa et al. |
| 6,872,805 B2 | 3/2005 | Campbell et al. |
| 6,900,238 B1 | 5/2005 | Wong et al. |
| 6,900,434 B2 | 5/2005 | Kuwabara |
| 6,909,000 B2 | 6/2005 | Farmer et al. |
| 6,911,428 B2 | 6/2005 | Zhu et al. |
| 6,914,122 B2 | 7/2005 | Venkatraman et al. |
| 6,919,423 B2 | 7/2005 | Llinas-Brunet |
| 6,939,692 B2 | 9/2005 | Bathe et al. |
| 6,939,854 B2 | 9/2005 | Priestley |
| 7,012,066 B2 | 3/2006 | Saksena et al. |
| 7,034,178 B2 | 4/2006 | Faber et al. |
| 7,091,184 B2 | 8/2006 | Llinas-Brunet et al. |
| 7,105,302 B2 | 9/2006 | Bathe et al. |
| 7,109,172 B2 | 9/2006 | Britt et al. |
| 7,119,073 B2 | 10/2006 | Colarusso et al. |
| 7,122,627 B2 | 10/2006 | Priestley et al. |
| 7,169,760 B2 | 1/2007 | Saksena et al. |
| 7,208,600 B2 | 4/2007 | Cottrell et al. |
| 7,241,796 B2 | 7/2007 | Farmer et al. |
| 7,244,721 B2 | 7/2007 | Saksena et al. |
| 7,250,520 B2 | 7/2007 | Wallace |
| 7,273,885 B2 | 9/2007 | Pitlik et al. |
| 7,288,624 B2 | 10/2007 | Bemis et al. |
| 7,365,092 B2 | 4/2008 | Cottrell et al. |
| 7,371,372 B2 | 5/2008 | Chaturvedi et al. |
| 7,378,422 B2 | 5/2008 | Perni et al. |
| 7,381,827 B2 | 6/2008 | Tanoury et al. |
| 7,388,017 B2 | 6/2008 | Tung et al. |
| 7,494,988 B2 | 2/2009 | Perni et al. |
| 7,504,378 B2 | 3/2009 | Llinas-Brunet et al. |
| 7,592,316 B2 | 9/2009 | Njoroge et al. |
| 7,683,033 B2 | 3/2010 | Cottrell et al. |
| 7,745,444 B2 | 6/2010 | Perni et al. |
| 7,820,671 B2 | 10/2010 | Babine et al. |
| 7,863,274 B2 | 1/2011 | Tung |
| 7,906,550 B2 | 3/2011 | Cottrell et al. |
| 7,964,624 B1 | 6/2011 | Cottrell et al. |
| 7,985,762 B2 | 7/2011 | Cottrell et al. |
| 8,039,623 B2 | 10/2011 | Cottrell et al. |
| 2002/0016294 A1 | 2/2002 | Venkatraman et al. |
| 2002/0016442 A1 | 2/2002 | Llinas-brunet et al. |
| 2002/0032175 A1 | 3/2002 | Tung et al. |
| 2002/0037998 A1 | 3/2002 | Llinas-Brunet et al. |
| 2002/0042046 A1 | 4/2002 | Kim et al. |
| 2002/0045729 A1 | 4/2002 | Kerres et al. |
| 2002/0065248 A1 | 5/2002 | Zhang et al. |
| 2002/0068702 A1 | 6/2002 | Lim-Wilby et al. |
| 2002/0102235 A1 | 8/2002 | Arasappan et al. |
| 2002/0107181 A1 | 8/2002 | Chen et al. |
| 2002/0111378 A1 | 8/2002 | Stamos et al. |
| 2002/0123468 A1 | 9/2002 | Han |
| 2002/0142449 A1 | 10/2002 | Kwong et al. |
| 2002/0147160 A1 | 10/2002 | Bhat et al. |
| 2002/0160962 A1 | 10/2002 | Saksena et al. |
| 2002/0177725 A1 | 11/2002 | Priestley |
| 2002/0183249 A1 | 12/2002 | Taylor et al. |
| 2002/0187488 A1 | 12/2002 | Lin et al. |
| 2003/0008828 A1 | 1/2003 | Priestley et al. |
| 2003/0036501 A1 | 2/2003 | Saksena et al. |
| 2003/0064962 A1 | 4/2003 | Glunz et al. |
| 2003/0068369 A1 | 4/2003 | McAllister et al. |
| 2003/0083467 A1 | 5/2003 | Germann et al. |
| 2003/0100768 A1 | 5/2003 | Han et al. |
| 2003/0119752 A1 | 6/2003 | Farmer et al. |
| 2003/0144257 A1 | 7/2003 | Biggadike et al. |
| 2003/0153788 A1 | 8/2003 | Kobayashi et al. |
| 2003/0181363 A1 | 9/2003 | Llinas-Brunet et al. |
| 2003/0186895 A1 | 10/2003 | Llinas-Brunet et al. |
| 2003/0186952 A1 | 10/2003 | Crew et al. |
| 2003/0187018 A1 | 10/2003 | Llinas-Brunet et al. |
| 2003/0191067 A1 | 10/2003 | Llinas-Brunet et al. |
| 2003/0195362 A1 | 10/2003 | Kempf et al. |
| 2003/0216325 A1 | 11/2003 | Saksena et al. |
| 2003/0236242 A1 | 12/2003 | Perni et al. |
| 2004/0006237 A1 | 1/2004 | Dolitzky et al. |
| 2004/0018986 A1 | 1/2004 | Pitlik et al. |
| 2004/0048774 A1 | 3/2004 | Saunders et al. |
| 2004/0058982 A1 | 3/2004 | Harris |
| 2004/0067901 A1 | 4/2004 | Bhat et al. |
| 2004/0072788 A1 | 4/2004 | Bhat et al. |
| 2004/0077600 A1 | 4/2004 | Tung et al. |
| 2004/0082574 A1 | 4/2004 | Wang et al. |
| 2004/0105820 A1 | 6/2004 | Weers et al. |
| 2004/0110747 A1 | 6/2004 | Altman |
| 2004/0142876 A1 | 7/2004 | Colarusso et al. |
| 2004/0171626 A1 | 9/2004 | Beaulieu et al. |
| 2004/0180815 A1 | 9/2004 | Nakajima et al. |
| 2004/0186125 A1 | 9/2004 | Poupart et al. |
| 2004/0224900 A1 | 11/2004 | Bailey et al. |
| 2004/0229817 A1 | 11/2004 | Duggal et al. |
| 2004/0229818 A1 | 11/2004 | Llinas-Brunet |
| 2004/0266731 A1 | 12/2004 | Tung et al. |
| 2005/0020503 A1 | 1/2005 | Llinas-Brunet et al. |
| 2005/0049220 A1 | 3/2005 | Stuyver |
| 2005/0059606 A1 | 3/2005 | Saksena et al. |
| 2005/0062522 A1 | 3/2005 | Haider et al. |
| 2005/0080005 A1 | 4/2005 | Llinas-Brunet et al. |
| 2005/0080017 A1 | 4/2005 | Cottrell et al. |
| 2005/0090450 A1 | 4/2005 | Farmer et al. |
| 2005/0107304 A1 | 5/2005 | Britt et al. |
| 2005/0112093 A1 | 5/2005 | Ette et al. |
| 2005/0119189 A1 | 6/2005 | Cottrell et al. |
| 2005/0119318 A1 | 6/2005 | Hudyma et al. |
| 2005/0120398 A1 | 6/2005 | Kalkeri et al. |
| 2005/0136400 A1 | 6/2005 | Lin et al. |
| 2005/0137139 A1 | 6/2005 | Perni et al. |
| 2005/0153877 A1 | 7/2005 | Miao et al. |
| 2005/0187165 A1 | 8/2005 | Scola et al. |
| 2005/0187192 A1 | 8/2005 | Fleming et al. |
| 2005/0192212 A1 | 9/2005 | Llinas-Brunet et al. |
| 2005/0197299 A1 | 9/2005 | Babine et al. |
| 2005/0197301 A1 | 9/2005 | Njoroge et al. |
| 2005/0215486 A1 | 9/2005 | Cottrell et al. |
| 2005/0222236 A1 | 10/2005 | Tsantrizos et al. |
| 2005/0249702 A1 | 11/2005 | Njoroge et al. |
| 2005/0287514 A1 | 12/2005 | Byrn |
| 2006/0003317 A1 | 1/2006 | Perni et al. |
| 2006/0003942 A1 | 1/2006 | Tung et al. |
| 2006/0046956 A1 | 3/2006 | Sannigrahi et al. |
| 2006/0089385 A1 | 4/2006 | Cui et al. |
| 2006/0105978 A1 | 5/2006 | Chu et al. |

| | | | | | |
|---|---|---|---|---|---|
| 2006/0205672 A1 | 9/2006 | Saksena et al. | WO | WO-00/31129 | 6/2000 |
| 2006/0211629 A1 | 9/2006 | Britt et al. | WO | WO-00/56331 | 9/2000 |
| 2007/0087973 A1 | 4/2007 | Tanoury et al. | WO | WO-00/59929 | 10/2000 |
| 2007/0105781 A1 | 5/2007 | Lyons et al. | WO | WO-01/02424 | 1/2001 |
| 2007/0161789 A1 | 7/2007 | Cottrell et al. | WO | WO-01/07407 | 2/2001 |
| 2007/0179167 A1 | 8/2007 | Cottrell et al. | WO | WO-01/16300 | 3/2001 |
| 2007/0212683 A1 | 9/2007 | Connelly | WO | WO-01/32691 | 5/2001 |
| 2007/0218012 A1 | 9/2007 | Bittorf et al. | WO | WO-01/40262 | 6/2001 |
| 2007/0218138 A1 | 9/2007 | Bittorf et al. | WO | WO-01/40266 | 6/2001 |
| 2007/0225297 A1 | 9/2007 | Perni et al. | WO | WO-01/58929 | 8/2001 |
| 2007/0231262 A1 | 10/2007 | Lin et al. | WO | WO-01/64678 | 9/2001 |
| 2007/0243166 A1 | 10/2007 | Llinas-Brunet et al. | WO | WO-01/74768 | 10/2001 |
| 2007/0244334 A1 | 10/2007 | Tanoury et al. | WO | WO-01/77113 | 10/2001 |
| 2007/0292933 A1 | 12/2007 | Pitlik et al. | WO | WO-01/81325 | 11/2001 |
| 2008/0045480 A1 | 2/2008 | Farmer et al. | WO | WO-02/07761 | 1/2002 |
| 2008/0070972 A1 | 3/2008 | Kadiyala et al. | WO | WO-02/08187 | 1/2002 |
| 2008/0082155 A1 | 4/2008 | Fischell et al. | WO | WO-02/08198 | 1/2002 |
| 2008/0106058 A1 | 5/2008 | Demick | WO | WO-02/08244 | 1/2002 |
| 2008/0125376 A1 | 5/2008 | Cottrell et al. | WO | WO-02/08251 | 1/2002 |
| 2008/0167480 A1 | 7/2008 | Wallace | WO | WO-02/08256 | 1/2002 |
| 2008/0267915 A1 | 10/2008 | Lin et al. | WO | WO-02/09588 | 2/2002 |
| 2008/0311079 A1 | 12/2008 | Perni et al. | WO | WO-02/18369 | 3/2002 |
| 2009/0022688 A1 | 1/2009 | Farmer et al. | WO | WO-02/22828 | 3/2002 |
| 2009/0098802 A1 | 4/2009 | Talamo | WO | WO-02/48116 | 6/2002 |
| 2009/0143312 A1 | 6/2009 | Tung et al. | WO | WO-02/48157 | 6/2002 |
| 2009/0191555 A1 | 7/2009 | Lin et al. | WO | WO-02/48172 | 6/2002 |
| 2009/0247468 A1 | 10/2009 | Bittorf et al. | WO | WO-02/060926 | 8/2002 |
| 2009/0291902 A1 | 11/2009 | Cottrell et al. | WO | WO-02/079234 | 10/2002 |
| 2010/0137583 A1 | 6/2010 | Babine et al. | WO | WO-03/003804 | 1/2003 |
| 2010/0173851 A1 | 7/2010 | Pitlik et al. | WO | WO-03/006490 | 1/2003 |
| 2010/0272681 A1 | 10/2010 | Farmer et al. | WO | WO-03/020298 | 3/2003 |
| 2010/0330109 A1 | 12/2010 | Cottrell et al. | WO | WO-03/035060 | 5/2003 |
| 2011/0104115 A1 | 5/2011 | Perni et al. | WO | WO-03/053349 | 7/2003 |
| 2011/0112114 A1 | 5/2011 | Tung et al. | WO | WO-03/062228 | 7/2003 |
| 2011/0165120 A1 | 7/2011 | Cottrell et al. | WO | WO-03/062265 | 7/2003 |
| 2011/0182856 A1 | 7/2011 | Cottrell et al. | WO | WO-03/064416 | 8/2003 |
| | | | WO | WO-03/064455 | 8/2003 |
| FOREIGN PATENT DOCUMENTS | | | WO | WO-03/064456 | 8/2003 |
| | | | WO | WO-03/087092 | 10/2003 |
| DE | 19648793 A1 | 5/1998 | WO | WO-03/091202 | 11/2003 |
| EP | 0 195 212 | 9/1986 | WO | WO-03/099274 | 12/2003 |
| EP | 0 275 101 A2 | 7/1988 | WO | WO-03/099316 | 12/2003 |
| EP | 0 356 595 A1 | 3/1990 | WO | WO-2004/026896 | 4/2004 |
| EP | 0 363 284 | 4/1990 | WO | WO-2004/030670 | 4/2004 |
| EP | 0 368 719 A2 | 5/1990 | WO | WO-2004/032827 | 4/2004 |
| EP | 0 417 721 | 3/1991 | WO | WO-2004/037855 | 5/2004 |
| EP | 0 675 112 | 10/1995 | WO | WO-2004/039833 | 5/2004 |
| EP | 1 008 592 A2 | 6/2000 | WO | WO-2004/072243 A2 | 8/2004 |
| EP | 1 498 411 | 1/2005 | WO | WO-2004/089974 | 10/2004 |
| JP | 09124691 A | 5/1997 | WO | WO-2004/092161 | 10/2004 |
| JP | 2001-502694 | 2/2001 | WO | WO-2004/092162 | 10/2004 |
| JP | 2005-535574 | 11/2005 | WO | WO-2004/093798 | 11/2004 |
| WO | WO-92/12140 | 7/1992 | WO | WO-2004/094452 | 11/2004 |
| WO | WO 93/25574 | 12/1993 | WO | WO-2004/103996 | 12/2004 |
| WO | WO-94/14436 | 7/1994 | WO | WO-2004/113365 | 12/2004 |
| WO | WO-95/07696 | 3/1995 | WO | WO-2005/007681 | 1/2005 |
| WO | WO-95/09614 | 4/1995 | WO | WO-2005/010029 | 2/2005 |
| WO | WO 95/35308 | 12/1995 | WO | WO-2005/021584 | 3/2005 |
| WO | WO-96/11697 | 4/1996 | WO | WO-2005/028501 | 3/2005 |
| WO | WO-96/33209 A1 | 10/1996 | WO | WO-2005/028502 | 3/2005 |
| WO | WO-97/17364 A1 | 5/1997 | WO | WO-2005/030796 | 4/2005 |
| WO | WO-97/40028 | 10/1997 | WO | WO-2005/035525 | 4/2005 |
| WO | WO-97/43310 | 11/1997 | WO | WO-2005/037214 | 4/2005 |
| WO | WO-98/13365 | 4/1998 | WO | WO-2005/037860 | 4/2005 |
| WO | WO 98/17679 | 4/1998 | WO | WO-2005/042570 | 5/2005 |
| WO | WO-98/22496 | 5/1998 | WO | WO-2005/046712 | 5/2005 |
| WO | WO-00/09588 | 8/1998 | WO | WO-2005/051410 | 6/2005 |
| WO | WO-98/40381 | 9/1998 | WO | WO-2005/051980 | 6/2005 |
| WO | WO-98/46630 | 10/1998 | WO | WO-2005/054430 | 6/2005 |
| WO | WO-99/07733 | 2/1999 | WO | WO-2005/058821 | 6/2005 |
| WO | WO-99/07734 | 2/1999 | WO | WO-2005/070955 | 8/2005 |
| WO | WO-99/17775 | 4/1999 | WO | WO-2005/073195 | 8/2005 |
| WO | WO-99/37666 | 7/1999 | WO | WO-2005/073216 | 8/2005 |
| WO | WO-99/38888 | 8/1999 | WO | WO-2005/077969 | 8/2005 |
| WO | WO-99/50230 | 10/1999 | WO | WO-2005/085242 | 9/2005 |
| WO | WO-99/64442 | 12/1999 | WO | WO-2005/085275 | 9/2005 |
| WO | WO-00/09543 | 2/2000 | WO | WO-2005/087221 | 9/2005 |
| WO | WO-00/09558 | 2/2000 | WO | WO-2005/087725 | 9/2005 |
| WO | WO-00/16767 | 3/2000 | WO | WO-2005/087731 | 9/2005 |
| WO | WO-00/23421 | 4/2000 | | | |

| WO | WO-2005/095403 | 10/2005 |
| WO | WO-2005/107745 | 11/2005 |
| WO | WO-2005/113581 | 12/2005 |
| WO | WO-2005/123076 | 12/2005 |
| WO | WO-2006/000085 | 1/2006 |
| WO | WO-2006/002539 | 1/2006 |
| WO | WO-2006/007448 | 1/2006 |
| WO | WO-2006/007700 | 1/2006 |
| WO | WO-2006/007708 | 1/2006 |
| WO | WO-2007/016589 | 2/2007 |
| WO | WO-2007/025307 | 3/2007 |
| WO | WO-2008/106058 | 9/2008 |

OTHER PUBLICATIONS

Hanada, M. et al, "Epoxomicin, a new anti-tumour agent of microbial origin," The Journal of Antibiotics, vol. 45(11), pp. 1746-1752 (1992).

Sugawara et al., "Eponemycin, A New Antibiotic Active Against B16 Melanoma," The Journal of Antibiotics, vol. 43(1), pp. 8-18 (1990).

Avolio, "Inhibitors of hepatitis C virum NS3/4A: a-Ketoamide based macrocyclic inhibitors", Bioorganic & Medicinal Chemistry Letters (2009), 19, pp. 2295-2298.

Beak, "Complex Induced Proximity Effects: Enantioselective Syntheses Based on Asymmetric Deprotonations of N-Boc-Pyrrolidines", J. Amer. Chem. Soc., vol. 116(1994), pp. 3231-3239.

Behrens, "Selective Transformations of 2, 3-Epoxy Alcohols and Related Derivatives. Strategies for Nucleophilic Attack at Carbon-3 or Carbon-2", J. Org. Chem., vol. 50 (1985), pp. 5696-5704.

Bergmeier "Synthesis of Bicyclic Proline Analogs Using a formal [3-2] Intramolecular Aziridine-Allylsilane Cycloaddition Reaction", Tetrahedron, vol. 55, No. 26 (1999), pp. 8025-8038.

Blair, "5th Antiviral Drug Discovery and Development Summit", Expert opinion on investigational drugs (2004), 13(8), pp. 1065-1069.

Blankley, "Synthesis and Structure-Activity Relationships of Potent New Abgiotensin Converting Enzyme Inhibitors Containing Saturated Bicyclic Amino Acids", J. of Medicinal Chem., vol. 30 (1987), pp. 992-998.

Cacciola, "The Synthesis of Lysine a-Ketoamide Thrombin Inhibitors via an Epoxy Amide Ring Opening", Tetrahedron Let., vol. 38, No. 33 (1997), pp. 5741-5744.

Chawla, et al., "Challenges in Polymorphism of Pharmaceuticals", CRIPS vol. 5 No. 1, Jan.-Mar. 2004, 4 pages.

Chen, "Discovery of Small-Molecule Inhibitors of HCV NS3-4A Protease as Potential Therapeutic Agents against HCV Infection", Current Medicinal Chemistry (2005), 12(20), pp. 2317-2342.

Chen, "P1 and P1' Optimization of [3,4]-Bicycloproline P2 Incorporated Tetrapeptidyl a-ketoamide Based HCV Protease Inhibitors", Letters in Drug Design and Discovery (2005), 2(2), pp. 118-123.

Chen, "Synthesis and Evaluation of Tripeptidyl a-Ketoamides as Human Rhinovirus 3C Protease Inhibitors", Bioorg. & Med. Chem. Letters, vol. 13, No. 20 (2003), pp. 3531-3536.

Cheng et al, "Stereoselective Synthesis of unnatural Spiroisoxazolinoproline-Based Amino Acids and Derivatives," Journal of Organic Chemistry, pp. 5673-5677 (2002).

Collado, "Stereocontrolled Synthesis of 4-Substituted (±)-Kainic Acids", Journal of Organic Chem., vol. 63 (1998), pp. 1995-2001.

Dixon, "A Sprioisoazolinoproline-based Amino Acid Scaffold for Solid Phase and One-Bead-One-Compound Library Synthesis", Journal of Combinatorial Chemistry, 9(2007), pp. 143-157.

Donkor et al., "Design, Synthesis, Molecular Modeling Studies, and Calpain Inhibitory Activity of Novel a-Ketoamides Incorporating Polar Residues at the PY-Position", J. Med. Chem. 2004, 47, 72-79.

Elemes, "Synthesis of enantiopure a-deuteriated Boc-L-amino acids", J. Chem. Soc., Perkin Trans., vol. 1 (1995), pp. 537-540.

Elofsson et al., "Towards subunit-specific proteasome inhibitors: synthesis and evaluation of peptide α', β'-epoxyketones," Chemistry & Biology, vol. 6, pp. 811-822 (1999).

Esch, P.M., "Reductive Cyclization of Carbon-Centered Glycine Radicals; A Novel Synthetic route to Cyclic a-Amino Acids", Tetrahedron, vol. 48, No. 22 (1992), pp. 4659-4676.

Farmer, L., "Inhibitors of Hepatitis C Virus NS3-4A Protease: P2 Proline Variants," Letters in Drug Design and Discovery (2005), 2, pp. 497-502.

Field, L. et al., "Organic disulfides and Related Substances. 42. Synthesis and Properties of Some Tertiary Disulfides, Especially Involving Penicillamine," J. Org. Chem., pp. 2624-2629 (1979).

Forestier, Current status of subjects receiving peg-interferon-alfa-2a (PEG-IFN) and ribavirin (RBV) after a 14-day study of the hepatitis C protease inhibitor telaprevir (VX-950), with PEG-IFN, Hepatology, vol. 44, Supp. 2 (2006), p. 614A.

Freireich, E., "Quantitative Comparison of Toxicity of Anticancer Agents in Mouse, Rat, Hamster, Dog, Monkey and Man", Cancer Chemother. Rep., vol. 50 No. 219 (1966), pp. 219-244.

Gallagher, D., "Chiral Organolifhium Complexes: The Effect of Ligand Structure on the Enantioselective Deprotonation of Boc-Pyrrolidine", J. Org. Chem., vol. 60 (1995), pp. 8148-8154.

Gallagher, D., "Complex-Induced Proximity Effects: Evidence for a Prelifhiation Complex and a Rate-Determining Deprotonation in the Asymmetric Lithiation of Boc-Pyrrolidine by an -PrLi/(−) Sparteine Complex", J. Org. Chem., vol. 60 (1995), pp. 7092-7093.

Garrison, G., "Novel 3,7-Diheterabicyclo[3.3.1]nonanes that Possess Predominant Class III Antiarrhythmic Activity in 1-4 Day Post Infarction Dog Models: X-ray Diffraction Analysis of 3-[4-(IH-Imidazol-I-yl)benzoy1]-7-isopropyl-3,7-diazabicyclo[3.3.1]nonane Dihydroperchlorate", J. Med. Chem, vol. 39, No. 13 (1996), pp. 2559-2570.

Golina, S., "Vulcanisation of Poly(diefhyl-n-butylamino) Phosphazenes", Internat'l Polymer Science & Tech., vol. 18, No. 3 (1991), pp. T20-T22.

Holladay, M.W. et al., "Dual Antagonists of Platelet Activiating Factor and Histamine. Identification of Structural Requirements for Dual Activity of N-Acyl-4-(5,6-dihydro-11 H-benzo[5,6]cyclohepta-[1,2-b]pyridin-11-ylidene)piperidines," J. Med. Chem., 34, pp. 457-461 (1991).

ISR dated Aug. 3, 2001 from PCT/US2007/004995.
ISR dated Dec. 27, 2007 from PCT/US2006/032481.
ISR dated Jan. 16, 2009 from PCT/US2008/002395.
ISR dated Jul. 23, 2007 from PCT/US2007/006320.
ISR for PCT US 2008 002541, Jul. 7, 2008.

Johansson, P., "Potent inhibitors of the hepatitis C virus NS3 protease: Use of a novel P2 cyclopentane-derived template," Bioorganic & Medicinal Chemistry (2006), 14, pp. 5136-5151.

Kakei, H., "Catalytic Asymmetric Epoxidation of a, β-Unsaturated Esters Using an Yttrium-Biphenyldiol Complex", J. Am. Chem. Soc, vol. 127 (2005), pp. 8962-8963.

Kalkeri, G., "Expression of HCV Protease in the Liver of Mice Results in Liver Injury Which can be Inhibited by VX-950, a Vertex HCV Protease Inhibitor," AALSD Abstracts, Hepatology (2004), 40(1), pp. 281A.

Kamandi, E., "Die Synfhese von β-Phenyl-Isoserinen Durch Ammonolyse von β-Phenyl-Glycidestern, I.", Archiv de Pharmazie, vol. 307 No. 11 (1974), pp. 871-878.

Kanamasa, S. et al., "Highly Diastereoselective Michael Addition of Lithiated Camphor Imines of GLycine Esters to .alpha.,.beta.-Unsaturated Esters. Synthesis of Optically Pure 5-Oxo-2,4-pyrrolidinedicarboxylates of Unnatural Stereochemistry," J. Org. Chem, 56, pp. 2875-2883 (1991).

Kempf, D.J. et al., "Symmetry-Based Inhibitors of HIV Protease. Structure-Activity studirs of Acylated 2,4-Diamino-1,5-diphenyl-3-hydroxypentane and 2,5-Diamino-1,6-diphenylhexane-3,4-diol," J. Med. Chem., pp. 320-330 (1993).

Kerrick, S., "Asymmetric Deprotonations: Enantioselective Syntheses of 2-Substituted (tert-Butoxycarbonyl) pyrrolidines", J. Amer. Chem. Soc, vol. 113 (1991), pp. 9703-9710.

Kieffer, Genetic Heterogeneity in the HCV Ns3 Protease of Untreated Genotype 1 Patients Has Little Effect on the Sensitivity of the VX-950, 12th Internat'l Conf. on Hep. C Virus and Related Viruses, Montreal, Canada, Oct. 2-6, 2005.

Kieffer, T., "Combination of Telaprevir (VX-950) and Peg-Ifn-Alfa Suppresses both Wild-Type Virus and Resistance Variants in HCV Genotype 1-Infected Patients in a 14-Day Phase IB Study", Hepatol. 44, Supp.2 (2006), p. 222A.

Kieffer, T., "Wild-Type HCV NS3 Protease Re-Emerges During Follow-up After 14 days of Dosing with VX-950 in Patients with Genotype 1 HCV", J. Hepatol, vol. 44 Supp. 2 (2006), p. S7.

Kim et al., "Development and Characterization of Proteasome Inhibitors," Methods Enzymol., vol. 399, pp. 585-609 (2005).

Kim, et al., "Broad-spectrum antiviral activity of the IMP dehydrogenase inhibitor VX-497: a comparison with ribavirin and demonstration of antiviral additivity with alpha interferon", Antimicrob Agents Chemother., Apr. 2000; 44(4):859-66.

Kim, J., "Crystal structure of the hepatitis C virus NS3 protease domain complexed with a synthetic NS4A cofactor peptide," Cell, vol. 87, 1996, pp. 343-355 [and Kim, J. "Erratum," Cell, vol. 89, No. 1 (1997), p. 159.

Kim, J., "Hepatitis C Virus NS3 RNA Helicase Domain with a bound Oligonucleotide: The Crystal Structure Provides Insights into the Mode of Unwinding", Structure, vol. 6, No. 1, (1998), pp. 89-100.

Kino, R., "Remarkable Effect of tris(4-fluorphenyl)phosphine Oxide on the Stabilization of Chiral Lanthanum Complex Catalysis. A New and Practical Protocol for the Highly Enantioselective Epoxidation of Conjugated Enones", Org. Biomol. Chem., vol. 2 (2004), pp. 1822-1824.

Kwong, A.D., "An Orally Bioavailable Inhibitor of the HCV NS3-4a Protease; a Potential HCV Therapeutic", 5th Antivir. Drug Disc. and Devel. Summit, (2004).

Kwong, A.D., "Beyond Interferon and Ribavirin: Antiviral Therapies for Hepatitis C Virus", Drug Disc. Today: Ther. Strategies, vol. 3 (2006), pp. 211-220.

Kwong, A.D., "Erratum to 'Hepatitis C Virus NS3/4A Protease' [Antiviral Res. 41 (1998) 1-18]", Antiviral Res., vol. 41 (1999), pp. 1-18.

Kwong, A.D., "Hepatitis C Virus NS3/4A Protease", Antiviral Res., vol. 41 (1999), pp. 67-84.

Kwong, A.D., "Structure and Function of Hepatitis C Virus NS3 Helicase", Top Microbiol. Immunol., vol. 242, (2000), pp. 171-196.

Kwong, HCV Protease Inhibitors: Activity and Resistance, 13th Conference on Retroviruses and Opp. Infections (CROI), Denver, Co, Feb. 5-8, 2006.

Lamar, J., "Novel P4 Truncated Tripeptidyl a-ketoamides as HCV Protease Inhibitors", Bio. & Med. Chem. Let, vol. 14 No. 1 (2004), pp. 263-266.

Landro, J.A. "Mechanistic Role of an NS4A Peptide Cofactor with the Truncated NS3 Protease of Hepatitis C Virus: Elucidation of the NS4A Stimulatory Effect via Kintetic Analysis and Inhibitor Mapping", Biochemistry, 36 (1997) pp. 9340-9348.

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", 12th Intenat'l Symposium on Viral Hep. and Liver Dis., (2006).

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", Gastroenterol., vol. 131, No. 3 (2006), pp. 950-951.

Lin, C., "Discovery and Development of VX-950, a Novel, Covalent and Reversible Inhibitor of Hepatitis C Virus NS3-4A Serine Protease", Infect. disord. Drug Targets, vol. 6, No. 1 (2006), pp. 3-16.

Lin, C., "In Vitro Resistance Studies of Hepatitis C Virus Serine Protease Inhibitors, VX-950 and BILN 2061", J. Biol. Chem., vol. 279, No. 17 (2004), pp. 17508-17514.

Lin, C., "Structure-Based Mutagenesis Study of Hepatitis C Virus NS3 Helicase", J. Virol., vol. 73, No. 10 (1999), pp. 8798-8807.

Lin, K., "Combination of a Hepatitis C Virus N53-NS4A Protease Inhibitor and Alph Interferon Synergistically Inhibits Viral RNA Replication and Facilitates Viral RNA Clearance in Replicon Cells", Antimicrob. Agents Chemo, vol. 48 (2004), pp. 4784-4792.

Lin, K., "VX-950, a Novel Hepatitis C Virus (HCV) N53-4A Protease Inhibitor, Exhibits Potent Antiviral Activities in HCV Replicon Cells", Antimicrob. Agents Chemo, vol. 50, No. 5 (2006), pp. 1813-1822.

Lin, K., "VX-950: A Tight-Binding HCV Protease Inhibitor with a Superior Sustained Inhibitory Response in HCV Replicon Cells", Hepatol, vol. 38 (2003), p. 222A.

Lipinski, "Bioisosteres in Drug Design", Annual Reports in Medicinal Chemistry, 21: 283-291 (1986).

Lohmann, F., "Replication of Subgenomic Hepatitis C Virus RNAs in a Hepatoma Cell Line", Science, 285.5454 (1999) p. 110.

Marigo, M., "Asymmetric Organocatalytic Epoxidation of a,β-Unsaturated Aldehydes with Hydrogen Peroxide", J. Am. Chem. Soc, vol. 127, No. 19 (2005), pp. 6964-6965.

McLaren, R., "Infrared observations of circumstellar ammonia in OH/IR supergiants," Astrophysical Journal (1980), 240 (3, Pt. 2), pp. L159-L163.

Meng et al., "Epoxomicin, a potent and selective proteasome inhibitor, exhibits in vivo antiinflammatory activity," Proc. Natl. Acad. Sci., vol. 96, pp. 10403-10408 (1999).

Monn, J., "A Concise, StereocontrolledThiazoliumYlide Approach to Kainic Acid", J. Organic Chem., vol. 59, No. 10 (1994), pp. 2773-2778.

Morgenstern, J., "Polynucleotide Modulation of the Protease, Nucleoside Triphosphatase, and Helicase Activities of a Hepatitis C Virus NS3-NS4A Complex Isolated from Transfected COS Cells", J. Virol., vol. 71, No. 5 (1997), pp. 3767-3775.

Newman, A., "Solid-state Analysis of the Active Pharmaceutical Ingredient in Drug Products", vol. 8, No. 19 (2003), pp. 898-905.

PCT International Search Report, PCT/US2006/033770, Feb. 15, 2007.

PCT ISR for PCT/US01/26008, Feb. 5, 2002.

PCT ISR for PCT/US05/039240, Dec. 6, 2006.

PCT ISR PCT/US07/64294 dated Nov. 16, 2007.

Perni, "Inhibitors of hepatitis C virus NS3-4A protease: Effect of P4 capping groups on inhibitory potency and pharmacokinetices," Bioorganic & Medicinal Chemistry Letters (2007), 17, pp. 3406-3411.

Perni, Preclinical Profile of VX-950, a Potent, Selective, and Orally Bioavailable Inhibitor of Hepatitis C Virus NS3-4A Serine Protease, Antimicrob. Agents Chemo., vol. 50, No. 3, Mar. 2006, pp. 899-909.

Perni, R., "NS3-4A Protease as a Target for Interfering with Hepatitis C Virus Replication", Drug News Perspect., vol. 13, No. 2 (2000), pp. 69-77.

Perni, R., "The Importance of Backbone Hydrogen Bonds in Binding a Tetrapeptide Scaffold to the HCV NS3-4A Protease," American Chemical Society's 229th National Meeting, San Diego, CA, Mar. 13-17, 2005.

Perni, R., "Toward Smaller HCV NS3-4A Protease Inhibitors: 3-Substituted Proline-based Tripeptide Scaffolds," Abstracts of Papers, 229th ACS National Meeting, San Diego, CA, United States, Mar. 13-17, 2005, MEDI-350.

Perni, R., "VX-950: The Discovery of an Inhibitor of the Hepatitis C NS3-4A Protease and a Potential Hepatitis C Virus Therapeutic", Hepatology, vol. 38 (2003) p. 624A.

Pippel, D., "Complex-Induced Proximity Effects: Steroselective Carbon-Carbon Bond Formation in Chiral Auxiliary Mediated p-Lithiation-Substitution Sequences of β-Substituted Secondary Carboxamides", J. Org. Chem., vol. 63 (1998), pp. 2-3.

Ramachandran, R., "Anti-Viral Activity of VX-950 Resolves Expression of an HCV-Associated Gene Signature", J. Hepatol, vol. 44, Supp. 2 (2006), p. S223.

Reesink, H., "Final Results of a Phase IB, Multiple-Dose Study of VX-950, a Hepatitis C Virus Protease Inhibitor", Hepatology, vol. 42, No. 4, Supp. 1 (2005), pp. 234A-235A.

Reesink, H., "Initial Results of a 14-Day Study of the Hepatitis C Virus Inhibitor Protease VX-950, in combination with Peginterferon-Alpha-2a", J. Hepatol., vol. 44, Supp. 2 (2006), p. S272.

Reesink, H., "Initial Results of a Phase 1B, Multiple-Dose Study of VX-950, a Hepatitis C Virus Protease Inhibitor", Gastroent., vol. 128, No. 4, Supp. 2 (2005), pp. A696-A697.

Reesink, H., "Rapid Decline of Viral RNA in Hepatitis C Patients Treated with VX-950: A Phase Ib, Placebo-Controlled Randomized Study", Gastroenterol., vol. 131, No. 4 (2006), pp. 997-1002.

Rodriguez-Torres, M., "Current Status of Subjects Receiving Peg-Interferon-Alfa-2A (PEG-IFN) and Ribavirin (RBV) Follow-on Therapy After 28-Day Treatment with the Hepatitis C Protease Inhibitor Telaprevir (VX-950), PEG-IFN and RBV", Hepatol., vol. 44, Supp. 2 (2006), p. 532A.

Sagnard, I., "Enantioselective Synthesis of Cyclopropane a-Amino Acids: Synthesis of N-Box-cis-(2S,3R,4S)-3,4-Methanoproline and N-Boc-(2S,3R,4S)-3,4-Methanoglutamic Acid", Tetrahedron, vol. 36, No. 18 (1995), pp. 3149-4039.

Schneider, "Changed Phosphodiesterase Selectivity and Enhanced in vitro Efficacy by Selective Deuteration of Sildenafil", Arzneimittel-Forschung (Drug Res.), vol. 57, No. 6 (2007), pp. 293-298, Editio Cantor Vertag, Aulendorf (Germany).

Schneider, "Enhanced Plasma Concentration by Selective Deuteration of Rofecoxib in Rats", Arzneim.-Forsch., Drug Res., vol. 56, No. 4 (2006), pp. 295-300.

Spaltenstein et al., "Design and Synthesis of Novel Protease Inhibitors. Tripeptide α', β'-Epoxyketones as Nanomolar Inactivators of the Proteasome," Teirahedron Letters, vol. 37(9), pp. 1343-1346 (1996).

Taber, D., "Asymmetric Nucleophillic Epoxidation", Org. Chem. Highlights, (2004).

Taliani, M., "A continuous Assay of Hepatitis C Virus Protease Based on Resonance Energy Transfer Depsipeptide Substrates", Anal. Biochem., vol. 240 (1996), pp. 60-67.

Tan, S., "Strategies for Hepatitis C Therapeutic Intervention: Now and Next", Current Op. in Pharmacology, vol. 4, No. 5 (2004), pp. 465-470.

Thomson, J., "Hepatitis C Virus NS3-4A Protease Inhibitors: countering Viral Subversion in vitro and Showing Promise in the Clinic", Curr. Opin. Drug Discov. Devel., vol. 9, No. 5 (2006), pp. 606-617.

Toom, L., "Microwave-Assisted Raney Nickel Reduction of Bispidinone Thioketals to N,N'- Dialkylbispidines", Synthesis, vol. 12 (2006), pp. 2064-2068.

Udding, J.H., "Transition Metal-Catalyzed Chlorine Transfer Cyclizations of Carbon-Centered Glycine Radicals; A Novel Synthetic Route to Cyclic a-Amino Acids", Tetrahedron, vol. 50, No. 6 (1994), pp. 1907-1918.

Victor, F., "P1 and P3 optimization of novel bicycloproline P2 bearing tetrapeptidyl alpha-ketoamide based HCV protease inhibitors", Bioorganic & Medicinal Chemistry Letters, 14 (2004) pp. 257-261.

Vishweshwar, P., "Pharmaceutical Co-Crystals", J. Pharm. Sci., vol. 95, No. 3 (2006), pp. 499-516.

Wang, Z., "Asymmetric Epoxidation of trans-β-Mefhylstyrene and 1-Phenylcyclohexene Using a D-Fructose-Derived. Ketone: (R,R)-trans-β-Methylstyrene Oxide and (R,R)-I-Phenylcyclohexene Oxide", Org. Syntheses, vol. 80 (2003), p. 9.

White, P.W., "Blunting the Swiss Army Knife of Hepatitis C Virus: Inhibitors of NS3/4A Protease" Progress in Medicinal Chemistry 44 (2006), pp. 65-107.

Yao, N., "Molecular views of viral polyprotein processing revealed by the crystal structure of the hepatitis C virus bifunctional protease-helicase," Structure (1999), 7, pp. 1353-1363.

Yasuda, M., "Synthesis of Conformationally Defined Glutamic Acid Analogues from Readily Available Diels-Alder Adducts", Chem. and Pharm. Bulletin (1995), pp. 1318-1324.

Yee, Ying K.et al., "A Novel Series of Selective Leukotriene Antagonists: Exploration and Optimization of the Acidic Region in 1,6-Disubstituted Indoles and Indazoles," J. Med. Che., 33(9), pp. 2437-2451 (1990).

Yip, Y., "Discovery of a Novel Bicycloproline P2 Bearing Peptidyl a-Ketoamide LY514962 as HCV Protease Inhibitor", Bio. & Med. Chem. Let., vol. 14, No. 1 (2005), pp. 251-256.

Yip, Y., "P4 and P1' Optimization of Bicycloproline P2 Bearing Tetrapeptidyl a-Ketoamides as HCV Protease Inhibitors", Bio. & Med. Chem. Let., vol. 14, No. 9 (2004), pp. 5007-5011.

Akahoshi, "Chimase inhibitors and their therapeutic potential," Drugs of the Future, 27(8):765-777 (2002).

Alberti et al., "Natural History of Hepatitis C", J. Hepatology, 31: 17-24 (1999).

Alter et al., "The Epidemiology of Viral Hepatitis in the United States", Gastroenterol. Clin. North Am., 23:437-455 (1994).

Alter, "Hepatitis C Virus Infection in the United States", J. Hepatology, 31: 88-91 (1999).

Arasappan et al., "Hepatitis C vir NS3-4A serine protease inhibitors: SAR of P'2 moiety with improved potency," Bioorganic and Medicinal Chemistry Letters, 15(19):4180-4194 (2005).

Bartenschlager et al., "Nonstructural Protein 3 of the Hepatitis C Virus Encodes a Serine-Type Proteinase Required for Cleavage at the NS3/4 and NS4/5 Junctions", J. Virol., 67: 3835-3844 (1993).

Bastos et al., "Inhibitors of human heart chymase based on a peptide library," PNAS, 92(15):6738-6742 (1995).

Beaulieu and Llinàs-Brunet, "Therapies for Hepatitis C Infection: Targeting the Non-Structural Proteins", Current Medicinal Chemistry—Anti-Infective Agents, 1: 163-176 (2002).

Burkhart et al., "Preparation of alpha-keto ester enol acetates as potential prodrugs of human neutrophil elastase inhibitors," Bioorganic and Medicinal Chemistry Letters, 8(1):63-64 (1998).

Chambers et al., "Evidence that the N-terminal Domain of Nonstructural Protein NS3 From Yellow Fever Virus Is a Serine Protease Responsible for Site-Specific Cleavages in the Viral Polyprotein", Proc. Natl. Acad. Sci. USA, 87: 8898-8902 (1990).

Choo et al., "Genetic Organization and Diversity of the Hepatitis C Virus", Proc. Natl. Acad. Sci. USA, 88: 2451-2455 (1991).

Clayette et al., "IFN-$_T$, A New Type I IFN with Antiretroviral Activity", Pathol. Biol. (Paris), 47: 553-559 (1999).

Davis et al., "Future Options for the Management of Hepatitis C.", Seminars in Liver Disease, 19: 103-112 (1999).

Di Bisceglie and Hoofnagle, "Optimal Therapy of Hepatitis C", Hepatology, 36: S121-S127 (2002).

Dunsdon et al., "Solid Phase Synthesis of Aminoboronic Acids: Potent Inhibitors of the Hepatitis C Virus NS3 Proteinase", Bioorg. Med. Chem. Lett., 10: 1577-1579 (2000).

Dymock, "Emerging Therapies for Hepatitis C Virus Infections", Emerging Drugs, 6: 13-42 (2001).

Gettins, et al., "Serpin Structure, Mechanism, and Function," Chem. Rev., 102:4751-4803 (2002).

Grakoui et al., "Characterization of the Hepatitis C Virus-Encoded Serine Proteinase: Determination of Proteinase-Dependent Polyprotein Cleavage Sites", J. Virol., 67: 2832-2843 (1993).

Grakoui et al., "Expression and Identification of Hepatitis C Virus Polyprotein Cleavage Products", J. Virol., 67: 1385-1395 (1993).

Han et al., "α-Ketoamides, α-Ketoesters and α-Diketones as HCV NS3 Protease Inhibitors", Bioorg. Med. Chem. Lett., 10: 711-713 (2000).

Heathcote et al. "Peginterferon Alpha-2a in Patients with Chronic Hepatitis C and Cirrhosis", New England Journal of Medicine, 343: 1673-1680 (2000).

Iwarson, "The Natural Course of Chronic Hepatitis", FEMS Microbiology Reviews, 14: 201-204 (1994).

Janssen et al., "Suicide Associated with Alfa-Interferon Therapy for Chronic Viral Hepatitis", J. Hepatol., 21: 241-243 (1994).

Johansson et al., "Acyl sulfonamides as potent protease inhibitors of the hepatitis C vir full-Length NS3 (protease-helicase/NTPase): a comparative study of different C-terminals," Bioorganic and Medicinal Chemistry, 11:2551-2568 (2003).

Kao et al., "Efficacy of Consensus Interferon in the Treatement of Chronic Hepatitis", J. Gastroenterol. Hepatol. 15: 1418-1423 (2000).

Kato et al., "Molecular Cloning of the Human Hepatitis C Virus Genome From Japanese Patients with Non-A, Non-B Hepatitis C", Proc. Natl. Acad. Sci. USA, 87: 9524-9528 (1990).

Kew, "Hepatitis C and Hepatocellular Carcinoma", FEMS Microbiology Reviews, 14: 211-219 (1994).

LaPlante et al., "NMR Line-Broadening and Transferred NOESY as a Medicinal Chemistry Tool for Studying Inhibitors of the Hepatitis C Virus NS3 Protease Domain", Bioorg. Med. Chem. Lett., 10: 2271-2274 (2000).

Lavanchy, "Global Surveillance and Control of Hepatitis C", J. Viral Hepatitis, 6: 35-47 (1999).

Lin et al., "Hepatitis C Virus NS3 Serine Proteinase: Trans-Cleavage Requirements and Processing Kinetics", J. Virol., 68: 8147-8157 (1994).

Lipinski, "Bioisosteres in Drug Design", Annual Reports in Medicinal Chemistry, 27: 283-291 (1986).

Llinàs-Brunet et al., "Highly Potent and Selective Peptide-Based Inhibitors of the Hepatitis C Virus Serine Protease: Towards Smaller Inhibitors", Bioorg. Med. Chem. Lett., 10: 2267-2270 (2000).

Llinàs-Brunet et al., "Peptide-Based Inhibitors of the Hepatitis C Virus Serine Protease", Bioorg. Med. Chem. Lett., 8: 1713-1718 (1998).

Llinàs-Brunet et al., Studies on the C-terminal of hexapeptide inhibitors of the hepatitis C vir serine protease, Bioorganic and Medicinal Chemistry Letters, 8(19):2719-2724 (1998).

Markland et al., "Broad-Spectrum Antiviral Activity of the IMP Dehydrogenase Inhibitor VX-497: A Comparison with Ribavirin and Demonstration of Antiviral Additivity with Alpha Interferon", *Antimicrobial & Antiviral Chemotherapy*, 44: 859-866 (2000).

Moradpour et al., "Current and Evolving Therapies for Hepatitis C", *Eur. J. Gastroenterol. Hepatol.*, 11: 1199-1202 (1999).

Patani et al., "Bioisosterism: A Rational Approach in Drug Design," *Chemical Reviews*, 96(8):3147-3176 (1996).

Perni et al., "Inhibitors of hepatitis C vir NS3.4A protease 1. Noncharged tetrapeptide variants," *Bioorganic and Medicinal Chemistry Letters*, 13(22):4059-4063 (2003).

Perni et al., "Inhibitors of hepatitis C vir NS3.4A protease 2. Warhead SAR and optimization," *Bioorganic and Medicinal Chemistry Letters*, 14(6):1441-1446 (2004).

Perni et al., "Inhibitors of hepatitis C vir NS3.4A protease. Part 3: P2 proline variants," *Bioorganic and Medicinal Chemistry Letters*, 14(8):1939-1942 (2004).

Poliakov et al., "Structure-activity relationship for the selectivity of hepatitis C vir NS3 protease inhibitors," *BBA-General Subject, Elsevier Science Publishers*, NL., 1672:51-59 (2004).

Reddy et al. "Efficacy and Safety of Pegylated (40-kd) Interferon α-2a Compared with Interferon α-2a in Noncirrhotic Patients with Chronic Hepatitis C", *Hepatology*, 33: 433-438 (2001).

Renault and Hoofnagle, "Side Effects of Alpha Interferon", *Seminars in Liver Disease*, 9: 273-277 (1989).

Saito et al., "Hepatitis C Virus Infection Is Associated with the Development of Hepatocellular Carcinoma", *Proc. Natl. Acad. Sci. USA*, 87: 6547-6549 (1990).

Sasaki et al., "A Novel Stereodivergent Synthesis of Optically Pure cis- and trans-3-Substituted Proline Derivatives," *Journal of Organic Chemistry*, 62(3):765-770 (1997).

Sauder "Immunomodulatory and Pharmacologic Properties of Imiquimod", *J. Am. Acad. Dermatol.*, 43: S6-11 (2000).

Schöllkopf et al., "2-Oxazolines from α-Metalated Isocyanides and Carbonyl-Compounds. A New Synthesis for β-Amino Alcohols", *Liebigs Ann. Chem.*: 183-202 (1976).

Semple et al., "New Synthetic Technology for Efficient Construction of α-Hydroxy-β-Amino Amides via the Passerini Reaction", *Org. Letts.*, 2: 2769-2772 (2000).

Takamizawa et al., "Structure and Organization of the Hepatitis C Virus Genome Isolated From Human Carriers," *J. Virol.*, 65: 1105-1113 (1991).

Tazulakhova et al., "Russian Experience in Screening, Analysis, and Clinical Application of Novel Interferon Inducers", *J. Interferon Cytokine Res.*, 21: 65-73 (2001).

Thornber, "Isosterism and Molecular Modification in Drug Design", *Chemical Society Reviews*, 8: 563-580 (1979).

Tomei et al., "NS3 Is a Serine Protease Required for Processing of Hepatitis C Virus Polyprotein", *J. Virol.*, 67: 4017-4026 (1993).

Walker et al., "Hepatitis C Virus: An Overview of Current Approaches and Progress", *DDT*, 4: 518-529 (1999).

Weiland, "Interferon Therapy in Chronic Hepatitis C Virus Infection", *FEMS Microbiol. Rev.*, 14: 279-288 (1994).

Yun et al., "Oxidation of the Antihistaminic Drug Terfenadine in Human Liver Microsomes", *Drug Metabolism & Disposition*, 21: 403-407 (1993).

Office Action dated May 12, 2009 in U.S. Appl. No. 11/511,109.
Office Action dated Apr. 3, 2009 in U.S. Appl. No. 11/434,008.
Office Action dated Feb. 23, 2009 in U.S. Appl. No. 10/614,432.
Office Action dated Jan. 21, 2009 in U.S. Appl. No. 11/051,977.
Office Action dated Dec. 23, 2008 in U.S. Appl. No. 10/344,112.
Office Action dated Dec. 8, 2008 in U.S. Appl. No. 11/716,248.
Office Action dated Dec. 3, 2008 in U.S. Appl. No. 11/880,629.
Office Action dated May 5, 2008 in U.S. Appl. No. 10/943,265.
Office Action dated Apr. 4, 2008 in U.S. Appl. No. 11/051,977.
Office Action dated Mar. 6, 2008 in U.S. Appl. No. 10/344,112.
Office Action dated Feb. 28, 2008 in U.S. Appl. No. 11/434,008.
Office Action dated Jan. 8, 2008 in U.S. Appl. No. 10/821,793.
Office Action dated Sep. 12, 2007 in U.S. Appl. No. 10/943,265.
Office Action dated Sep. 6, 2007 in U.S. Appl. No. 11/051,977.
Office Action dated Jun. 7, 2007 in U.S. Appl. No. 11/434,008.
Office Action dated Jan. 11, 2007 in U.S. Appl. No. 10/943,265.
Office Action dated Dec. 21, 2006 in U.S. Appl. No. 11/051,977.
Office Action dated Oct. 3, 2006 in U.S. Appl. No. 10/821,793.
Office Action dated May 2, 2006 in U.S. Appl. No. 10/943,265.
Office Action dated Jan. 18, 2006 in U.S. Appl. No. 10/821,793.
Office Action dated Nov. 15, 2005 in U.S. Appl. No. 10/943,265.

Kwong, A.D., "A Novel Hepatitis C Protease Inhibitor", HepDART (2005).

LaPlante et al., "NMR Line-Broadening and Transferred NOESY as a Medicinal Chemistry Tool for Studying Inhibitors of the Hepatitis C Virus-NS3 Protease Domain", Bioorg. Med. Chem. Lett., 10: 2271-2274 (2000).

Perni, R., "Properties and Preclinical Profile of VX-950, An Orally Bioavailable Inhibitor of the Hepatitis C Virus (HCV) Protease and a Potential Anti-HCV Therapeutic," 10th International Symposium on Hepatitis C and Related Viruses, Kyoto, Japan, Dec. 2-6, 2003.

Perni, R., "The Design of Inhibitors of the HCV NS3-4A Protease: The Identification of a Clinical Development Candidate, VX-950," ACS National Medicinal Chemistry Symposium, Madison, WI, Jun. 2004.

Patent Abstracts of Japan, vol. 1997, No. 9, Sep. 30, 1997.

Wolff, M.E., "Burger's Medicinal Chemistry and Drug Discovery", Wiley-Interscience, 5th Edition, vol. 1: Principles and Practice, pp. 975-977 (1994).

McIntosh et al., "Diastereoselective alkylation guided by electrophile-nucleophile Π-interactions,"Journal of Organic Chemistry, vol. 53(9), pp. 1947-1952 (2008); Caplus Accession No. 1988:187008 (file last updated Sep. 26, 2011).

Press Release: Vertex Pharmaceuticals Reports Completion of Dosing in the Phase 1a Clinical Study of VX-950, an Oral HCV Protease Inhit. For the Treatment of Hepatis C, Sep. 7, 2004 (p. 1 of 2).

Press Release: "Preclinical data suggest potential for oral combination approaches for HCV," NewsRX, May 31, 2004 (p. 1 of 1).

ated with the Development of Hepatocellular Carcinoma" *Proc. Natl. Acad. Sci. USA* 87, pp. 6547-6549 (1990)]. Unfortunately, there are no broadly effective treatments for the debilitating progression of chronic HCV.

INHIBITORS OF SERINE PROTEASES, PARTICULARLY HEPATITIS C VIRUS NS3 PROTEASE

CROSS REFERENCE TO RELATED APPLICATIONS

This application is a continuation of U.S. patent application Ser. No. 10/607,716, filed Jun. 27, 2003, now U.S. Pat. No. 7,388,017, which is a divisional of U.S. patent application Ser. No. 09/875,390, filed Jun. 6, 2001, now U.S. Pat. No. 6,617,309, which is a divisional of U.S. patent application Ser. No. 09/293,247, filed Apr. 16, 1999, now U.S. Pat. No. 6,265,380, which is a continuation of PCT International Application No. PCT/US97/18968, filed Oct. 17, 1997, which claims priority to U.S. Patent Application No. 60/028,290, filed Oct. 18, 1996, all of which disclosures are incorporated herein by reference in their entireties.

TECHNICAL FIELD OF THE INVENTION

The present invention relates to a novel class of compounds that are useful as protease inhibitors, particularly as serine protease inhibitors, and more particularly as hepatitis C NS3 protease inhibitors. As such, they act by interfering with the life cycle of the hepatitis C virus and are also useful as antiviral agents.

This invention also relates to pharmaceutical compositions comprising these compounds. The compounds and pharmaceutical compositions of this invention are particularly well suited for inhibiting HCV NS3 protease activity and consequently, may be advantageously used as therapeutic agents against the hepatitis C virus and other viruses that are dependent upon a serine protease for proliferation. This invention also relates to methods for inhibiting the activity of proteases, including hepatitis C virus NS3 protease and other serine proteases, using the compounds of this invention and related compounds.

BACKGROUND OF THE INVENTION

Infection by hepatitis C virus ("HCV") is a compelling human medical problem. HCV is recognized as the causative agent for most cases of non-A, non-B hepatitis, with an estimated human seroprevalence of 1% globally [Purcell, R. H., "Hepatitis C virus: Historical perspective and current concepts" *FEMS Microbiology Reviews* 14, pp. 181-192 (1994); Van der Poel, C. L., "Hepatitis C Virus. Epidemiology, Transmission and Prevention in Hepatitis C Virus. Current Studies in Hematology and Blood Transfusion, H. W. Reesink, Ed., (Basel: Karger), pp. 137-163 (1994)]. Four million individuals may be infected in the United States alone [Alter, M. J. and Mast, E. E., "The Epidemiology of Viral Hepatitis in the United States, *Gastroenterol. Clin. North Am.* 23, pp. 437-455 (1994)].

Upon first exposure to HCV only about 20% of infected individuals develop acute clinical hepatitis while others appear to resolve the infection spontaneously. In most instances, however, the virus establishes a chronic infection that persists for decades [Iwarson, S. "The Natural Course of Chronic Hepatitis" *FEMS Microbiology Reviews* 14, pp. 201-204 (1994)]. This usually results in recurrent and progressively worsening liver inflammation, which often leads to more severe disease states such as cirrhosis and hepatocellular carcinoma [Kew, M. C., "Hepatitis C and Hepatocellular Carcinoma", *FEMS Microbiology Reviews*, 14, pp. 211-220 (1994); Saito, I., et al. "Hepatitis C Virus Infection is Asso- The HCV genome encodes a polyprotein of 3010-3033 amino acids [Choo, Q.-L., et al. "Genetic Organization and Diversity of the Hepatitis C Virus", *Proc. Natl. Acad. Sci. USA*, 88, pp. 2451-2455 (1991); Kato, N. et al., Molecular Cloning of the Human Hepatitis C Virus Genome From Japanese Patients with Non-A, Non-B Hepatitis", *Proc. Natl. Acad. Sci. USA*, 87, pp. 9524-9528 (1990); Takamizawa, A. et al., "Structure and Organization of the Hepatitis C Virus Genome Isolated From Human Carriers", *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [Bartenschlager, R. et al., "Nonstructural Protein 3 of the Hepatitis C Virus Encodes a Serine-Type Proteinase Required for Cleavage at the NS3/4 and NS4/5 Junctions", *J. Virol.*, 67, pp. 3835-3844 (1993); Grakoui, A. et al. "Characterization of the Hepatitis C Virus-Encoded Serine Proteinase: Determination of Proteinase-Dependent Polyprotein Cleavage Sites", *J. Virol.*, 67, pp. 2832-2843 (1993); Grakoui, A. et al., Expression and Identification of Hepatitis C Virus Polyprotein Cleavage Products", *J. Virol.*, 67, pp. 1385-1395 (1993); Tomei, L. et al., "NS3 is a serine protease required for processing of hepatitis C virus polyprotein", *J. Virol.*, 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147-8157 (1994)].

The HCV NS3 serine protease and its associated cofactor, NS4A, help process all of the viral enzymes, and are thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man, indicating that interrupting this stage of the viral life cycle results in therapeutically active agents. Consequently it is an attractive target for drug discovery. Unfortunately, there are no serine protease inhibitors available currently as anti-HCV agents.

Furthermore, the current understanding of HCV has not led to any other satisfactory anti-HCV agents or treatments. The only established therapy for HCV disease is interferon treatment. However, interferons have significant side effects (Janssen et al., 1994; Renault and Hoofnagle, 1989) [Janssen, H. L. A., et al. "Suicide Associated with Alfa-Interferon Therapy for Chronic Viral Hepatitis" *J. Hepatol.*, 21, pp. 241-243 (1994)]; Renault, P. F. and Hoofnagle, J. H., "Side effects of alpha interferon. Seminars in Liver Disease 9, 273-277. (1989)] and induce long term remission in only a fraction (~25%) of cases [Weiland, O. "Interferon Therapy in Chronic Hepatitis C Virus Infection", *FEMS Microbiol. Rev.*, 14, PP.

279-288 (1994)]. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention provides compounds, and pharmaceutically acceptable derivatives thereof, that are useful as protease inhibitors, particularly as serine protease inhibitors, and more particularly as HCV NS3 protease inhibitors. These compounds can be used alone or in combination with immunomodulatory agents, such as α-, β- or γ-interferons; other antiviral agents such as ribavirin and amantadine; other inhibitors of hepatitis C protease; inhibitors of other targets in the HCV life cycle including the helicase, the polymerase, the metalloprotease, or the internal ribosome entry; or combinations thereof.

The present invention also provides methods for inhibiting proteases, particularly serine proteases, and more particularly HCV NS3 protease.

The present invention also provides pharmaceutical compositions comprising the compounds of this invention, as well as multi-component compositions comprising additional immunomodulatory agents, such as α-, β- or γ-interferons; other antiviral agents such as ribavirin and amantadine; other inhibitors of hepatitis C protease; inhibitors of other targets in the HCV life cycle including the helicase, the polymerase, the metalloprotease or the internal ribosome entry; or combinations thereof. The invention also provides methods of using the compounds of this invention, as well as other related compounds, for the inhibition of HCV.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Abu | aminobutyric acid |
| Ac | acetyl |
| AcOH | acetic acid |
| Bn | benzyl |
| Boc | tert-butyloxycarbonyl |
| Bz | benzoyl |
| Cbz | carbobenzyloxy |
| CDI | carbonyldiimidazole |
| DCE | 1,2-dichloroethane |
| DCM | dichloromethane |
| DIEA | diisopropylethylamine |
| DMA | dimethylacetamide |
| DMAP | dimethylaminopyridine |
| DMF | dimethylformamide |
| DPPA | diphenylphosphorylazide |
| DMSO | dimethylsulfoxide |
| Et | ethyl |
| EtOAc | ethyl acetate |
| FMOC | 9-fluorenylmethoxycarbonyl |
| HbtU | O-benzotriazolyl-N,N,N',N'-tetramethyluronium hexafluorophosphate |
| HOBt | N-hydroxybenzotriazole |
| HPLC | high performance liquid chromatography |

| Designation | Reagent or Fragment |
| --- | --- |
| Me | methyl |
| MS | mass spectrometry |
| NMP | N-methyl pyrrolidinone |
| ND | not determined |
| Pip | piperidine |
| Prz | piperazine |
| PyBrop | bromo-tris-pyrrolidinophosphonium hexafluorophosphate |
| Pyr | pyridine |
| THF | tetrahydrofuran |
| TFA | trifluoroacetic acid |
| TFE | trifluoroethanol |
| Tol | toluene |

The following terms are used herein:

Unless expressly stated to the contrary, the terms "—SO$_2$—" and "—S(O)$_2$—" as used herein refer to a sulfone or sulfone derivative (i.e., both appended groups linked to the S), and not a sulfinate ester.

The term "substituted" refers to the replacement of one or more hydrogen radicals in a given structure with a radical selected from a specified group. When more than one hydrogen radical may be replaced with a substituent selected from the same specified group, the substituents may be either the same or different at every position.

As used herein, the term "amino" refers to a trivalent nitrogen which may be primary or which may be substituted with 1-2 alkyl groups.

The term "alkyl" or "alkane", alone or in combination with any other term, refers to a straight-chain or branched-chain saturated aliphatic hydrocarbon radical containing the specified number of carbon atoms, or where no number is specified, preferably from 1-10 and more preferably from 1-5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl" or "alkene", alone or in combination with any other term, refers to a straight-chain or branched-chain mono- or poly-unsaturated aliphatic hydrocarbon radical containing the specified number of carbon atoms, or where no number is specified, preferably from 2-10 carbon atoms and more preferably, from 2-5 carbon atoms. Examples of alkenyl radicals include, but are not limited to, ethenyl, E- and Z-propenyl, E- and Z-isobutenyl, E- and Z-pentenyl, E- and Z-hexenyl, E,E-, E,Z-, Z,E-, and Z-Z-hexadienyl and the like.

The term "alkynyl" or "alkyne", alone or in combination with any other term, refers to a straight-chain or branched-chain mono or poly-unsaturated aliphatic hydrocarbon radical containing the specified number of carbon atoms, or where no number is specified, preferably from 2-10 carbon atoms and more preferably, from 2-5 carbon atoms, wherein at least one of the unsaturated aliphatic hydrocarbon radicals comprises a triple bond. Examples of alkynyl radicals include, but are not limited to, ethynyl, propynyl, isobutynyl, pentynyl, hexynyl, hexenynyl, and the like.

The term "aryl", alone or in combination with any other term, refers to a carbocyclic aromatic radical containing the specified number of carbon atoms, and which may be optionally fused, for example benzofused, with one to three cycloalkyl, aromatic, heterocyclic or heteroaromatic rings. Preferred aryl groups have from 6-14 carbon atoms, and more preferred groups from 6-10 carbon atoms. Examples of aryl radicals include, but are not limited to, phenyl, naphthyl, anthracenyl and the like.

The term "carbocycle", alone or in combination with any other term, refers to a stable non-aromatic 3- to 8-membered carbon ring radical which may be saturated, mono-unsaturated or poly-unsaturated, and which may be optionally fused, for example benzofused, with one to three cycloalkyl, aromatic, heterocyclic or heteroaromatic rings. The carbocycle may be attached at any endocyclic carbon atom which results in a stable structure.

The terms "cycloalkyl" or "cycloalkane", alone or in combination with any other term, refers to a stable non-aromatic 3- to 8-membered carbon ring radical which is saturated and which may be optionally fused, for example benzofused, with one to three cycloalkyl, aromatic, heterocyclic or heteroaromatic rings. The cycloalkyl may be attached at any endocyclic carbon atom which results in a stable structure. Preferred carbocycles have 5 to 6 carbons. Examples of carbocycle radicals include, but are not limited to, cyclopropyl, cyclobutyl, cyclopentyl, cyclohexyl, cycloheptyl, cyclopentenyl, cyclohexenyl, indane, tetrahydronaphthalene and the like.

The term "cycloalkenyl" or "cycloalkene" alone or in combination with any other term, refers to a stable cyclic hydrocarbon ring radical containing at least one endocyclic carbon-carbon double bond. The carbocycle may be attached at any cyclic carbon atom which results in a stable structure. Where no number of carbon atoms is specified, a cycloalkenyl radical preferably has from 5-7 carbon atoms. Examples of cycloalkenyl radicals include, but are not limited to, cyclopentenyl, cyclohexenyl, cyclopentadienyl, indenyl and the like.

The term "cycloalkylidenyl", alone or in combination with any other term, refers to a stable cyclic hydrocarbon ring radical containing at least one exocyclic carbon-carbon double bond, wherein the cyclic hydrocarbon ring may be optionally fused, for example benzofused, with one to three cycloalkyl, aromatic, heterocyclic or heteroaromatic rings. The carbocycle may be attached at any cyclic carbon atom, which results in a stable structure. Where no number of carbon atoms is specified, a cycloalkylidenyl radical preferably has from 5-7 carbon atoms. Examples of cycloalkylidenyl radicals include, but are not limited to, cyclopentylidenyl, cyclohexylidenyl, cyclopentenylidenyl and the like.

The skilled practitioner would realize that certain groups could be classified either as cycloalkanes or as aryl groups. Examples of such groups include indanyl and tetrahydronaphthyl groups.

The term "monocycle" or "monocyclic" alone or in combination with any other term, unless otherwise defined herein, refers to a 5-7 membered ring system.

The term "bicycle" or "bicyclic" alone or in combination with any other term, unless otherwise defined herein, refers to a 6-11 membered ring system.

The term "tricycle" or "tricyclic" alone or in combination with any other term, unless otherwise defined herein, refers to a 11-15 membered ring system.

The terms "heterocyclyl" and "heterocycle", alone or in combination with any other term, unless otherwise defined herein, refers to a stable 5- to 15-membered mono-, bi-, or tricyclic, heterocyclic ring which is either saturated or partially unsaturated, but not aromatic, and which may be optionally fused, for example benzofused, with one to three cycloalkyl, aromatic, heterocyclic or heteroaromatic rings. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocycle may be attached at any endocyclic carbon or heteroatom which results in the creation of a stable structure.

Preferred heterocycles defined above include, for example, imidazolidinyl, indazolinolyl, perhydropyridazyl, pyrrolinyl, pyrrolidinyl, piperidinyl, pyrazolinyl, piperazinyl, morpholinyl, thiamorpholinyl, β-carbolinyl, thiazolidinyl, thiamorpholinyl sulfone, oxopiperidinyl, oxopyrrolidinyl, oxoazepinyl, azepinyl, furazanyl, tetrahydropyranyl, tetrahydrofuranyl, oxathiolyl, dithiolyl, tetrahydrothiophenyl, dioxanyl, dioxolanyl, tetrahydrofurotetrahydrofuranyl, tetrahydropyranotetrahydrofuranyl, tetrahydrofurodihydrofuranyl, tetrahydropyranodihydrofuranyl, dihydropyranyl, dihydrofuranyl, dihydrofurotetrahydrofuranyl, dihydropyranotetrahydrofuranyl, sulfolanyl and the like.

The terms "heteroaryl" and "heteroaromatic" alone or in combination with any other term, unless otherwise defined herein, refers to a stable 3- to 7-membered monocyclic heterocyclic ring which is aromatic, and which may be optionally fused, for example, benzofused, with one to three cycloalkyl, aromatic, heterocyclic or heteroaromatic rings. Each heteroaromatic ring consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heteroaromatic ring may be attached at any endocyclic carbon or heteroatom which results in the creation of a stable, aromatic structure.

Preferred heteroaromatics defined above include, for example, benzimidazolyl, imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, pyridazinyl, furyl, thienyl, triazolyl, triazolyl, tetrazolyl, benzofuranyl, oxazolyl, benzoxazolyl, isoxazolyl, isothiazolyl, thiadiazolyl, thiophenyl, and the like.

The term "halo" refers to a radical of fluorine, chlorine, bromine or iodine. Preferred halogen radicals include fluorine and chlorine.

In chemical formulas, parentheses are used herein to indicate 1) the presence of more than one atom or group bonded to the same atom or group; or 2) a branching point in a chain (i.e., the group or atom immediately before the open parenthesis is bonded directly to the group or atom immediately after the closed parenthesis). An example of the first use is "$N(R^1)_2$" denoting two $R^1$ groups bound to the nitrogen atom. An example of the second use is "$—C(O)R^1$" denoting an oxygen atom and a $R^1$ bound to the carbon atom, as in the following structure:

As used herein, "B" indicates a boron atom.

The present invention provides compounds that are useful as protease inhibitors, particularly as serine protease inhibitors, and more particularly as HCV NS3 protease inhibitors. As such, they act by interfering with the life cycle of the HCV virus and other viruses that are dependent upon a serine protease for proliferation. Therefore, these compounds are useful as antiviral agents.

Accordingly, in one embodiment, the present invention provides a compound of the formula (I):

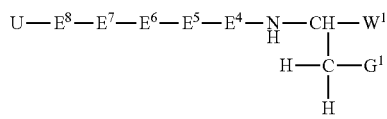

(I)

wherein:

G¹ is thiol, hydroxyl, thiomethyl, alkenyl, alkynyl, trifluoromethyl, $C_{1-2}$ alkoxy, $C_{1-2}$ alkylthio, or $C_{1-3}$ alkyl, wherein the $C_{1-3}$ alkyl group is optionally substituted with thiol, hydroxyl, thiomethyl, alkenyl, alkynyl, trifluoromethyl, $C_{1-2}$ alkoxy, or $C_{1-2}$ alkylthio.

W¹ is:

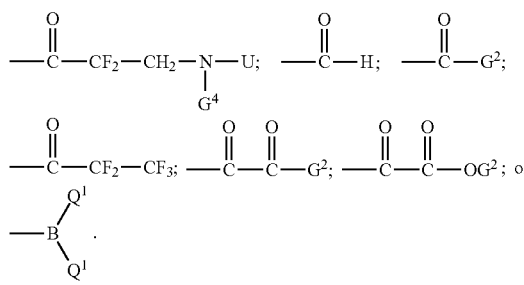

G² is alkyl, aryl, aralkyl, or a mono-, bi- or tricyclic heterocycle, optionally substituted with 1-3 groups selected from alkyl, alkenyl, alkynyl, aralkyl, alkoxy, alkenoxy, aryloxy, heterocyclyl, heterocyclylalkyl, aralkoxy, heterocyclylalkoxy, oxo, hydroxy, amino, alkanoylamino, alkoxycarbonylamino, ureido, carboxy, heterocyclyloxyalkyl, aryloxyalkyl, heterocyclylcarbonyl, aroyl, arylsulfonyl, heterocyclylsulfonyl, heterocyclylsulfonylamino, arylsulfonamido, aralkylsulfonamido, heterocyclylalkanoyl, carboxyalkyl, carboxyamidoalkyl, alkanesulfonyl, sulfonamido, halo, cyano, or haloalkyl.

G⁴ is alkyl, alkenyl, alkynyl, cycloalkyl, cycloalkylalkyl, cycloalkylalkenyl, aryl, aralkyl, aralkenyl, heterocyclyl, heterocyclylalkyl, heterocyclylalkenyl, hydroxyalkyl, alkoxyalkyl, alkylthioalkyl, arylthioalkyl, or heterocyclylthioalkyl.

Each Q¹ is hydroxy, alkoxy, or aryloxy, or each Q¹ is an oxygen atom and together with the boron to which they are bound, form a 5-7 membered ring, wherein the ring atoms are carbon, nitrogen or oxygen.

U is hydrogen, G⁹-C(O)—, G⁹-SO₂—, G⁹-C(O)—C(O)—, (G⁹)₂-N—C(O)—C(O)—, (G⁹)₂-N—SO₂—, (G⁹)₂N—C(O)—, or G⁹-O—C(O)—.

G⁹ is hydrogen, alkyl, carboxyalkyl, alkenyl, aryl, aralkyl, aralkenyl, cycloalkyl, cycloalkylalkyl, cycloalkenyl, heterocyclyl, heterocyclylalkyl, or heterocyclyalkenyl optionally substituted with 1-3 groups selected from alkyl, alkenyl, aralkyl, alkoxy, alkenoxy, aryloxy, heterocyclyl, carboxyalkyl, carboxyamidoalkyl, alkylsulfonyl, or sulfonamido; or two G⁹ groups, together with the nitrogen atom to which they are bound, form a 4-10 membered nitrogen containing monocyclic or bicyclic saturated or partially unsaturated ring system, wherein 1-2 of the atoms forming the ring are N, S, or O and the other atoms forming the ring are C; wherein the ring system is optionally substituted by one or two groups selected from alkyl, alkenyl, aralkyl, alkoxy, alkenoxy, aryloxy, aralkoxy, heterocyclyl, keto, hydroxy, amino, alkanoyl amino, carboxy, carboxyalkyl, carboxamidoalkyl, sulfonyl, or sulfonamido.

E⁴ is a bond;

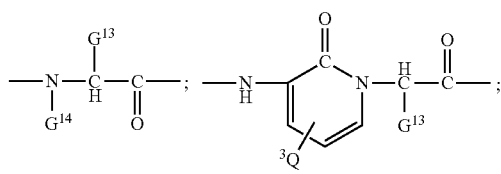

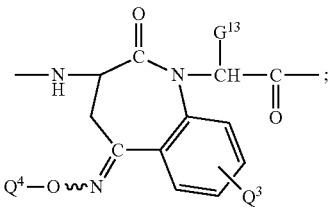

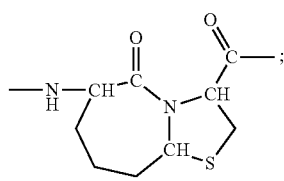

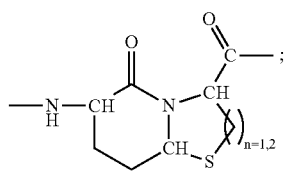

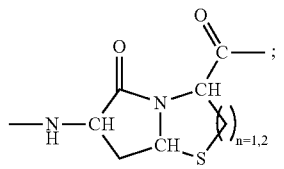

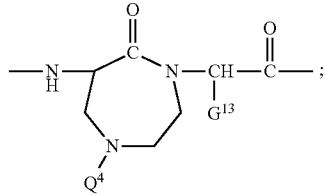

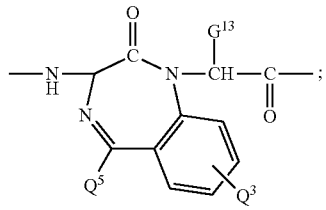

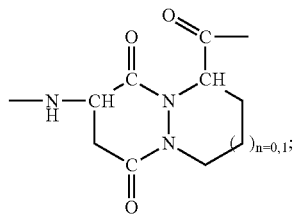

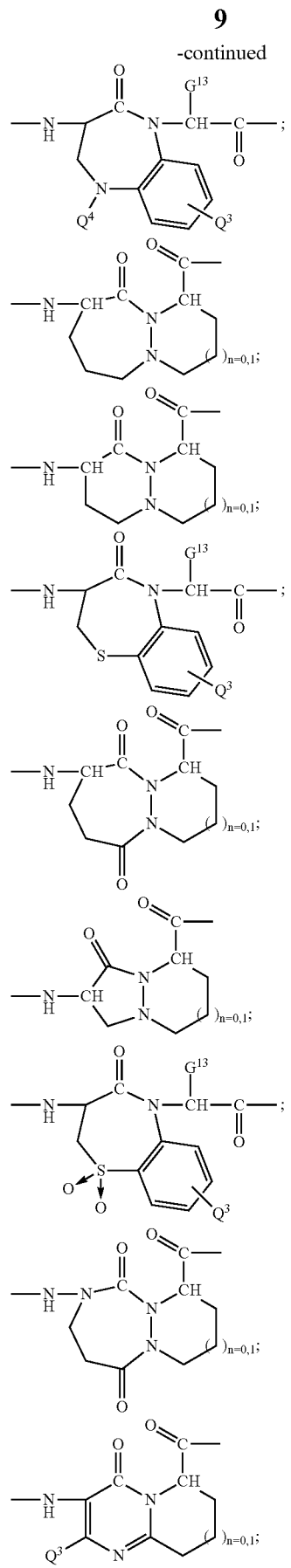
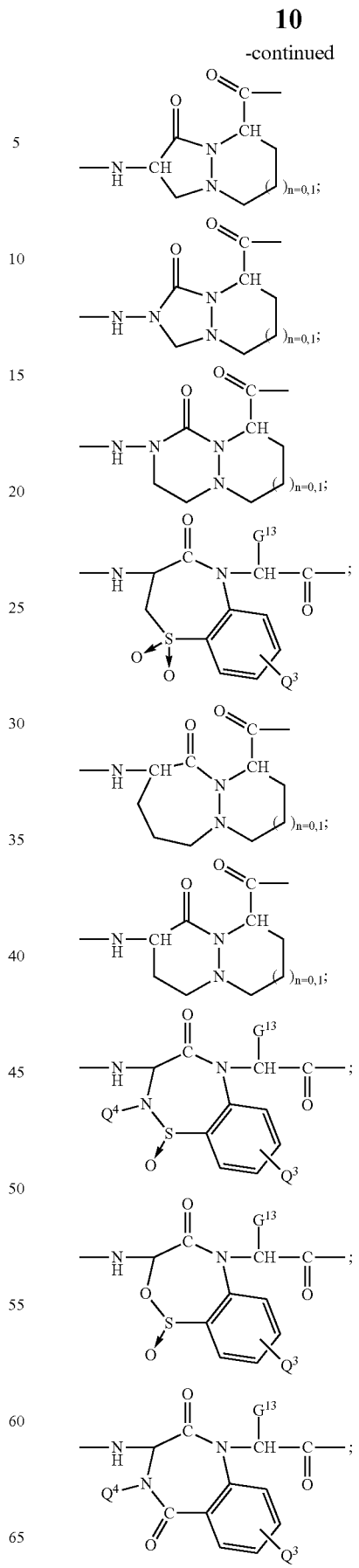

-continued

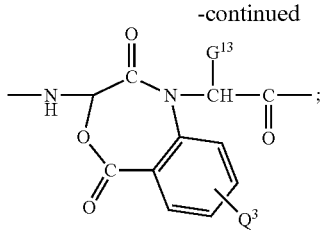

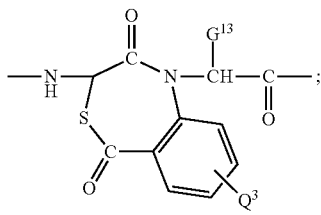

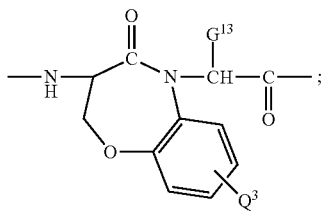

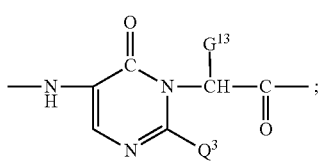

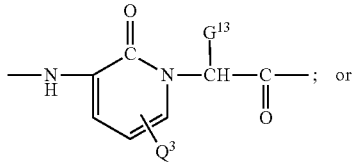

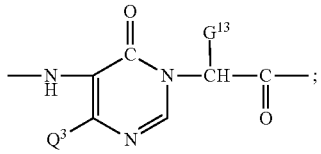

wherein:

$G^{13}$ is cycloalkylalkyl, aralkyl, heterocycylalkyl, aralkoxyalkyl, heterocycylalkoxyalkyl, aralkylthioalkyl, or heterocylalkylthioalkyl, optionally substituted by 1-2 alkyl, alkenyl, aralkyl, alkoxy, alkenoxy, aryloxy, aralkoxy, heterocyclyl, oxo, hydroxy, amino, alkanoylamino, carboxy, carboxyalkyl, carboxamidoalkyl, sulfonyl, or sulfonamido groups.

$G^{14}$ is hydrogen, alkyl, alkenyl, hydroxy, alkoxy, or —CH$_2$-G$^8$, wherein G8 is aryl, aralkyl, carbocyclyl or heterocyclyl, where the ring portion of each aryl, aralkyl, or heterocycle is optionally substituted with 1-3 groups selected from alkyl, alkenyl, aralkyl, alkoxy, alkenoxy, aryloxy, heterocyclyl, heterocyclylalkyl, aralkoxy, heterocyclylalkoxy, oxo, hydroxy, amino, alkanoylamino, alkoxycarbonylamino, ureido, carboxy, carboxyalkyl, carboxyamidoalkyl, alkanesulfonyl, sulfonamido, halo, cyano, or haloalkyl; or when $E^4$ is:

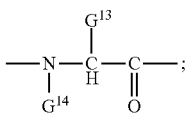

$G^{13}$ and $G^{14}$, together with the atoms to which they are bound (carbon and nitrogen, respectively), form a nitrogen-containing heterocyclic ring system having 4-7 members, which optionally contains one to two additional heteroatoms, wherein the resulting ring system is optionally fused with an additional carbocyclic or heterocyclic ring system to form a bicyclic ring system comprising 7-11 atoms; and wherein the monocyclic or bicyclic ring system is optionally substituted by one or two groups selected from oxo, hydroxy, alkyl, alkenyl, aryl, aralkyl, alkyl, alkenoxy, aryloxy, aralkyloxy, halo, or nitro.

Each $Q^3$ is halo, nitro, cyano, alkyl, alkenyl, aralkyl, alkoxy, alkenoxy, aryloxy, aralkoxy, heterocyclyl, heterocyclylalkyl, hydroxy, amino, alkylamino, alkanoylamino, carboxy, carboxyalkyl, carboxamidoalkyl, alkylsulfonyl, arylsulfonyl, aralkylsulfonyl, alkylsulfonamido, arylsulfonamido, or aralkylsulfonamido, wherein any alkyl, alkenyl, aryl, or heterocyclyl groups is optionally substituted with 1-3 groups selected from keto, hydroxy, nitro, cyano, halo, amino, alkyl, alkoxy, or alkylthio; wherein $Q^3$, when not bonded to a specific atom, may be bonded to any substitutable atom.

$Q^4$ is independently alkyl, cycloalkyl, aryl, aralkyl, heterocyclyl, heterocyclylalkyl, alkanoyl, arylcarbonyl, aralkylcarbonyl, alkoxycarbonyl, aryloxycarbonyl, aralkyloxycarbonyl, alkylsulfonyl, arylsulfonyl, aralkylsulfonyl, alkylaminocarbonyl, arylaminocarbonyl, aralkylaminocarbonyl, wherein any of said alkyl, cycloalkyl, aryl, aralkyl, heterocyclyl groups is optionally substituted with one or more groups independently selected from keto, hydroxy, nitro, cyano, halo, amino, alkyl, alkoxy, or alkylthio.

$Q^5$ is aryl or an aromatic heterocycle, wherein:

the aryl or aromatic heterocycle is monocyclic, bicyclic, or tricyclic having 5-14 atoms, and is optionally substituted with 1-3 groups selected from hydroxy, nitro, cyano, halo, amino, alkyl, alkoxy, alkanoyl, alkylamino, or alkylthio.

$E^5$ is a bond or

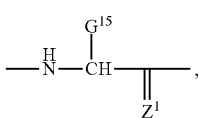

wherein $G^{15}$ is alkyl, alkenyl, cycloalkylalkyl, aralkyl, heterocyclylalkyl, carboxyalkyl, or carboxamidoalkyl, where the ring of any aralkyl or heterocyclylalkyl group is optionally substituted with 1-2 alkyl, alkenyl, aralkyl, alkoxy, alkenoxy, aryloxy, aralkoxy, heterocyclyl, oxo, hydroxy, amino, alkanoylamino, carboxy, carboxyalkyl, carboxamidoalkyl, sulfonyl, or sulfonamido groups.

$E^6$ is a bond or $$-\underset{H}{N}-\underset{\underset{G^{16}}{|}}{CH}-\underset{\underset{O}{\|}}{C}-,$$

wherein $G^{16}$ is hydrogen, alkyl, alkenyl, aralkyl, or cycloalkylalkylyl;

$E^7$ is a bond or $$-\underset{H}{N}-\underset{\underset{G^{17}}{|}}{CH}-\underset{Z^1}{\overset{}{C}}-,$$

wherein $G^{17}$ is alkyl optionally substituted with carboxy; wherein the alkyl is preferably $C_{1-3}$ alkyl.

$E^8$ is a bond or $$-\underset{H}{N}-\underset{\underset{G^{18}}{|}}{CH}-\underset{\underset{O}{\|}}{C}-,$$

wherein $G^{18}$ is alkyl optionally substituted with carboxy; wherein the alkyl is preferably $C_{1-3}$ alkyl.

Each $Z^1$ is independently O or $H_2$ provided that no more than two $Z^1$ groups is $H_2$ in a given compound.

Preferred compounds of formula (I) are those in which at least one substituent is defined as follows:

$G^1$ is vinyl, acetylenyl, $-CH_3$, $-CF_3$, $-CH_2CH_3$, $-CH_2CF_3$, $-SCH_3$, $-SH$, $-CH_2SH$, or $-CH_2OH$;

$G^{13}$ is $C_{3-6}$ branched alkyl or $G^{13}$ and $G^{14}$, together with the atoms to which they are bound (carbon and nitrogen, respectively), form a nitrogen-containing heterocyclic ring system having 4-7 members, which optionally contains one to two additional heteroatoms, wherein the monocyclic or bicyclic ring system is optionally substituted by one or two groups selected from oxo, hydroxy, alkyl, alkenyl, aryl, aralkyl, alkyl, alkenoxy, aryloxy, aralkyloxy, halo, or nitro; and $Z^1$ is O.

More preferred compounds of formula (I) are those wherein $G^1$ is $-SH$, $-CH_2SH$, $-CF_3$, or $-CF_2CF_3$.

Most preferred compounds of formula (I) are those wherein $G^1$ is $-SH$ or $-CF_3$.

According to another embodiment, the present invention provides a compound of the formula (I), wherein $W^1$ is as defined below for W and the other substituents are as defined above.

According to another embodiment, the present invention provides a compound of the formula (II):

$$T-K\overset{M}{\underset{V}{-}}\overset{}{\underset{\underset{O}{\|}}{C}}-A^2-A^1-\underset{H}{N}-\underset{L}{\overset{}{C}}-W \qquad (II)$$

In these compounds:

W is:

[structures shown]

m is 0 or 1.

Each $R^1$ is hydroxy, alkoxy, or aryloxy, or each $R^1$ is an oxygen atom and together with the boron, to which they are each bound, form a 5-7 membered ring, wherein the ring atoms are carbon, nitrogen, or oxygen.

Each $R^2$ is independently hydrogen, alkyl, alkenyl, aryl, aralkyl, aralkenyl, cycloalkyl, cycloalkylalkyl, cycloalkenyl, cycloalkenylalkyl, heterocyclyl, heterocyclylalkyl, heterocyclylalkenyl, heteroaryl, or heteroaralkyl, or two $R^2$ groups, which are bound to the same nitrogen atom, form together with that nitrogen atom, a 5-7 membered monocyclic heterocyclic ring system; wherein any $R^2$ carbon atom is optionally substituted with J.

J is alkyl, aryl, aralkyl, alkoxy, aryloxy, aralkoxy, cycloalkyl, cycloalkoxy, heterocyclyl, heterocyclyloxy, heterocyclylalkyl, keto, hydroxy, amino, alkylamino, alkanoylamino, aroylamino, aralkanoylamino, carboxy, carboxyalkyl, carboxamidoalkyl, halo, cyano, nitro, formyl, acyl, sulfonyl, or sulfonamido and is optionally substituted with 1-3 $J^1$ groups.

$J^1$ is alkyl, aryl, aralkyl, alkoxy, aryloxy, heterocyclyl, heterocyclyloxy, keto, hydroxy, amino, alkanoylamino, aroylamino, carboxy, carboxyalkyl, carboxamidoalkyl, halo, cyano, nitro, formyl, sulfonyl, or sulfonamido.

L is alkyl, alkenyl, or alkynyl, wherein any hydrogen bound to a carbon atoms is optionally substituted with halogen, and wherein any hydrogen or halogen atom bound to any terminal carbon atom is optionally substituted with sulfhydryl or hydroxy.

$A^1$ is a bond,

[structures shown]

R⁴ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups.

R⁵ and R⁶ are independently hydrogen, alkyl, alkenyl, aryl, aralkyl, aralkenyl, cycloalkyl, cycloalkylalkyl, cycloalkenyl, heterocyclyl, heterocyclylalkyl, heteroaryl, or heteroaralkyl, and is optionally substituted with 1-3 J groups.

X is a bond, —C(H)(R⁷)—, —O—, —S—, or —N(R⁸)—.

R⁷ is hydrogen, alkyl, alkenyl, aryl, aralkyl, heterocyclyl, heterocyclylalkyl, heteroaryl, or heteroaralkyl, and is optionally substituted with 1-3 J groups.

R⁸ is hydrogen alkyl, aryl, aralkyl, heterocyclyl, heterocyclylalkyl, heteroaryl, heteroaralkyl, aralkanoyl, heterocyclanoyl, heteroaralkanoyl, —C(O)R¹⁴, —SO₂R¹⁴, or carboxamido, and is optionally substituted with 1-3 J groups; or R⁸ and Z, together with the atoms to which they are bound, form a nitrogen containing mono- or bicyclic ring system optionally substituted with 1-3 J groups.

R¹⁴ is alkyl, aryl, aralkyl, heterocyclyl, heterocyclylalkyl, heteroaryl, or heteroaralkyl.

Y is a bond, —CH₂—, —C(O)—, —C(O)C(O)—, —S(O)—, —S(O)₂—, or —S(O)(NR⁷)—, wherein R⁷ is as defined above.

Z is alkyl, aryl, aralkyl, cycloalkyl, cycloalkylalkyl, heterocyclyl, heterocyclylalkyl, heteroaryl, heteroaralkyl, —OR², or —N(R²)₂, wherein any carbon atom is optionally substituted with J, wherein R² is as defined above.

A² is a bond or

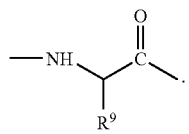

R⁹ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups.

M is alkyl, cycloalkyl, aryl, aralkyl, heterocyclyl, heterocyclylalkyl, heteroaryl, or heteroaralkyl, and is optionally substituted by 1-3 J groups, wherein any alkyl carbon atom may be replaced by a heteroatom.

V is a bond, —CH₂—, —C(H)(R¹¹)—, —O—, —S—, or —N(R¹¹)—.

R¹¹ is hydrogen or $C_{1-3}$ alkyl.

K is a bond, —O—, —S—, —C(O)—, —S(O)—, —S(O)₂—, or —S(O)(NR¹¹)—, wherein R¹¹ is as defined above.

T is —R¹², -alkyl-R¹², -alkenyl-R¹², -alkynyl-R¹², —OR¹², —N(R¹²)₂, —C(O)R¹², —C(=NOalkyl)R¹², or

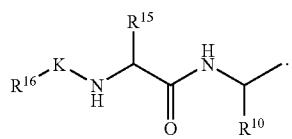

Each R¹² is hydrogen, aryl, heteroaryl, cycloalkyl, heterocyclyl, cycloalkylidenyl, or heterocycloalkylidenyl, and is optionally substituted with 1-3 J groups, or a first R¹² and a second R¹², together with the nitrogen to which they are bound, form a mono- or bicyclic ring system optionally substituted by 1-3 J groups.

R¹⁰ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups.

R¹⁵ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups.

R¹⁶ is hydrogen, alkyl, aryl, heteroaryl, cycloalkyl, or heterocyclyl.

Preferably, W is

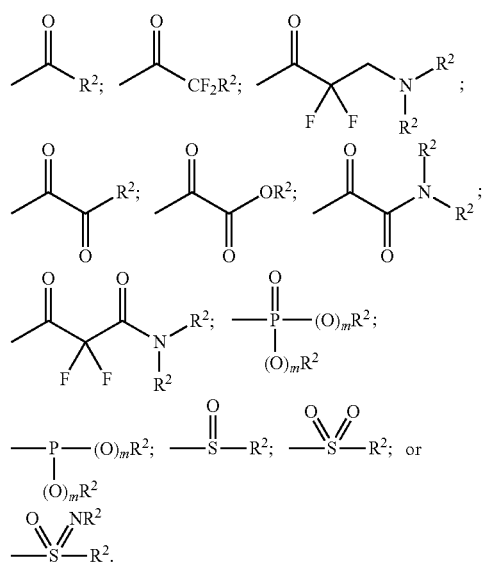

More preferably, W is

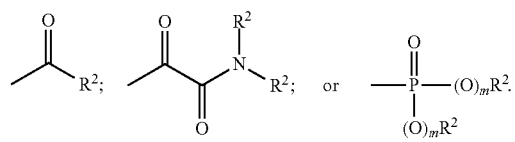

Most preferably, W is

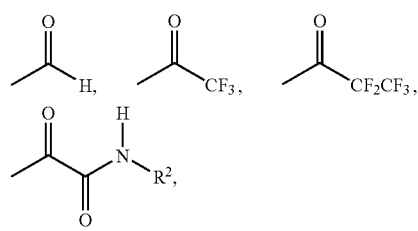

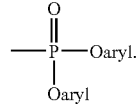

wherein $R^2$ is aralkyl; or

Preferably, J is alkyl, alkoxy, aryloxy, aryl, aralkyl, aralkoxy, halo, heteroaryl, cyano, amino, nitro, heterocyclyl, acyl, carboxy, carboxyalkyl, alkylamino, hydroxy, heterocyclylalkyl, aralkanoylamino, aroylamino, alkanoylamino, formyl or keto.

More preferably, J is t-butyl, methyl, trifluoromethyl, methoxy, ethoxy, trifluoromethoxy, carboxy, phenyl, benzyl, phenoxy, benzyloxy, fluoro, chloro, bromo, isoxazolyl, pyridinyl, piperidinyl, carboxymethyl, carboxyethyl; dialkylamino, morpholinylmethyl, phenylacetylamino, or acylamino.

Preferably, $J^1$ is alkoxy, alkyl, halo or aryl.

More preferably, $J^1$ is $C_{1-3}$ alkoxy, chloro, $C_{1-3}$alkyl, or phenyl.

Preferably, L is alkyl, alkenyl, allyl, or propargyl.

More preferably, L is trihalomethyl, sulfhydryl or alkyl substituted with trihalomethyl, sulfhydryl, or hydroxy.

Preferably, $R^4$ is alkyl, aralkyl, or cycloalkylalkyl, or cycloalkyl. More preferably, $R^4$ is phenylalkyl or cycloalkyl. Most preferably, $R^4$ is isobutyl, cyclohexylalkyl, or phenethyl.

Preferably, $R^5$ and $R^6$ are each hydrogen.

Preferably, X is —O— or —N($R^8$)—.

Preferably, $R^8$ is hydrogen.

Preferably, Y is —$CH_2$—, —C(O)—, —C(O)C(O)—, or —S(O)$_2$—.

Preferably, $R^2$ is H, fluorine, trifluoromethyl, alkyl, aryl, aralkyl, heteroaralkyl, heterocyclyl, or heterocyclylalkyl.

Preferably, Z is alkyl, aryl, aralkyl, heterocyclyl, cycloalkyl, heteroaryl, $OR^2$, or $N(R^2)_2$, wherein $R^2$ is preferably aralkyl or alkenyl.

More preferably, Z is phenyl, 1,4-benzodioxanyl, 1,3-benzodioxolyl, benzothiazolyl, naphthyl, benzyl, oxadiazolyl, isoxazolyl, quinolyl, benzothiophenyl, thiazolyl, cyclohexyl, butyl, naphthyl, dioxolanyl, benzyl, pyridinyl, morpholinyl, N-anilinyl, N-aminobenzothiazole, N-aminobenzodioxole, N-aminonapthylene, N-benzylamine, N-aminopyridine, benzyloxy, allyloxy, or phenethyl, and is optionally substituted with J.

Most preferably, Z is naphthyl, 3,4-dichlorophenyl, 2-carbomethoxyphenyl.

Preferably, $R^9$ is alkyl. More preferably, $R^9$ is propyl. Most preferably, $R^9$ is isopropyl.

Preferably, M is alkyl, heteroaralkyl, aryl, cycloalkylalkyl, aralkyl, or aralkyl, wherein one of the alkyl carbon atoms is replaced by O or S.

More preferably M is propyl, methyl, pyridylmethyl, benzyl, naphthylmethyl, phenyl, imidazolylmethyl, thiophenylmethyl, cyclohexylmethyl, phenethyl, benzylthiomethyl, or benzyloxyethyl.

Preferably, V is —N($R^{11}$)—.

Preferably, $R^{11}$ is hydrogen.

Preferably, K is —C(O)— or —S(O)$_2$—.

Preferably, T is —$R^{12}$, -alkyl-$R^{12}$, -alkenyl-$R^{12}$, —$OR^{12}$, —$N(R^{12})_2$, —C(=NOalkyl)$R^{12}$, or

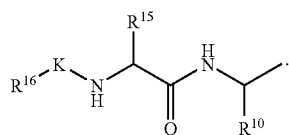

More preferably, T is —$R^{12}$ or -alkyl-$R^{12}$.

Preferably, $R^{12}$ is aryl or heteroaryl and is optionally substituted by 1-3 J groups. More preferably, $R^{12}$ is 1-naphthyl, isoquinolyl, indolyl, or 2-alkoxy-1-naphthyl.

Preferably, $R^{10}$ is alkyl substituted with carboxy. More preferably, $R^{10}$ is $C_{1-3}$ alkyl substituted with carboxy.

Preferably, $R^{15}$ is alkyl substituted with carboxy. More preferably, $R^{15}$ is $C_{1-3}$ alkyl substituted with carboxy.

In a preferred embodiment of formula (II), $A^1$ is:

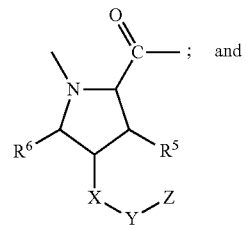

$A^2$ is a bond.

Preferably, in this preferred embodiment, X is O.

More preferably, Y is —$CH_2$—.

Alternatively, Y is —C(O)—.

Alternatively, Y is —C(O)— and Z is —$N(R^2)_2$.

Alternatively, in this preferred embodiment, X is —N($R^8$)—.

More preferably, Y is —C(O)—.

Alternatively, Y is —S(O)$_2$—.

Alternatively, Y is —C(O)— and Z is —$N(R^2)_2$.

Alternatively, in this preferred embodiment, X is —N($R^8$)—, wherein $R^8$ is —C(O)$R^{14}$ or —S(O)$_2R^{14}$.

More preferably, when $R^8$ is —C(O)$R^{14}$, Y is —C(O)—.

Alternatively, Y is —S(O)$_2$—.

Alternatively, Y is —C(O)— and Z is —$N(R^2)_2$.

More preferably, when $R^8$ is —S(O)$_2R^{14}$, Y is —C(O)— and Z is —$N(R^2)_2$.

In a more preferred embodiment of this invention are compounds of formula (II), wherein $A^1$ is:

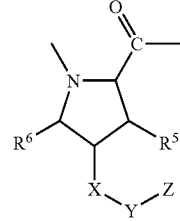

wherein, X is —O— and Y is —$CH_2$—;

$A^2$ is

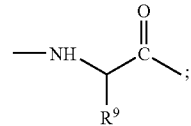

V is —($NR^{11}$)—, and

K is —C(O)—.

In another more preferred embodiment of this invention are compounds of formula (II), wherein $A^1$ is:

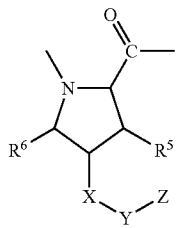

wherein, X is O and Y is $CH_2$,
$A^2$ is:

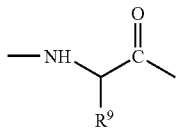

V is —$N(R^{11})$—, and
K is —$S(O)_2$—.

In another more preferred embodiment of this invention are compounds of formula (II), wherein $A^1$ is:

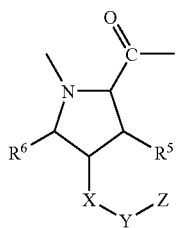

wherein, X is O and Y is a —$CH_2$—,
$A^2$ is a bond;
V is —$N(R^{11})$—, and
K is —C(O)—.

In another more preferred embodiment of this invention are compounds of formula (II), wherein $A^1$ is:

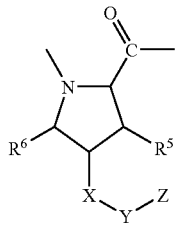

wherein, X is O and Y is —$CH_2$—,
$A^2$ is a bond;
V is —$N(R^{11})$—, and
K is —$S(O)_2$—.

Preferably, in these more preferred embodiments, W is:

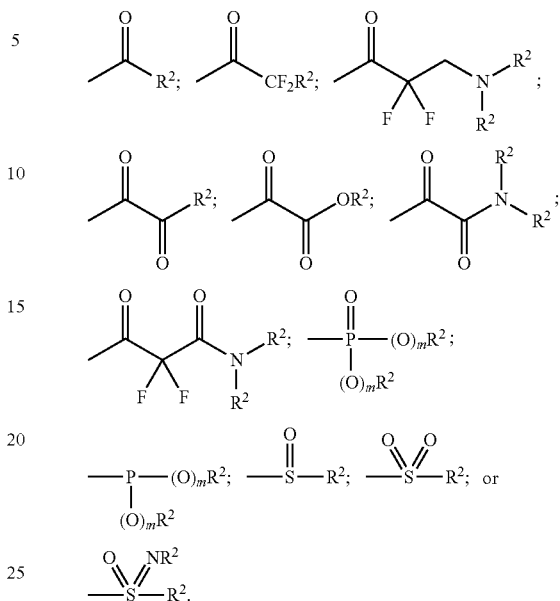

More preferably, W is

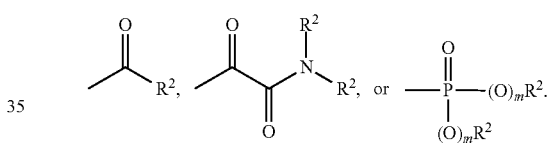

Most preferably, W is

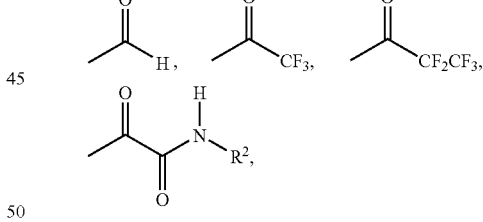

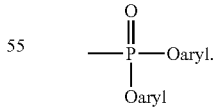

wherein $R^2$ is aralkyl; or

Preferably, in these more preferred embodiments, L is alkyl, alkenyl, allyl, or propargyl.

More preferably, L is trihalomethyl, sulfhydryl or alkyl substituted with trihalomethyl, sulfhydryl, or hydroxy.

In another preferred embodiment of formula (II), $A^1$ is

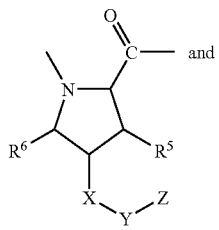 and $A^2$ is a bond. Preferred groups in this preferred embodiment are as described above.

In another preferred embodiment of formula (II), $A^1$ is a bond. Preferred groups in this preferred embodiment are as described above.

In another preferred embodiment of formula (II), $A^1$ is

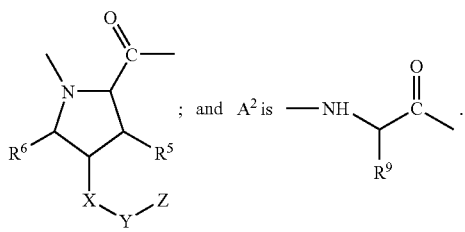

The preferred, more preferred, and most preferred groups of this preferred embodiment are as described above.

This invention anticipates that many active-site directed inhibitors of the NS3 protease may be peptidomimetic in nature and thus may be designed from the natural substrate. Therefore, preferred substituents in peptidomimetic inhibitors of this invention include those which correspond to the backbone or side chains of naturally occurring substrates or synthetic substrates with high affinity for the enzyme (low $K_m$).

In another preferred embodiment of formula (II), $A^1$ is a bond. The preferred, more preferred, and most preferred compounds of this preferred embodiment are as described above.

The skilled practitioner would realize that some certain groups could be classified either as heterocycles or heteroaromatics, depending on the point of attachment.

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. Combinations of substituents and variables envisioned by this invention are only those that result in the formation of stable compounds. The term "stable", as used herein, refers to compounds which possess stability sufficient to allow manufacture and which maintain their integrity for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of this invention may be synthesized using conventional techniques. Advantageously, these compounds are conveniently synthesized from readily available starting materials.

As used herein, the compounds of this invention, including the compounds of formulae (I) and (II), are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

Accordingly, this invention also provides prodrugs of the compounds of this invention, which are derivatives that are designed to enhance biological properties such as oral absorption, clearance, metabolism or compartmental distribution. Such derivatives are well known in the art.

As the skilled practitioner realizes, the compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The term "protected" refers to when the designated functional group is attached to a suitable chemical group (protecting group). Examples of suitable protecting groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

Particularly favored derivatives and prodrugs are those that increase the bioavailability of the compounds of this invention when such compounds are administered to a mammal (e.g., by allowing an orally administered compound to be more readily absorbed into the blood), have more favorable clearance rates or metabolic profiles, or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae (I) and (II).

Pharmaceutically acceptable salts of the compounds of this invention include those derived from pharmaceutically acceptable inorganic and organic acids and bases. Examples of suitable acid salts include ace-tate, adipate, alginate, aspartate, benzoate, benzene-sulfonate, bisulfate, butyrate, citrate, camphorate, camphorsulfonate, cyclopentanepropionate, digluconate, dodecyl sulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphtha-lenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N—$(C_{1-4}$ alkyl$)_4^+$ salts. This invention also envisions the quaternization of any basic nitrogen-containing groups of the compounds disclosed herein. Water or oil-soluble or dispersible products may be obtained by such quaternization.

In general, compounds of formulae (I) and (II) are obtained via methods illustrated in Examples 1-8. As can be appreciated by the skilled artisan however the synthetic schemes set forth herein are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Without being bound by theory, we believe that the compounds of this invention interact either covalently or noncovalently with the active site of the HCV NS3 protease and other serine proteases, inhibiting the ability of such an enzyme to cleave natural or synthetic substrates. Noncovalent interactions are advantageous in that they impart relatively greater specificity of inhibition and will not inhibit other undesirable targets, e.g. cysteine proteases. These compounds will therefore have a greater therapeutic index when administered to mammals than covalent protease inhibitors, which can interact with a wide range of proteases and cause undesirable toxic effects. In contrast, covalent interactions are advantageous in that they impart greater inhibitory potency allowing lower doses to be administered and thus ameliorating any lack of specificity problems.

The novel compounds of the present invention are excellent inhibitors of proteases, particularly serine proteases, and more particularly HCV NS3 proteases. Accordingly, these compounds are capable of targeting and inhibiting proteases, particularly serine proteases, and more particularly HCV NS3 proteases. As such, these compounds interfere with the life cycle of viruses, including HCV, and are thus useful as antiviral agents. Inhibition can be measured by various methods such as the methods of Example 11.

The term "antiviral agent" refers to a compound or drug which possesses viral inhibitory activity. Such agents include reverse transcriptase inhibitors (including nucleoside and non-nucleoside analogs) and protease inhibitors. Preferably the protease inhibitor is a HCV protease inhibitor.

The term "treating" as used herein refers to the alleviation of symptoms of a particular disorder in a patient or the improvement of an ascertainable measurement associated with a particular disorder. As used herein, the term "patient" refers to a mammal, including a human.

Thus, according to another embodiment this invention provides pharmaceutical compositions comprising a compound of formula (I) or (II) or a pharmaceutically acceptable salt thereof; an additional agent selected from, but not exclusively, an immunomodulatory agent, such as α-, β-, or γ-interferon; other antiviral agents, such as ribavarin or amantadine; other inhibitors of HCV protease; inhibitors of other targets in the HCV life cycle such as helicase, polymerase, or metalloprotease; or combinations thereof and any pharmaceutically acceptable carrier, adjuvant or vehicle. An alternate embodiment provides compositions comprising a compound of formula (I) or (II) or a pharmaceutically acceptable salt thereof; and a pharmaceutically acceptable carrier, adjuvant or vehicle. Such composition may optionally comprise an additional agent selected from an immunomodulatory agent, such as α-, β-, or γ-interferon; other antiviral agents, such as ribavarin; other inhibitors of HCV protease; inhibitors of HCV helicase; or combinations thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol, polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as "α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of formula (I) or (II).

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica (*Ph. Helv.*) or a similar alcohol, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula (I) or (II) and one or more additional therapeutic or prophylactic agents, both the compound and the additional agent should be present at dosage levels of between about 10 to 100%, and more preferably between about 10 to 80% of the dosage normally administered in a monotherapy regimen.

According to one embodiment, the pharmaceutical compositions of this invention comprise an additional immunomodulatory agent. Examples of additional immunomodulatory agents include, but are not limited to, $\alpha$-, $\beta$-, and $\gamma$-interferons.

According to an alternate embodiment, the pharmaceutical compositions of this invention may additionally comprise an anti-viral agent. Examples of anti-viral agents include ribavirin and amantadine.

According to another alternate embodiment, the pharmaceutical compositions of this invention may additionally comprise other inhibitors of HCV protease.

According to yet another alternate embodiment, the pharmaceutical compositions of this invention may additionally comprise an inhibitor of other targets in the HCV life cycle, such as helicase, polymerase, or metalloprotease.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

When these compounds or their pharmaceutically acceptable salts are formulated together with a pharmaceutically acceptable carrier, the resulting composition may be administered in vivo to mammals, such as man, to inhibit serine proteases, particularly HCV NS3 protease or to treat or prevent viral infection, particularly HCV virus infection. Such treatment may also be achieved using the compounds of this invention in combination with agents which include, but are not limited to: immunomodulatory agents, such as $\alpha$-, $\beta$-, or $\gamma$-interferons; other antiviral agents such as ribavirin, amantadine; other inhibitors of HCV NS3 protease; inhibitors of other targets in the HCV life cycle such as helicase, polymerase, metalloprotease, or internal ribosome entry; or combinations thereof. These additional agents may be combined with the compounds of this invention to create a single dosage form. Alternatively these additional agents may be separately administered to a mammal as part of a multiple dosage form.

Accordingly, another embodiment of this invention provides methods of inhibiting serine protease activity in mammals by administering a compound of formula (I) or (II), wherein the substituents are as defined above. Preferably, the serine protease is HCV NS3.

In an alternate embodiment, the invention provides methods of inhibiting HCV or HCV NS3 activity in a mammal comprising the step of administering to said mammal, a compound of formula (I) or (II), wherein the substituents are as defined above.

In an alternate embodiment, this invention provides methods of decreasing serine protease activity in a mammal comprising the step of administrating to said mammal any of the pharmaceutical compositions and combinations described above. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle. Such additional agent may be administered to the mammal prior to, concurrently with, or following the administration of the HCV inhibitor composition.

In a preferred embodiment, these methods are useful in decreasing HCV NS3 protease activity in a mammal. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle such as helicase, polymerase, or metalloprotease. Such additional agent may be administered to the mammal prior to, concurrently with, or following the administration of the compositions of this invention.

In an alternate preferred embodiment, these methods are useful for inhibiting viral replication in a mammal. Such methods are useful in treating or preventing, for example, viral diseases, such as HCV. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle. Such additional agent may be administered to the mammal prior to, concurrently with, or following the administration of the composition according to this invention.

The compounds set forth herein may also be used as laboratory reagents. The compounds of this invention may also be used to treat or prevent viral contamination of materials and therefore reduce the risk of viral infection of laboratory or medical personnel or patients who come in contact with such materials. These materials include, but are not limited to, biological materials, such as blood, tissue, etc; surgical instruments and garments; laboratory instruments and garments; and blood collection apparatuses and materials.

In order that this invention be more fully understood, the following examples are set forth. These examples are for the purpose of illustration only and are not to be construed as limiting the scope of the invention in any way.

General Materials and Methods

A general synthetic methodology for preparing compounds of this invention is provided in Example 1. More specific methodologies for preparing compounds of this invention, including compounds 1-198, are provided in Examples 2-9.

The HPLC data reported in Tables 1-7 is expressed in terms of solvent gradient, retention time, and % purity. Deionized water was used in each method.

The correct $(M+H)^+$ and/or $(M+Na)^+$ molecular ions for all compounds were obtained by either matrix-assisted laser desorption mass spectrometry (Kratos MALDI I) or by electro spray mass spectrometry (MICROMASS Quatro II).

Example 1

Numerous amino acids for use in the synthesis of peptidyl and peptidomimetic compounds of this invention may be purchased commercially from, for instance, Sigma Chemical Company or Bachem Feinchemikalien AG (Switzerland). Amino acids that are not commercially available can be made by known synthetic routes ("Kinetic Resolution of Unnatural and Rarely Occurring Amino Acids: Enantioselective Hydrolysis of N-Acyl Amino Acids Catalyzed by Acylase I", Chenault, H. K. et. al., *J. Am. Chem. Soc.* 111, 6354-6364 (1989) and references cited therein; "Synthesis of β-γ-Unsaturated Amino Acids by the Strecker Reaction, Greenlee, W. J., *J. Org. Chem.* 49, 2632-2634 (1984); "Recent Stereoselective Synthetic Approaches to Beta-amino Acids", Cole, D. *Tetrahedron* 50: 9517 (1994); "The Chemistry of Cyclic Alpha Imino Acids", Mauger, A. B; Volume 4 of "Chemistry and Biochemistry of Amino Acids, Peptides, and Proteins", Weinstein, B. editor, Marcel Dekker (1977); "Recent Progress in the Synthesis and Reactions of Substituted Piperidines", Org. Prep. Procedure Int. 24, 585-621 (1992), all of which are incorporated herein by reference).

Certain compounds of formula (I) or (II) may be synthesized from amino acids by procedures which are well known in the art of peptide and organic chemical synthesis. Examples of such syntheses are generally set forth in Bodanszky and Bodanszky, "The Practice of Peptide Synthesis", Springer-Verlag, Berlin, Germany (1984), "The Peptides", Gross and Meinhofer, eds; Academic Press, 1979, Vols. I-III, and Stewart, J. M. and Young, J. D., "Solid Phase Peptide Synthesis, Second Edition", Pierce Chemical Company, Rockford, Ill. (1984); and "Recent Advances in the Generation of Molecular Diversity", Moos, W. H., Green, G. D. and Pavia, M. R. in "Annual Reports in Medicinal Chemistry, Vol. 28" pp. 315-324; Bristol, J. A., ed.; Academic Press, San Diego, Calif. (1993), all of which are incorporated herein by reference.

Typically, for solution phase synthesis of peptides, the α-amine of the amino acid to be coupled is protected by a urethane such as Boc, Cbz, Fmoc or Alloc while the free carboxyl is activated by reaction with a carbodiimide such as DCC, EDC, or DIC, optionally in the presence of a catalyst such as HOBT, HOAt, HOSu, or DMAP. Other methods, which proceed through the intermediacy of activated esters, acid halides, enzyme-activated amino acids and anhydrides including phosphonium reagents such as BOP, Py-BOP, N-carboxy-anhydrides, symmetrical anhydrides, mixed carbonic anhydrides, carbonic-phosphinic and carbonic-phosphoric anhydrides, are also suitable. After the peptide has been formed, protecting groups may be removed by methods described in the references listed above, such as by hydrogenation in the presence of a palladium, platinum or rhodium catalyst, treatment with sodium in liquid ammonia, hydrochloric, hydrofluoric, hydrobromic, formic, trifluoromethanesulfonic, or trifluoroacetic acid, secondary amines, fluoride ion, trimethylsilyl halides including bromide and iodide, or alkali. Automation of the synthetic process, using techniques such as those set forth above, can be accomplished by use of commercially available instrumentation, including but not limited to the Advanced Chemtech 357 FBS and 496 MOS; Tecan CombiTec, and Applied Biosystems 433A among others. Specific application of these methods and their equivalents, depending upon the target compound, will be apparent to those skilled in the art. Modifications of chemical processes and choice of instrumentation is within the skill of the ordinary practitioner.
Example 2
Compounds 1-26 (Table 1) were prepared as described in scheme 1.
SCHEME 1
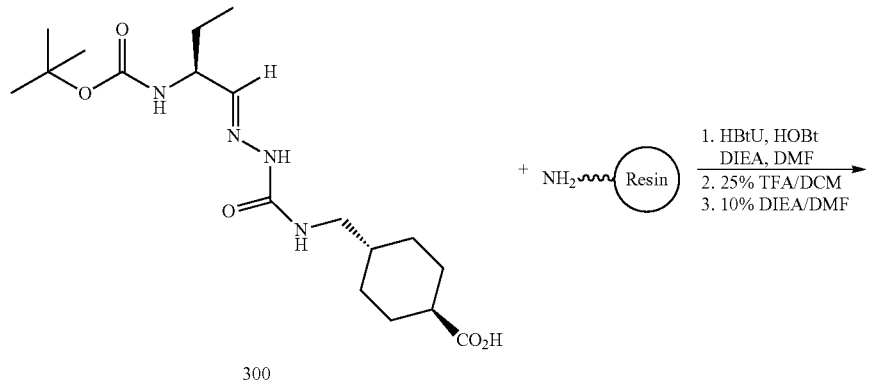
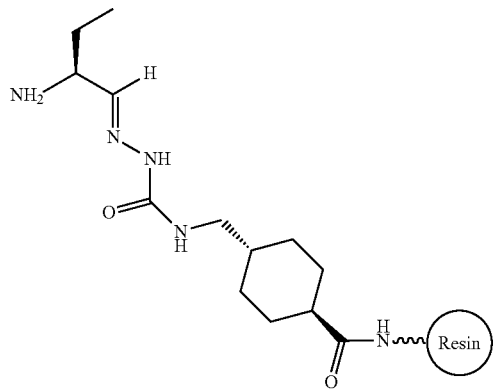
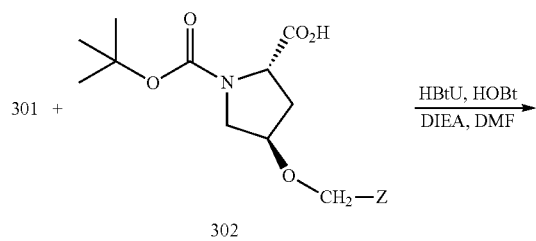

-continued

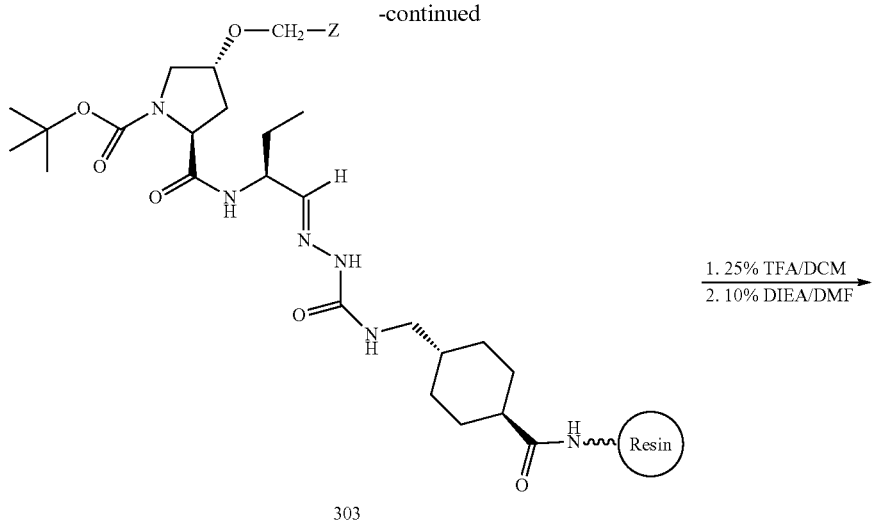
303

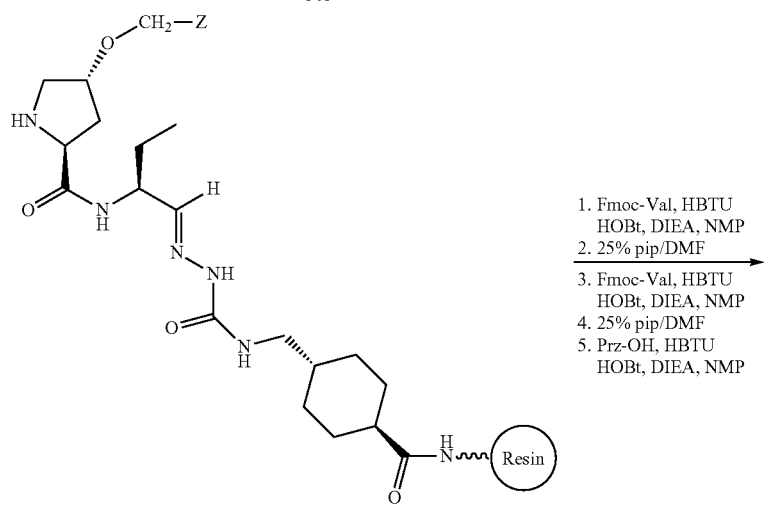
304

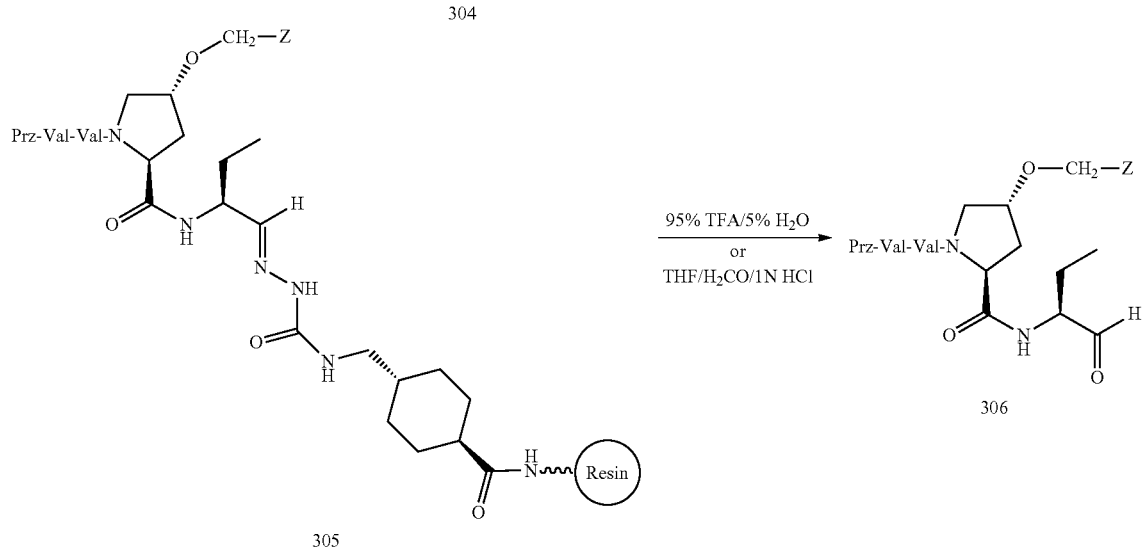
305

306

Synthesis of 301-306

Step A. Synthesis of 301.
4-Methyl Benzhydrylamine resin (1.05 mmol/g, 20.0 g) was placed in a sintered glass funnel and washed with dimethylformamide (3×75 mL), 10% (v/v) diisopropylethylamine (DIEA) in dimethylformamide (2×75 mL) and finally with dimethylformamide (4×75 mL). Sufficient dimethylformamide was added to the resin to obtain a slurry followed by 300 (8.0 g, 20.8 mmol, prepared from (2S) 2-(t-Butyloxycarbonylamino)-butyraldehyde according to A. M. Murphy et. al. *J. Am. Chem. Soc.*, 114, 3156-3157 (1992)), 1-hydroxybenzotriazole hydrate (HOBT.H$_2$O; 3.22 g, 21.0 mmol), O-benzotriazole-N,N,N',N'-tetramethyluronium hexafluorophosphate (HBTU; 8.0 g, 21.0 mmol), and DIEA (11.0 mL, 63 mmol). The reaction mixture was agitated overnight at room temperature using a wrist arm shaker. The resin was isolated on a sintered glass funnel by suction filtration and washed with dimethylformamide (3×75 mL). Unreacted amine groups were then capped by reacting the resin with 20% (v/v) acetic anhydride/dimethylformamide (2×50 mL) directly in the funnel (10 min/wash). The resin was washed with dimethylformamide (3×75 mL) and dichloromethane (3×75 mL) prior to drying overnight in vacuo to yield resin 300a (26.3 g, 81% yield).

The t-Boc protecting group was removed from resin 300a using the Advanced ChemTech 396 Multiple Peptide synthesizer by the following procedure. Resin 300a (0.05 mmol) was swelled by washing with dichloromethane (3×1 mL) followed by cleavage of the t-Boc protecting group with 50% (v/v) TFA/dichloromethane (1.0 mL) for 10 min (with shaking) followed by fresh reagent (1 mL) for 30 min. The resin was then washed with dichloromethane (3×1 ml), followed by DMF (3×1 mL), then 10% DIEA/dimethylformamide (v/v) (2×1 mL), and finally with N-methylpyrrolidone (3×1 mL) to yield resin 301.

Step B. Synthesis of 303.

This compound was prepared from resin 301 (0.05 mmol) using an Advanced ChemTech 396 Multiple Peptide synthesizer. Resin 301 was acylated with a solution of 0.4M 302 and 0.4M HOBT in N-methylpyrrolidone (0.5 mL), a solution of 0.4M HBTU in N-methylpyrrolidone (0.5 mL) and a solution of 1.6M DIEA in N-methylpyrrolidone (0.35 mL) and the reaction was shaken for 4 hr at room temperature. The coupling reaction was repeated. The resin was then washed with dimethylformamide (3×1 ml), followed by dichloromethane (3×1 mL) to yield resin 303.

Step C. Synthesis of 305.

The synthesis of the resin-bound compound was completed using an Advanced ChemTech 396 Multiple Peptide synthesizer. Resin 303 was washed with dichloromethane (3×1 mL) followed by cleavage of the t-Boc protecting group with 50% (v/v) TFA/dichloromethane (1.0 mL) for 10 min (with shaking) followed by fresh reagent (1 mL) for 30 min. The resin was then washed with dichloromethane (3×1 ml), followed by DMF (3×1 mL), then 10% DIEA/dimethylformamide (v/v) (2×1 mL), and finally with N-methypyrrolidone (3×1 mL) to yield resin 304. This resin was then acylated with a solution of 0.4M Fmoc-Valine and 0.4M HOBT in N-methylpyrrolidone (0.5 mL), a solution of 0.4M HBTU in N-methylpyrrolidone (0.5 mL) and a solution of 1.6M DIEA in N-methylpyrrolidone (0.35 mL) and the reaction was shaken for 4 hr at room temperature. The coupling reaction was repeated. The automated cycles consisted of: (1) a resin wash with dimethylformamide (3×1 mL); (2) deprotection with 25% (v/v) piperidine in dimethylformamide (1 mL) for 3 min followed by fresh reagent (1 mL) for 10 min.; (3) a resin wash with dimethylformamide (3×1 mL) and N-methylpyrrolidone (3×1 mL) prior to coupling as described above. Fmoc-Valine and Pyrazine-2-carboxylic acid were coupled in this manner.

Step D. Synthesis of 306.

Prior to cleavage, the resin was washed with 1:1 dichloromethane/methanol (3×1 mL) and then dried in vacuo. The aldehyde was cleaved from the resin by treatment with either 95% TFA/5% H$_2$O (v/v, 1.5 mL) for 30 min at room temperature or by treatment with tetrahydrofuran/30% formalin/1N HCl 9:1:1 (v:v:v) for 1 hr at room temperature. After washing the resin with cleavage reagent (1 mL), the combined filtrates were diluted with water and lyophilized to obtain crude 306 as a white powder. The compound was purified by semi-prep RP-HPLC with a Waters DeltaPak 300 Å C18 column (15μ, 30×300 mm) eluting with a linear acetonitrile gradient containing 0.1% TFA (v/v) over 45 min at 20 mL/min. Fractions containing the desired product were pooled and lyophilized to provide 306.

Example 3

Compounds 27-29 (Table 1) were prepared as described in scheme 2.

SCHEME 2

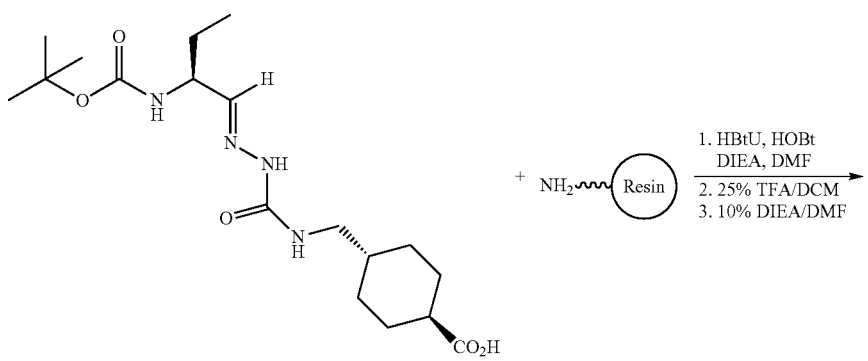

300

-continued
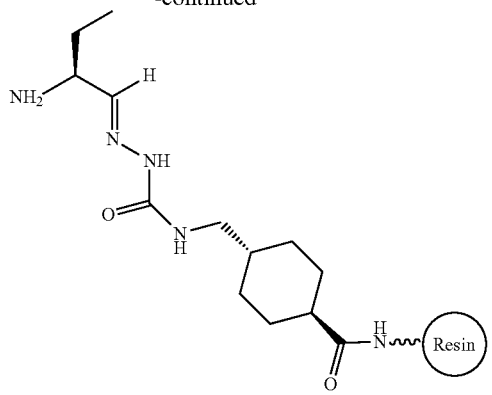
301
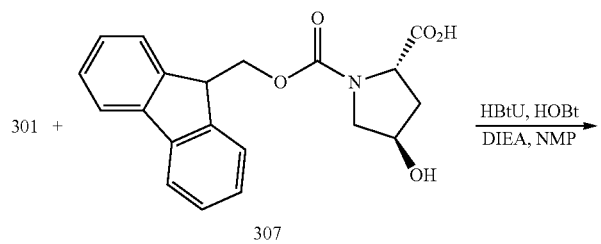
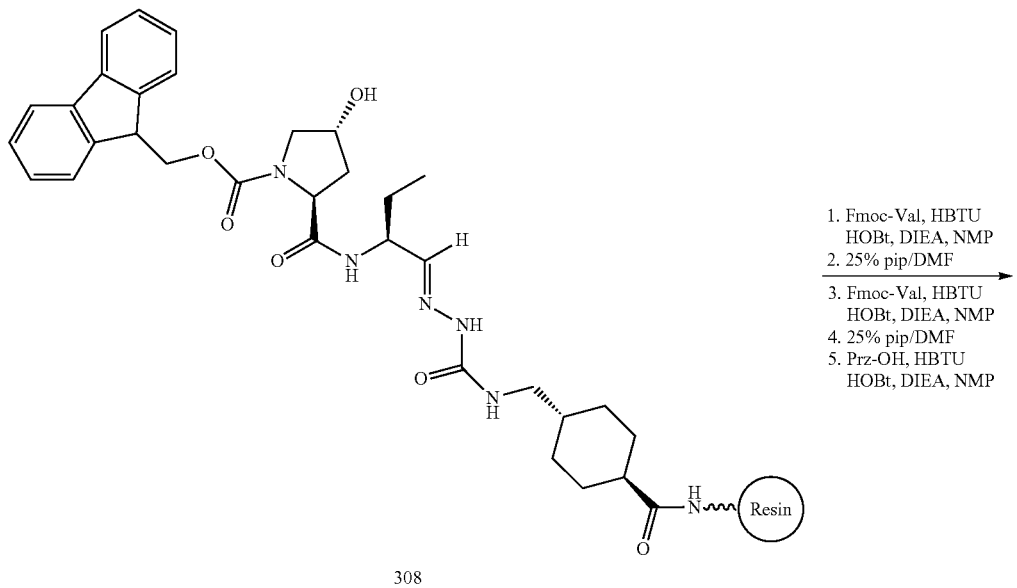
308
1. Fmoc-Val, HBTU
   HOBt, DIEA, NMP
2. 25% pip/DMF
3. Fmoc-Val, HBTU
   HOBt, DIEA, NMP
4. 25% pip/DMF
5. Prz-OH, HBTU
   HOBt, DIEA, NMP -continued

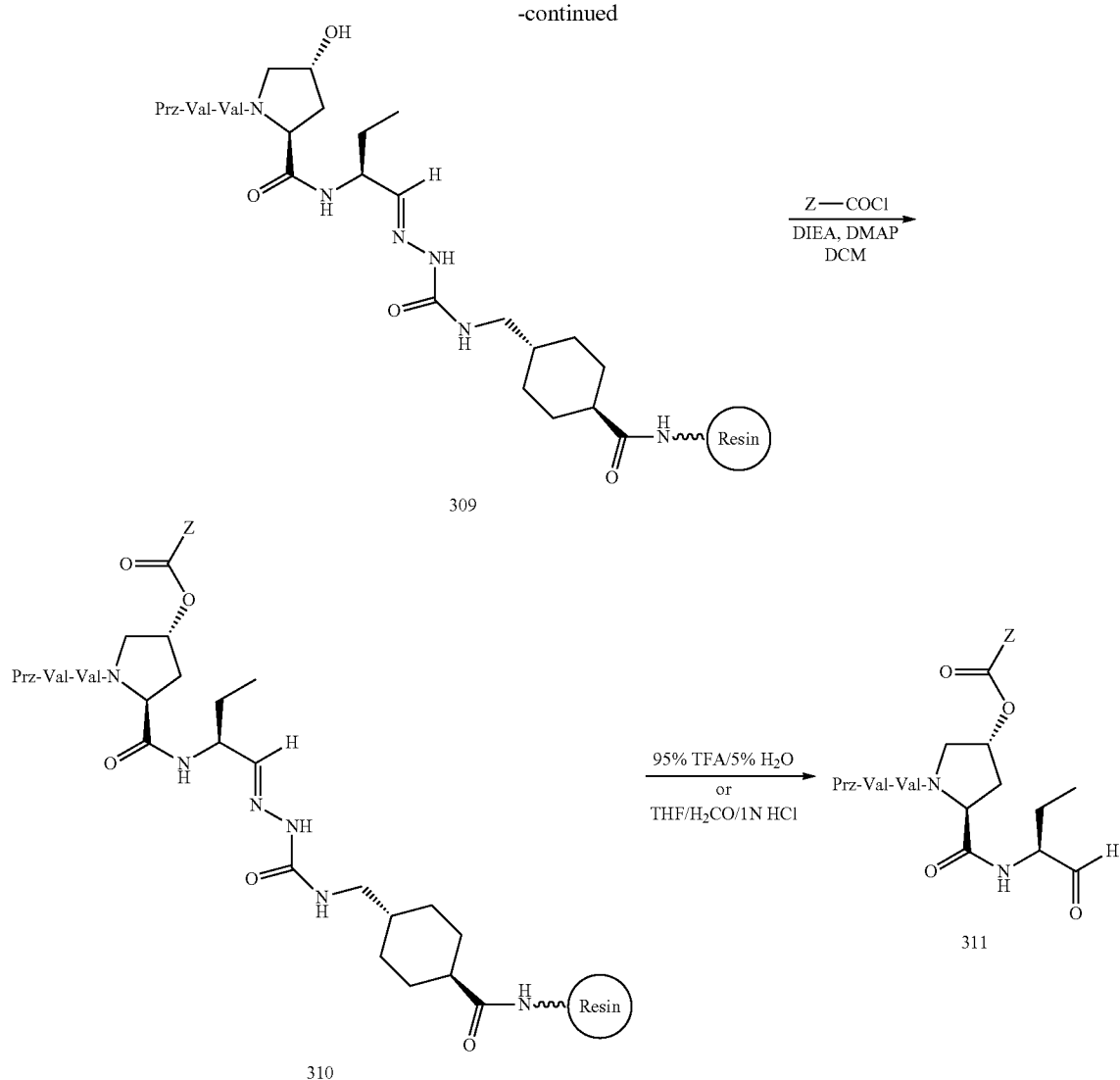

Step A. Synthesis of 301.
See Step A, Scheme 1 methodology.
Step B. Synthesis of 308.
Resin 301 (6.0 g, 0.65 mmol/g, 3.9 mmol) was swelled in a sintered glass funnel by washing with dichloromethane (3×50 mL). The Boc protecting group was then cleaved with 50% (v/v) TFA/dichloromethane (50 mL) for 10 min (intermittent stirring) and then for 30 min with fresh reagent (50 ml). The resin was then washed with dichloromethane (3×50 ml), dimethylformamide (2×50 mL), 10% DIEA/dimethylformamide (v/v) (2×50 mL), and finally N-methylpyrrolidone (3×50 mL). After transferring the resin to a 100 mL flask, N-methylpyrrolidone was added to obtain a slurry followed by 307 (2.83 g, 8.0 mmol), HOBT.H$_2$O (1.22 g, 8.0 mmol), HBTU (3.03 g, 8.0 mmol) and DIEA (4.2 mL, 24 mmol). The reaction mixture was agitated overnight at room temperature using a wrist arm shaker. The resin work-up and capping with 20% (v/v) acetic anhydride in dimethylformamide were performed as described for 301 to yield 308 (6.86 g, quantitative yield).
Step C. Synthesis of 309.
This compound was prepared from resin 308 (0.15 mmol) using a Tecan CombiTec synthesizer. Resin 308 (0.076 mmol) was washed with dimethylformamide (3×2 mL), deprotected with 25% (v/v) piperidine in dimethylformamide (2.5 mL) for 5 min followed by fresh reagent (2 mL) for 20 min. The resin was washed with dimethylformamide (3×2.5 mL) and N-methylpyrrolidone (3×2.5 mL) prior to acylation with a solution of 0.4M Fmoc-Valine and 0.4M HOBT in N-methylpyrrolidone (0.8 mL), a solution of 0.4M HBTU in N-methylpyrrolidone (0.8 mL) and a solution of 1.6M DIEA in N-methylpyrrolidone (0.6 mL) and the reaction was shaken for 8 hr at room temperature. The coupling reaction was repeated. The deprotection and coupling procedures were repeated to add the second Valine residue and to add the final pyrazine-2-carboxylic acid residue. The resin was then washed with dichloromethane (3×2.5 ml) to yield resin 309.

Step D. Synthesis of 310.
To resin 309 was added 1:1 pyridine/dichloromethane (v/v) (1 mL), 0.8M dimethylaminopyridine in dimethylformamide (0.2 mL), and a solution of 0.2M Z-COCl in dichloromethane (1.5 mL) and the reaction was shaken for 8 hr at room temperature. The acylation reaction was repeated. The resin was washed with dichloromethane (3×2.5 mL), dimethylformamide (3×2.5 mL), dichloromethane (3×2.5 mL), and finally with 1:1 dichloromethane/methanol (3×2.5 mL) to yield resin 310.

Step E. Synthesis of 311.

Prior to cleavage, the resin was washed with 1:1 dichloromethane/methanol (3×1 mL) and then dried in vacuo. The aldehyde was cleaved from the resin by treatment with tetrahydrofuran/formalin/acetic acid/1N HCl 5:1:1:0.1 (v:v:v:v) for 1 hr at room temperature. After washing the resin with cleavage reagent (1 mL), the combined filtrates were diluted with water and lyophilized to obtain crude 311 as a white powder. The compound was purified by semi-prep RP-HPLC with a Waters DeltaPak 300 Å C18 column (15μ, 30×300 mm) eluting with a linear acetonitrile gradient containing 0.1% TFA (v/v) over 45 min at 20 mL/min. Fractions containing the desired product were pooled and lyophilized to provide 311.

Example 4

Compounds 30-56 (Table 1) were prepared as described in scheme 3.

SCHEME 3

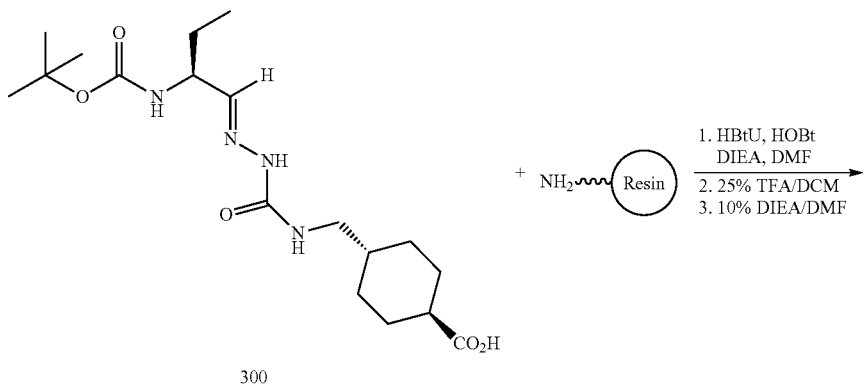

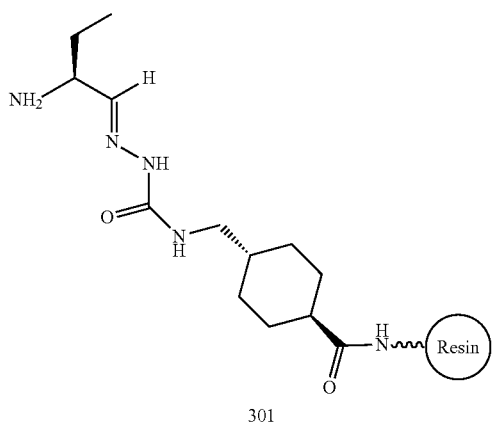

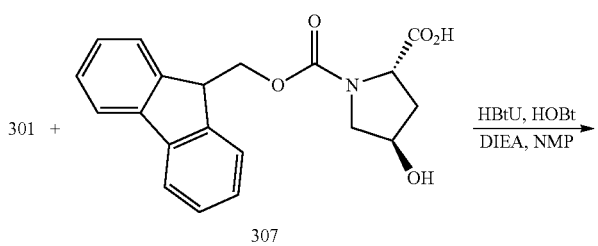

-continued
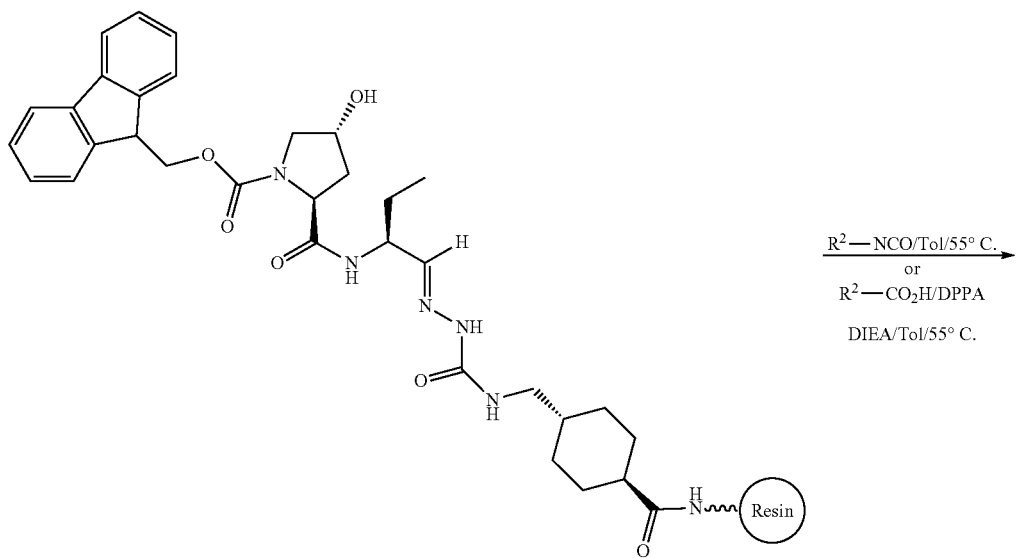
308
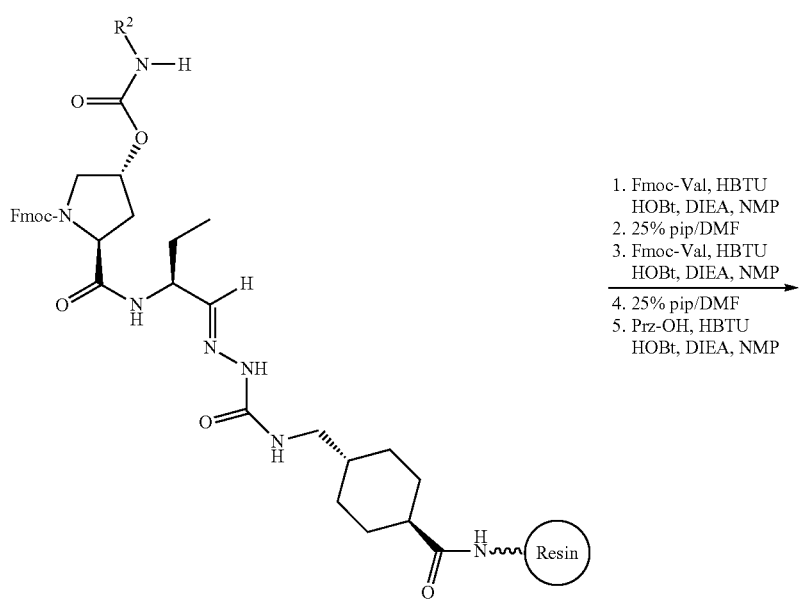
312

-continued

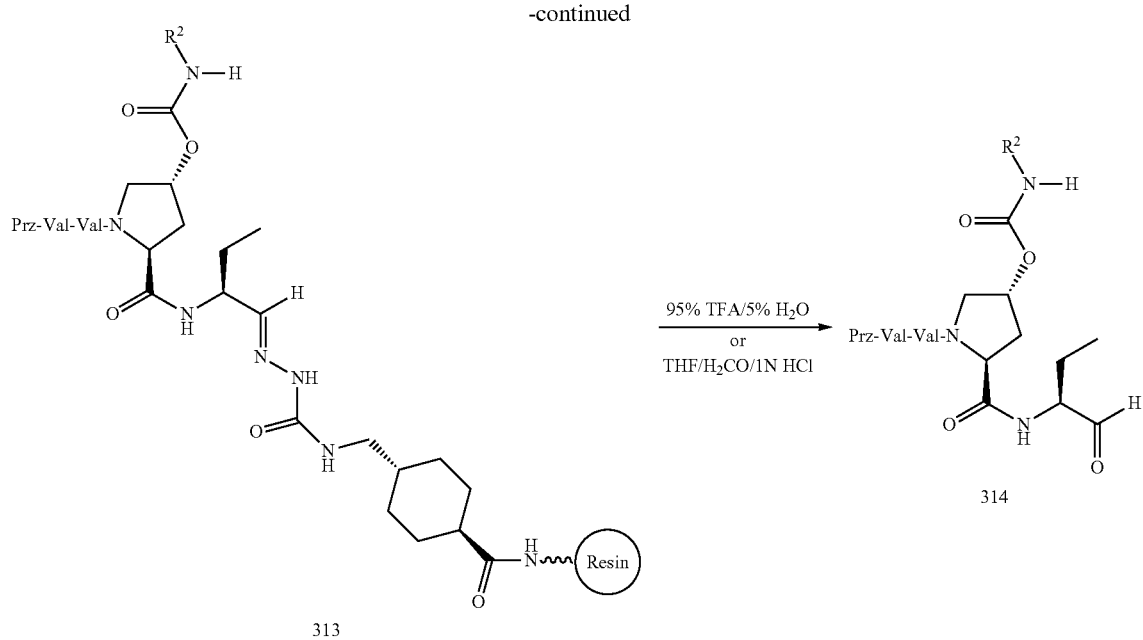
313

95% TFA/5% H₂O
or
THF/H₂CO/1N HCl

314

Step A. Synthesis of 301.
See Step A, Scheme 1 methodology.
Step B. Synthesis of 308.
See Step B, Scheme 2 methodology.
Step C.
Synthesis of 312. This compound was prepared from resin 308 (0.15 mmol) using a Tecan CombiTec synthesizer. Resin 308 was washed with toluene (3×2.5 mL) and then suspended in toluene (1.0 mL). To this was added either a solution of 0.8M R₃ δ-isocyanate in toluene (1.0 mL) followed by 0.8M DIEA in toluene (1.0 mL) or a solution of 0.8M R₃ δ-carboxylic acid with 0.8M DIEA in toluene (1.0 mL) followed by 0.8M diphenylphosphorylazide in toluene (1.0 mL). The reaction was shaken for 8 hr at 55° C. The resin was then washed with toluene (3×2.5 ml) and dimethylformamide (4×2.5 mL) to yield resin 312.
Step D. Synthesis of 313.
See Step D, Scheme 2 methodology.
Step E. Synthesis of 314.
See Step E, Scheme 2 methodology.

Example 5

Compounds 57-70 (Table 1) were prepared as described in scheme 4.

SCHEME 4

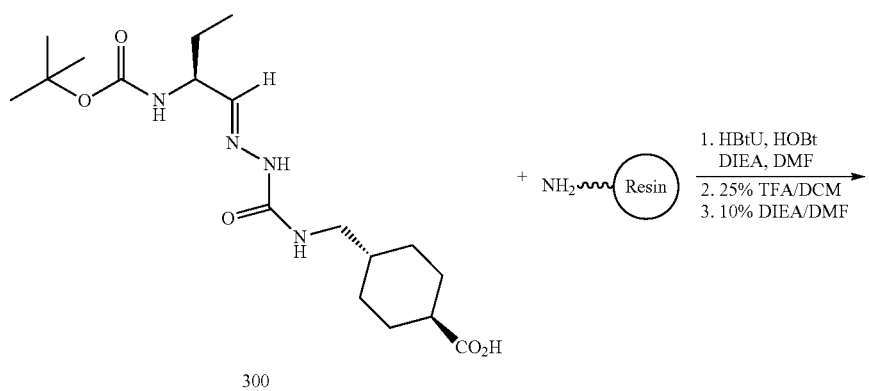
300

1. HBtU, HOBt DIEA, DMF
2. 25% TFA/DCM
3. 10% DIEA/DMF

-continued
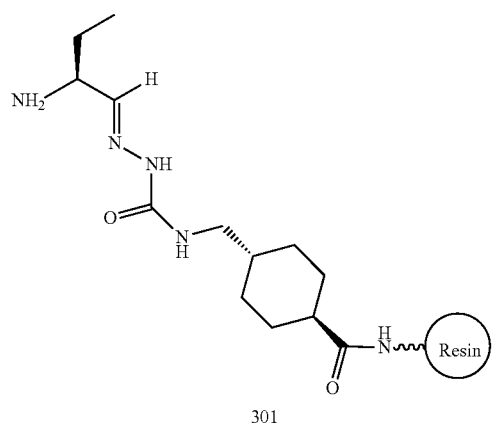
301
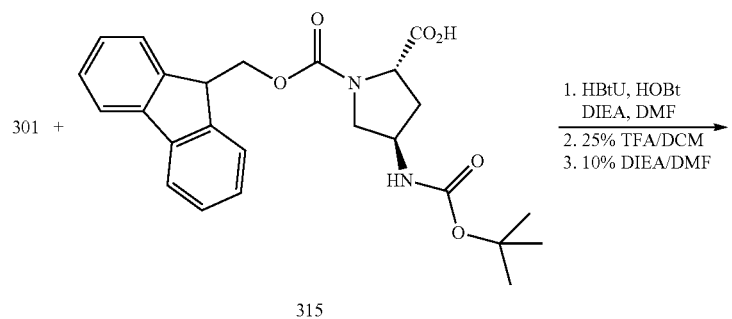
315
1. HBtU, HOBt DIEA, DMF
2. 25% TFA/DCM
3. 10% DIEA/DMF
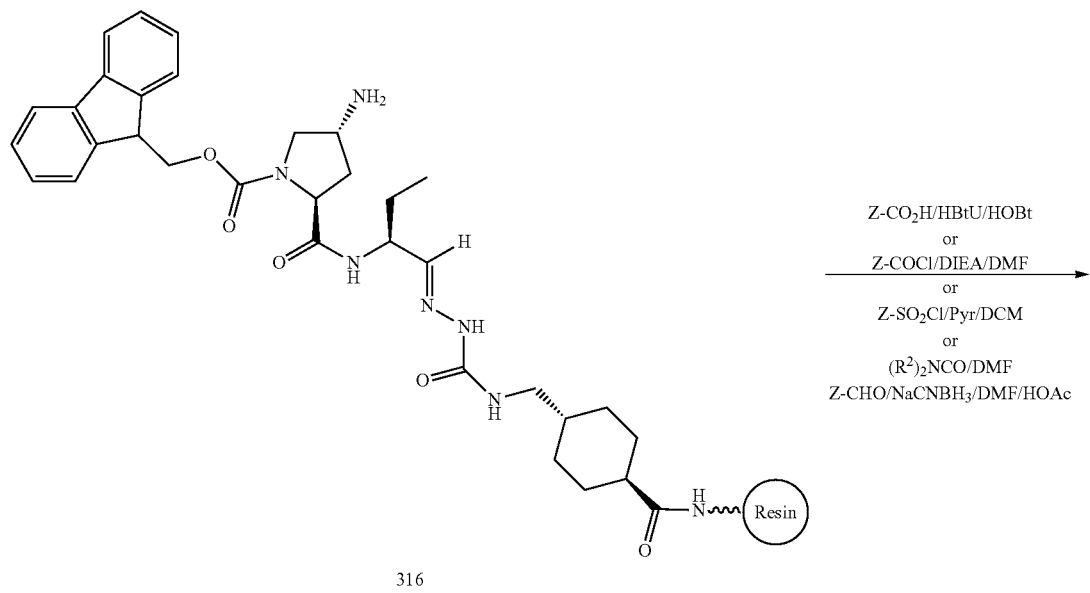
316
Z-CO₂H/HBtU/HOBt
or
Z-COCl/DIEA/DMF
or
Z-SO₂Cl/Pyr/DCM
or
(R²)₂NCO/DMF
Z-CHO/NaCNBH₃/DMF/HOAc

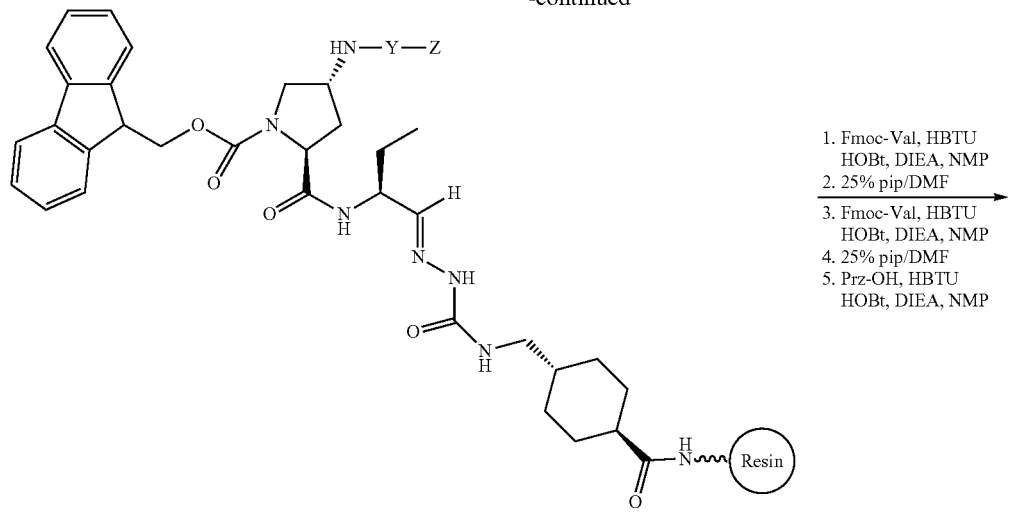

317a-e

1. Fmoc-Val, HBTU
   HOBt, DIEA, NMP
2. 25% pip/DMF
3. Fmoc-Val, HBTU
   HOBt, DIEA, NMP
4. 25% pip/DMF
5. Prz-OH, HBTU
   HOBt, DIEA, NMP

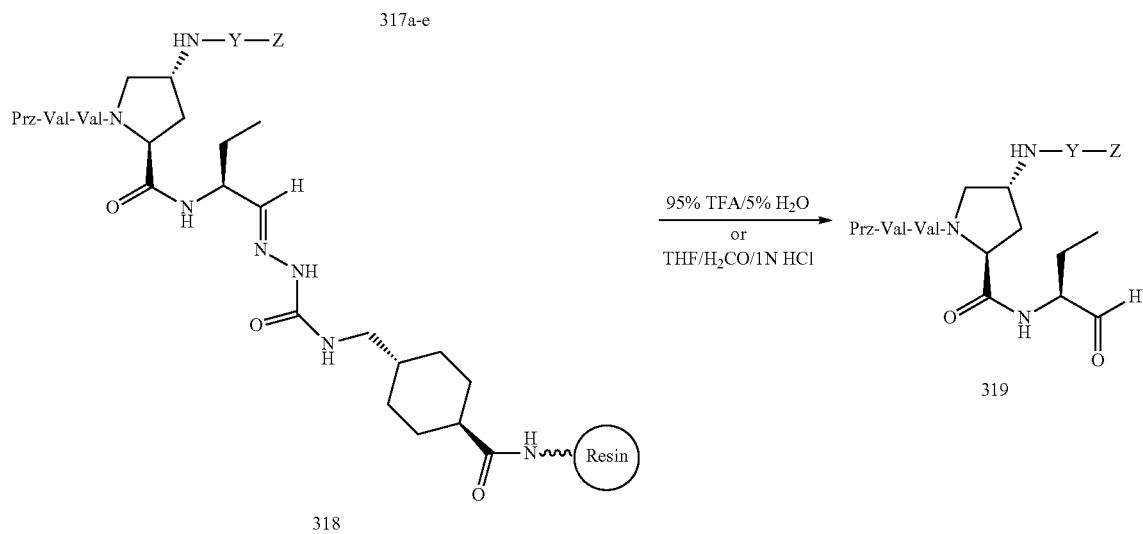

318

95% TFA/5% H$_2$O
or
THF/H$_2$CO/1N HCl

319

Step A. Synthesis of 301.

See Step A, Scheme 1 methodology.

Step B. Synthesis of 316.

This compound was prepared from resin 301 (0.05 mmol) using an Advanced ChemTech 396 Multiple Peptide synthesizer. Resin 301 was acylated with a solution of 0.4M 315 and 0.4M HOBT in N-methylpyrrolidone (0.5 mL), a solution of 0.4M HBTU in N-methylpyrrolidone (0.5 mL) and a solution of 1.6M DIEA in N-methylpyrrolidone (0.35 mL) and the reaction was shaken for 4 hr at room temperature. The coupling reaction was repeated. The resin was then washed with dimethylformamide (3×1 ml), followed by dichloromethane (3×1 mL). The Boc protecting group was then cleaved with 50% (v/v) TFA/dichloromethane (1.0 mL) for 10 min with vortexing and then for 30 min with fresh reagent (1.0 ml). The resin was then washed with dichloromethane (3×1.0 ml), dimethylformamide (2×1.0 mL), 10% DIEA/dimethylformamide (v/v) (2×1.0 mL), dimethylformamide (3×1.0 ml), and finally dichloromethane (3×1.0 mL) to yield 316.

Step C. Synthesis of 317a.

Resin 316 was acylated with a solution of 0.4M Z-CO$_2$H and 0.4M HOBT in N-methylpyrrolidone (0.5 mL), a solution of 0.4M HBTU in N-methylpyrrolidone (0.5 mL) and a solution of 1.6M DIEA in N-methylpyrrolidone (0.35 mL) and the reaction was shaken for 4 hr at room temperature. The coupling reaction was repeated. The resin was then washed with dimethylformamide (3×1 ml) to yield resin 317a.

Step C. Synthesis of 317b.

Resin 316 was acylated with 0.5M Z-COCl in dimethylformamide (1 mL) and 1.6M DIEA in N-methylpyrrolidone (0.35 mL) for 2 hr at room temperature. The acylation step was repeated. The resin was washed with dimethylformamide (3×2.5 mL) to yield resin 317b.

Step C. Synthesis of 317c.

Resin 316 was reacted with 1.0M Z-sulfonyl chloride in dichloromethane (0.5 mL) and 1M pyridine in dichloromethane (0.60 mL) for 4 hr at room temperature The reaction was repeated. The resin was washed with dichloromethane (3×1.0 mL), and then dimethylformamide (3×1.0 mL) to yield resin 317c.

Step C. Synthesis of 317d.

Resin 316 was reacted with 0.5M Z-isocyanate in dimethylformamide (1.2 mL) for 8 hr at room temperature The reaction was repeated. The resin was washed with dimethylformamide (3×1.0 mL) to yield resin 317d.

Step C. Synthesis of 317e.

Resin 316 was reacted with 0.5M Z-CHO in dimethylformamide (1.2 mL) in the presence of acetic acid (0.1 mL) and sodium cyanoborohydride (200 mg) for 4 hr at room temperature. The reaction was repeated. The resin was washed with dimethylformamide (3×1.0 mL) to yield resin 317e.

Step D. Synthesis of 318.

The synthesis of the resin-bound compound was completed using an Advanced ChemTech 396 Multiple Peptide synthesizer. The automated cycles described in Step C, Scheme 1, were used to add Fmoc-Valine, followed by another Fmoc-Valine, and finally pyrazine-2-carboxylic acid.

Step E. Synthesis of 319.

See Step E, Scheme 2 methodology.

Example 6

Compounds 81-100 and 127-142 (Tables 3 and 4) were prepared as described in scheme 5.

SCHEME 5

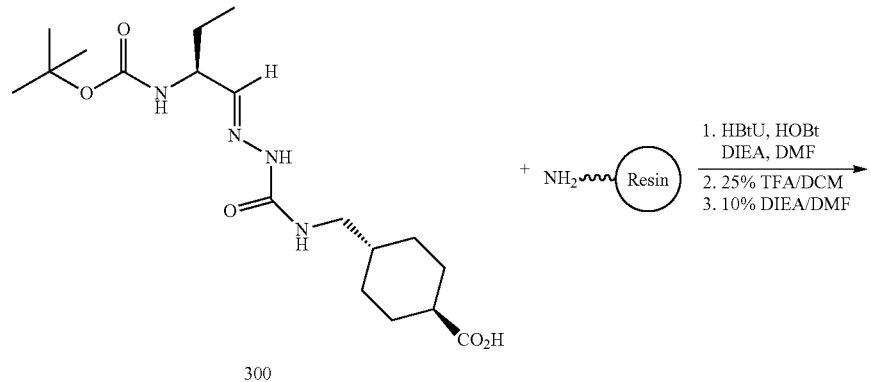

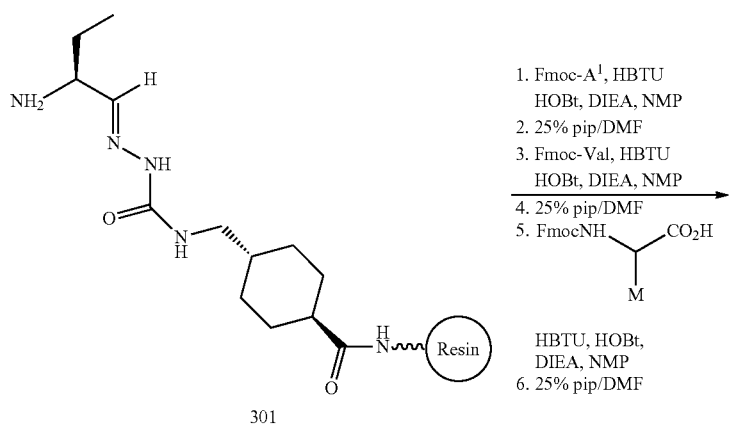

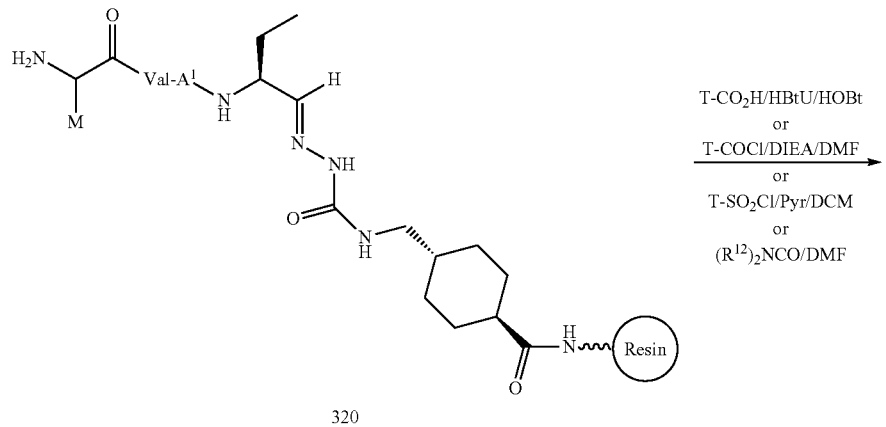

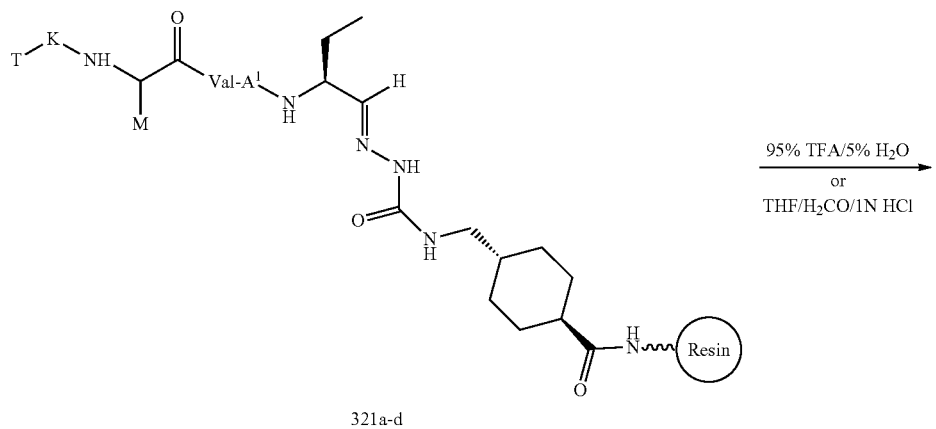

321a-d

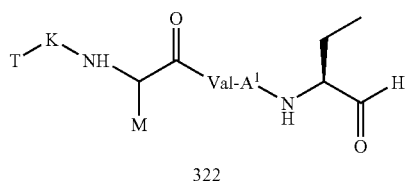

322

Step A. Synthesis of 301.
See Step A, Scheme 1 methodology.
Step B. Synthesis of 320.
The synthesis of the resin-bound compound was accomplished using an Advanced ChemTech 396 Multiple Peptide synthesizer starting with resin 165 (0.05 mmol). The automated cycles described in Step C, Scheme 1, were used to add Fmoc-$A^1$, followed by Fmoc-valine and finally a terminal Fmoc-amino acid. The Fmoc group was removed as previously described with 25% piperidine/dimethylformamide (v:v) to yield resin 166.
Step C. Synthesis of 321a.
Resin 320 was acylated with a solution of 0.4M T-$CO_2$H and 0.4M HOBT in N-methylpyrrolidone (0.5 mL), a solution of 0.4M HBTU in N-methylpyrrolidone (0.5 mL) and a solution of 1.6M DIEA in N-methylpyrrolidone (0.35 mL) and the reaction was shaken for 4 hr at room temperature. The coupling reaction was repeated. The resin was then washed with dimethylformamide (3×1 ml), dichloromethane (3×1.0 mL), and 1:1 dichloromethane/methanol (v/v) (3×1 mL) to yield resin 321a.
Step C. Synthesis of 321b.
Resin 320 was acylated with 0.5M T-COCl in dimethylformamide (1 mL) and 1.6M DIEA in N-methylpyrrolidone (0.35 mL) for 2 hr at room temperature. The acylation step was repeated. The resin was then washed with dimethylformamide (3×1 ml), dichloromethane (3×1.0 mL), and 1:1 dichloromethane/methanol (v/v) (3×1 mL) to yield resin 321b.
Step C. Synthesis of 321c.
Resin 320 was reacted with 1.0M T-sulfonyl chloride in dichloromethane (0.5 mL) and 1M pyridine in dichloromethane (0.60 mL) for 4 hr at room temperature The reaction was repeated. The resin was then washed with dimethylformamide (3×1.0 ml), dichloromethane (3×1.0 mL), and 1:1 dichloromethane/methanol (v/v) (3×1.0 mL) to yield resin 303c.
Step C. Synthesis of 321d.
Resin 320 was reacted with 0.5M T-isocyanate in dimethylformamide (1.2 mL) for 8 hr at room temperature The reaction was repeated. The resin was then washed with dimethylformamide (3×1.0 ml), dichloromethane (3×1.0 mL), and 1:1 dichloromethane/methanol (v/v) (3×1.0 mL) to yield resin 321d.
Step D. Synthesis of 322.
The aldehyde was cleaved from the resin and globally deprotected by treatment with 95% TFA/5% $H_2O$ (v/v, 1.5 mL) for 45 min at room temperature. After washing the resin with fresh cleavage reagent (1 mL), the combined filtrates were added to cold 1:1 ether:pentane (12 mL) and the resulting precipitate was isolated by centrifugation and decantation. The resulting pellet was dissolved in 10% acetonitrile/90% $H_2O$/0.1% TFA (15 mL) and lyophilized to obtain crude 322 as a white powder. The compound was purified by semi-prep RP-HPLC with a Waters DeltaPak 300 Å C18 column (15μ, 30×300 mm) eluting with a linear acetonitrile gradient containing 0.1% TFA (v/v) over 45 min at 20 mL/min. Fractions containing the desired product were pooled and lyophilized to provide 322.

Example 7

Compounds 143-197 (Table 6) were prepared as described in scheme 6.

SCHEME 6
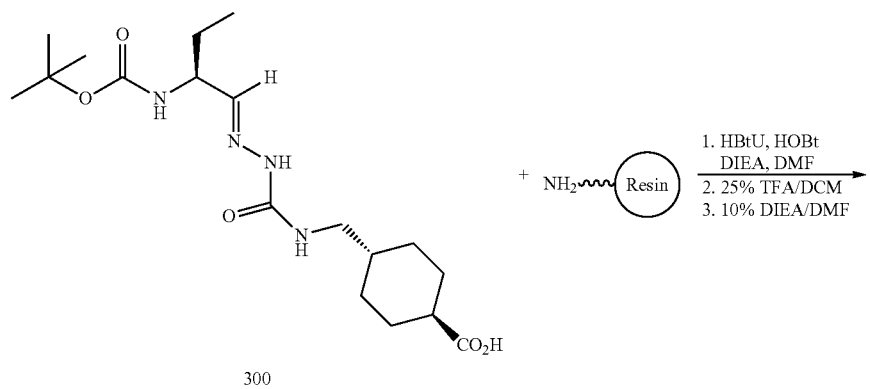
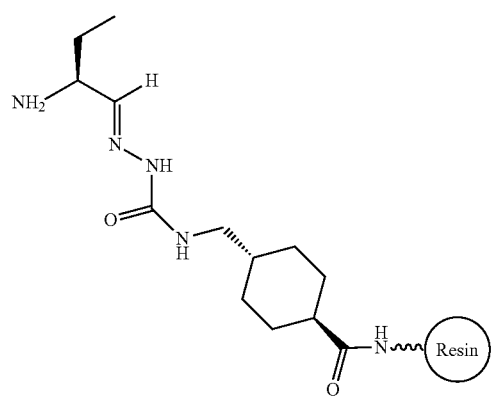
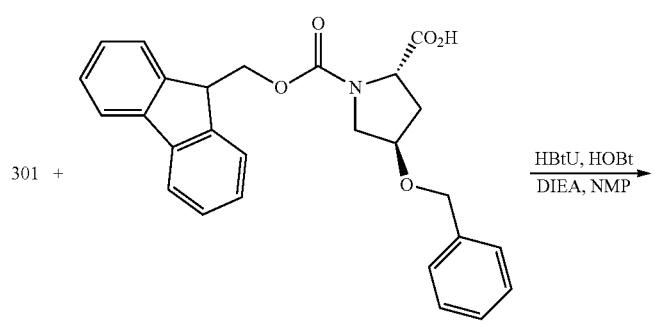

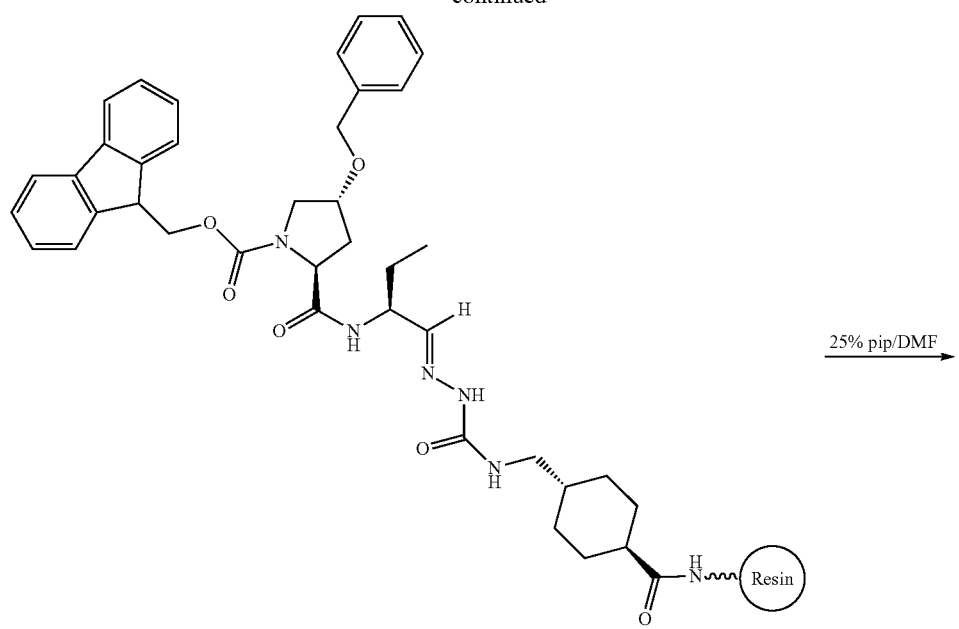
324
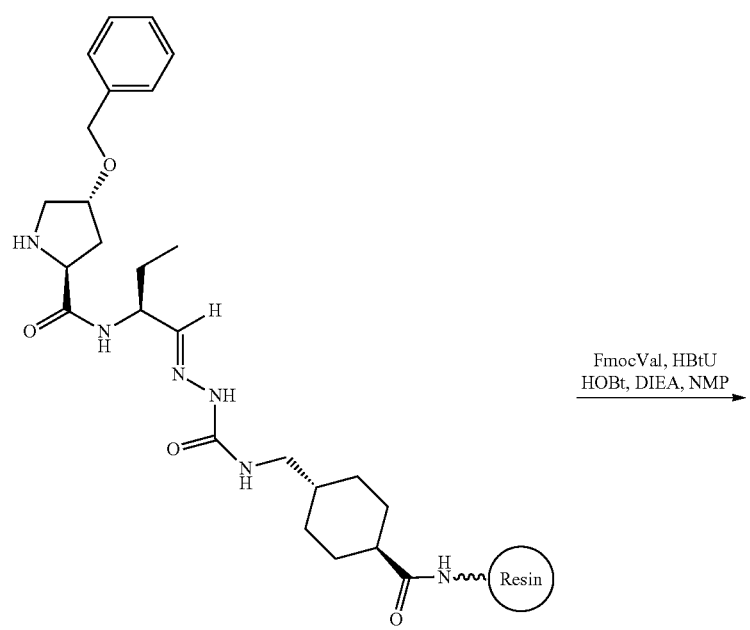
325

-continued
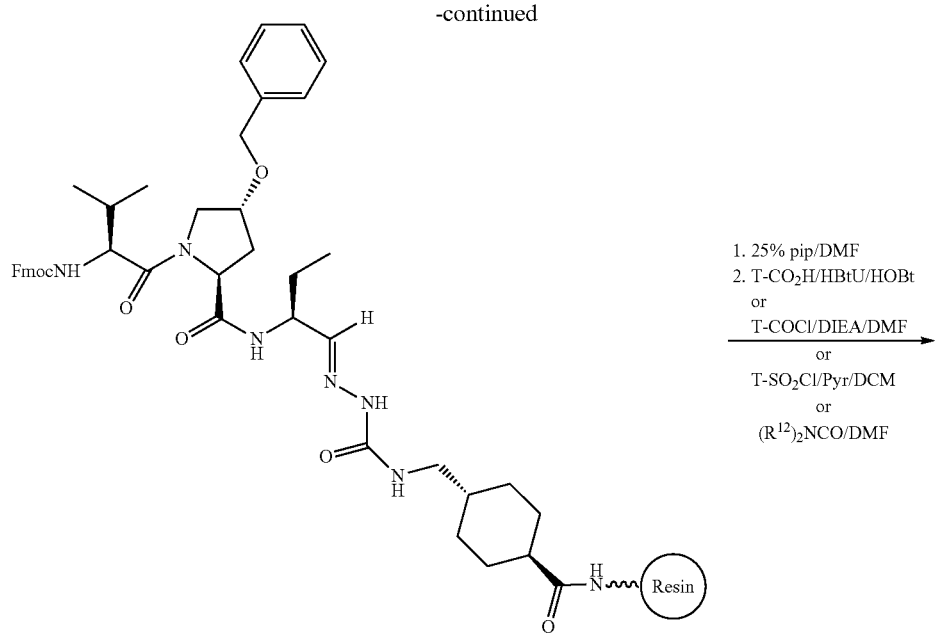
326
1. 25% pip/DMF
2. T-CO₂H/HBtU/HOBt
   or
   T-COCl/DIEA/DMF
   or
   T-SO₂Cl/Pyr/DCM
   or
   (R$^{12}$)₂NCO/DMF
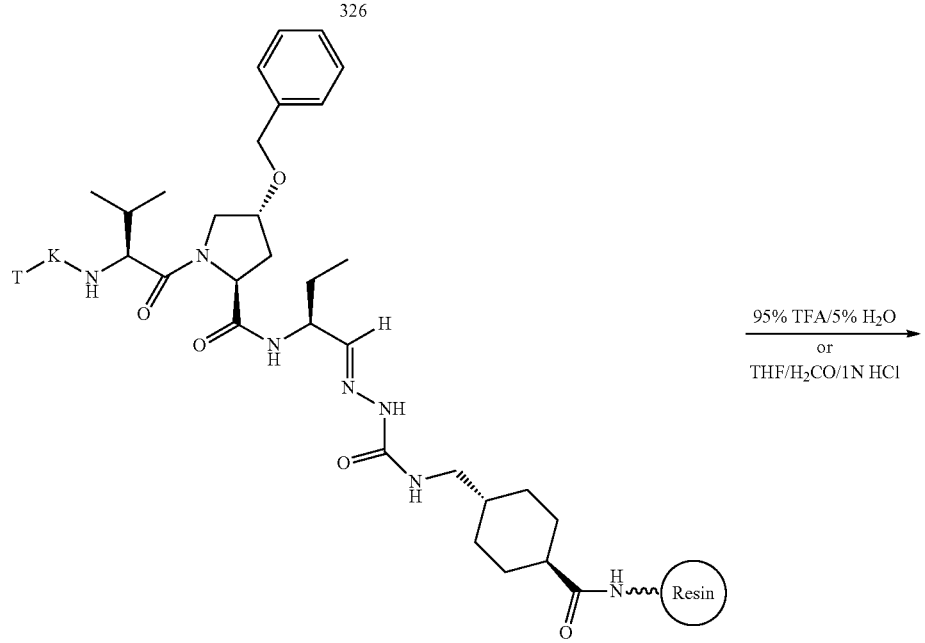
327a-d
95% TFA/5% H₂O
or
THF/H₂CO/1N HCl
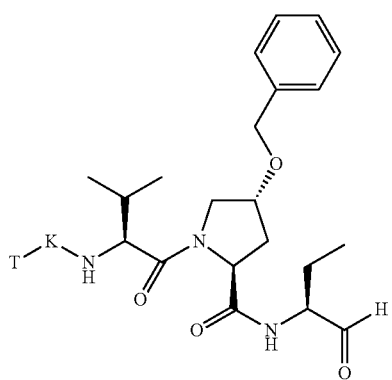
328

Step A. Synthesis of 301.
See Step A, Scheme 1 methodology.
Step B. Synthesis of 326.

This compound was prepared from resin 301 (0.50 mmol) using an Applied Biosystems Model 433A Peptide synthesizer. $N^\alpha$-Fmoc-protected amino acids were added sequentially to resin 301 with standard coupling cycles using HBTU with HOBt as coupling agents in N-methylpyrrolidinone to yield resin 326.

Step C. Synthesis of 327a.

The synthesis was completed using an Advanced ChemTech 396 Multiple Peptide Synthesizer. Resin 326 (0.05 mmol) was deprotected with 25% (v/v) piperidine in dimethylformamide (1 mL) for 3 min followed by fresh reagent (1 mL) for 10 min. The resin was washed with dimethylformamide (3×1 mL) and N-methylpyrrolidone (3×1 mL). The resin was acylated with a solution of 0.4M T-$CO_2$H and 0.4M HOBT in N-methylpyrrolidone (0.5 mL), a solution of 0.4M HBTU in N-methylpyrrolidone (0.5 mL) and a solution of 1.6M DIEA in N-methylpyrrolidone (0.35 mL) and the reaction was shaken for 4 hr at room temperature. The coupling reaction was repeated. The resin was then washed with dimethylformamide (3×1 ml), dichloromethane (3×1.0 mL), and 1:1 dichloromethane/methanol (v/v) (3×1 mL) to yield resin 327a.

Step C. Synthesis of 327b.

The synthesis was completed using an Advanced ChemTech 396 Multiple Peptide Synthesizer. Resin 326 (0.05 mmol) was deprotected with 25% (v/v) piperidine in dimethylformamide (1 mL) for 3 min followed by fresh reagent (1 mL) for 10 min. The resin was washed with dimethylformamide (3×1 mL) and N-methylpyrrolidone (3×1 mL). The resin was acylated with 0.5M T-COCl in dimethylformamide (1 mL) and 1.6M DIEA in N-methylpyrrolidone (0.35 mL) for 2 hr at room temperature. The acylation step was repeated. The resin was then washed with dimethylformamide (3×1 ml), dichloromethane (3×1.0 mL), and 1:1 dichloromethane/methanol (v/v) (3×1 mL) to yield resin 327b.

Step C. Synthesis of 327c.

The synthesis was completed using an Advanced ChemTech 396 Multiple Peptide Synthesizer. Resin 326 (0.05 mmol) was deprotected with 25% (v/v) piperidine in dimethylformamide (1 mL) for 3 min followed by fresh reagent (1 mL) for 10 min. The resin was washed with dimethylformamide (3×1 mL) and dichloromethane (3×1 mL). The resin was reacted with 1.0M T-sulfonyl chloride in dichloromethane (0.5 mL) and 1M pyridine in dichloromethane (0.60 mL) for 4 hr at room temperature The reaction was repeated. The resin was then washed with dimethylformamide (3×1.0 ml), dichloromethane (3×1.0 mL), and 1:1 dichloromethane/methanol (v/v) (3×1.0 mL) to yield resin 327c.

Step C. Synthesis of 327d.

The synthesis was completed using an Advanced ChemTech 396 Multiple Peptide Synthesizer. Resin 326 (0.05 mmol) was deprotected with 25% (v/v) piperidine in dimethylformamide (1 mL) for 3 min followed by fresh reagent (1 mL) for 10 min. The resin was washed with dimethylformamide (3×1 mL). The resin was reacted with 0.5M T-isocyanate in dimethylformamide (1.2 mL) for 8 hr at room temperature The reaction was repeated. The resin was then washed with dimethylformamide (3×1.0 ml), dichloromethane (3×1.0 mL), and 1:1 dichloromethane/methanol (v/v) (3×1.0 mL) to yield resin 327d.

Step D. Synthesis of 328.
See Step D, Scheme 1 methodology.

Example 8

Compounds 79-80 and 101-123 (Tables 2, 3 and 4) were prepared as described in scheme 7.

SCHEME 7

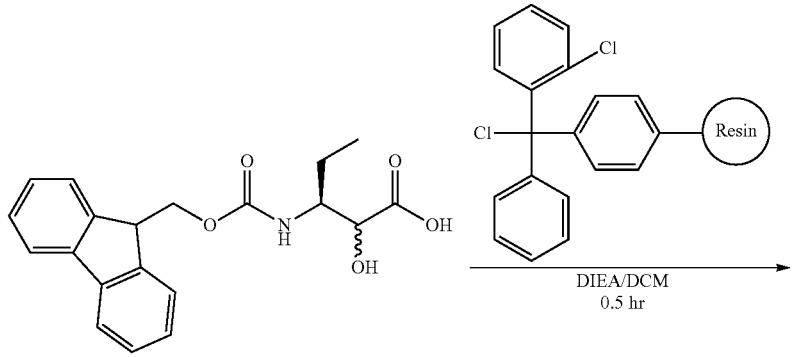

329

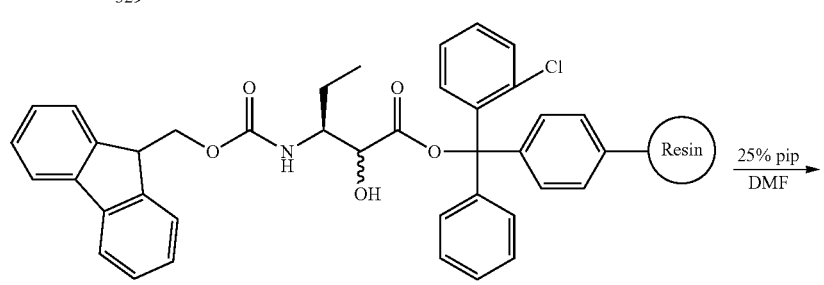

330

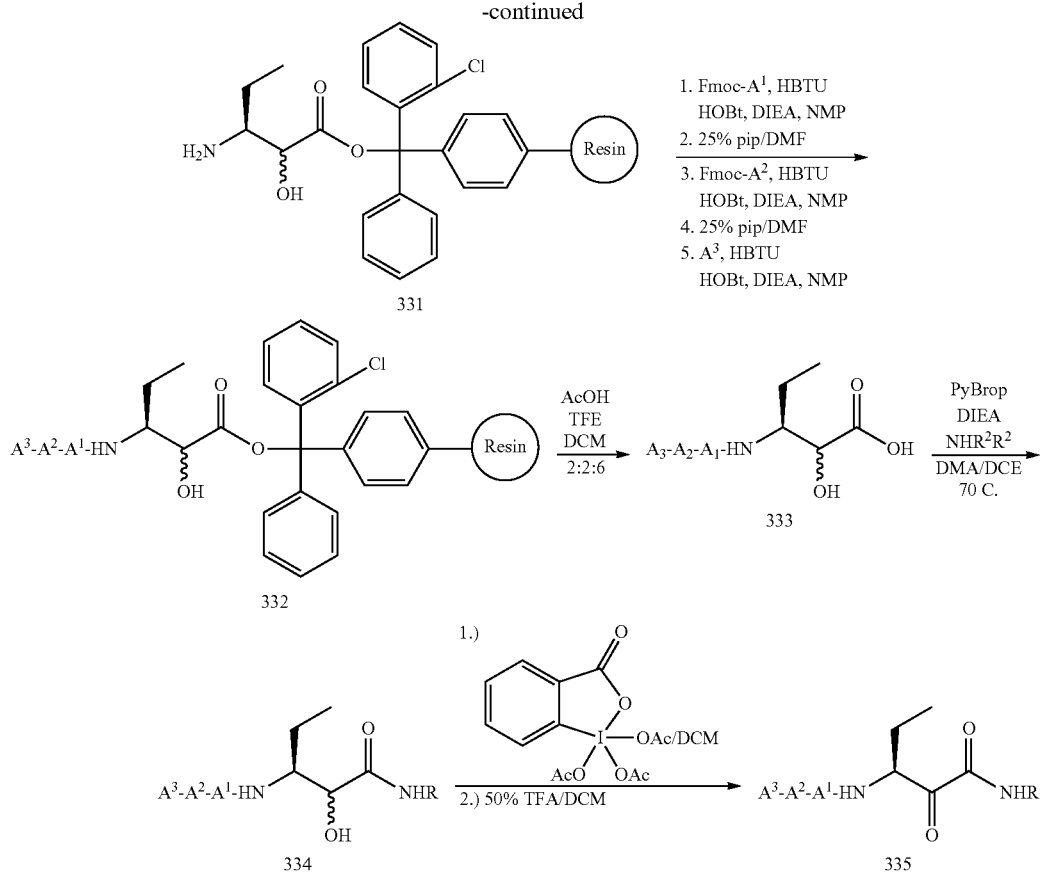

Step A. Synthesis of 330.

2-Chlorochlorotrityl resin (2.2 mmol/g, 1.69 g) was reacted with 329 (0.385 g, 1.1 mmol, prepared according to S. L. Harbeson et. al. *J. Med. Chem.*, 37, 2918 (1994)) in dichloromethane in the presence of DIEA (0.47 mL, 2.7 mmol) at room temperature for 1 hour. The reaction was quenched by the addition of methanol and the resin was isolated on a sintered glass funnel by suction filtration and washed with dichloromethane (3×25 mL). The resin was dried overnight in vacuo to yield 330 (1.92 g, 0.49 meq/g).

Step B. Synthesis of 332.

The synthesis of the resin-bound compound was accomplished using an Applied Biosystems Model 433A Peptide synthesizer starting with resin 330 (0.74 mmol). The automated cycles described in Step C, Scheme 1, were used to add Fmoc-$A^1$, followed by Fmoc-$A^2$ and Fmoc-$A^3$. The Fmoc group was removed as previously described with 25% piperidine/dimethylformamide (v:v) to yield resin 332.

Step C. Synthesis of 333.

Prior to cleavage, the resin was washed with 1:1 dichloromethane/methanol (3×1 mL) and then dried in vacuo. The peptide was cleaved from the resin by treatment with acetic acid: trifluoroethanol:dichloromethane (1:1:3) for 1 hr at room temperature. After washing the resin with dichloromethane, the combined filtrates were concentrated in vacuo to obtain crude 333 as a white powder (0.48 g, 76%).

Step D. Synthesis of 335.

Compound 333 (0.05 g, 0.058 mmol) was dissolved in dimethylacetamide (1 mL) and to this was added DIEA (0.17 mmol), the appropriate amine (0.20 mmol), and PyBrop (0.12 mmol). The reaction was stirred for 2 hr at 70° C. The reaction was then diluted into $H_2O$ (8 mL) followed by centrifugation to obtain the precipitate that was dried in vacuo to obtain crude 334, which was then oxidized directly to compound 335. Crude 334 was dissolved in N-methylpyrrolidone (3 mL) and reacted with Dess-Martin periodinane (110 mg, 0.26 mmol) at room temperature over night. Saturated aqueous sodium bicarbonate (5 mL) and 10% (w:v) aqueous sodium thiosulfate (5 mL) were added to the reaction and stirred prior to addition of $H_2O$ (40 mL). The precipitate was isolated by centrifugation and the solid was dried in vacuo. When required, acid labile protecting groups were removed by treatment with 1:1 trifluoroacetic acid:dichloromethane at room temperature for 30 min. The solvent was removed in vacuo and the crude compound was purified by semi-prep RP-HPLC with a Waters DeltaPak 300 Å C18 column (15μ, 30×300 mm) eluting with a linear acetonitrile gradient containing 0.1% TFA (v/v) over 45 min at 20 mL/min. Fractions containing the desired product were pooled and lyophilized to provide 335.

Example 9

Compounds 71-78 and 124-126 were prepared from the appropriate protected peptide acids. Protected peptide acids were prepared as previously described in Scheme 7 using 2-Chloro-chlorotrityl resin. These peptide acids were then coupled to one of the following groups using standard solution phase peptide coupling methodologies. The references for preparation of these groups are also given.

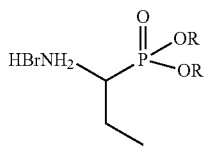

J. Oleksyszyn et. al., Synthesis, 985-986 (1979)

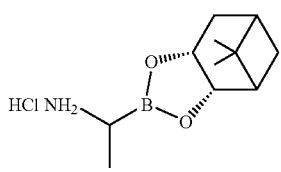

S. Elgendy et. al., *Tetrahedron*, 50, 3803-3812 (1994)

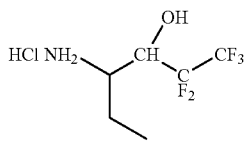

M. R. Angelestro et. al., *Tetrahedron Letters*, 33, 3265-3268 (1992)

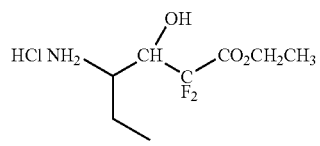

T. T. Curran, *J. Organic Chemistry*, 58, 6360-6363 (1993)

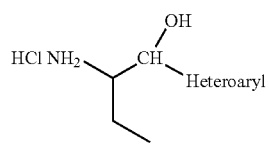

E. Edwards, et. al., *J. Medicinal Chemistry*, 38, 3972-3982 (1995).

When required, the products obtained were oxidized to the ketones using Dess Martin Periodinane as described for Scheme 7. When required, acid labile protecting groups were removed by treatment with 1:1 trifluoroacetic acid:dichloromethane at room temperature for 30 min. The solvent was removed in vacuo and the crude compound was purified by semi-prep RP-HPLC with a Waters DeltaPak 300 Å C18 column (15μ, 30×300 mm) eluting with a linear acetonitrile gradient containing 0.1% TFA (v/v) over 45 min at 20 mL/min. Fractions containing the desired product were pooled and lyophilized to provide the final products 71-78 and 124-126.

Example 10

Compound 198 was prepared by modification of the general methodology described in Example 1.

TABLE 1

Structures and analytical data - compounds 1-70.

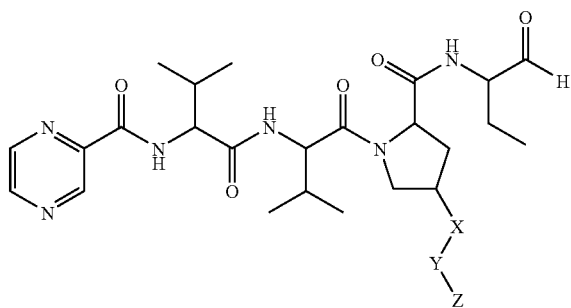

| | Z | X | Y | MS Data | HPLC |
|---|---|---|---|---|---|
| 1 | (3-phenoxyphenyl) | O | $CH_2$ | ND | 40-80%B; 5.484 min.; 6.580 min; 75:25 fast:slow |

TABLE 1-continued

Structures and analytical data - compounds 1-70.

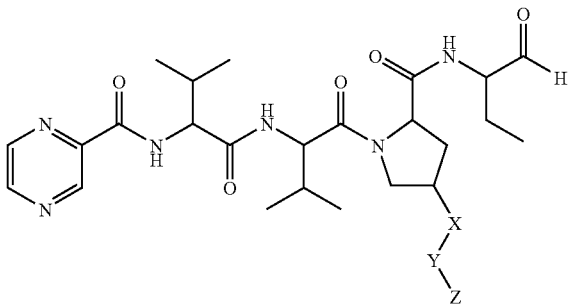

| | Z | X | Y | MS Data | HPLC |
|---|---|---|---|---|---|
| 2 | biphenyl | O | CH₂ | (M + Na) = 693.2 | 40-80%B; 5.376 min; 95% |
| 3 | 3-(phenyl)-1,2,4-oxadiazol-5-yl | O | CH₂ | (M + H) = 664.0<br>(M + Na) = 685.2 | 20-60%B; 8.527 min.; 100% |
| 4 | 3-(4-methoxyphenyl)-1,2,4-oxadiazol-5-yl | O | CH₂ | (M + Na) = 714.3 | 20-60%B; 8.885 min.; 100% |
| 5 | 3-(3,5-dimethylisoxazol-4-yl)-1,2,4-oxadiazol-5-yl | O | CH₂ | (M + H) = 682.9,<br>(M + Na) = 704.0 | 20-60%B; 7.541 min.; 95.6% |
| 6 | 3-tert-butyl-1,2,4-oxadiazol-5-yl | O | CH₂ | (M + H) = 644.0,<br>(M + Na) = 664.0 | 20-60%B; 7.822 min.; 100% |
| 7 | 5-chloro-2-(trifluoromethyl)quinolin-6-yl | O | CH₂ | (M + H) = 746.7,<br>(M + Na) = 765.7 | 40-80%B; 4.228 min.; 92% |
| 8 | 6-fluoro-4H-benzo[d][1,3]dioxin-8-yl | O | CH₂ | (M + H) = 671.5,<br>(M + Na) = 694.0 | 20-60%B; 8.554 min.; 98% |

TABLE 1-continued

Structures and analytical data - compounds 1-70.

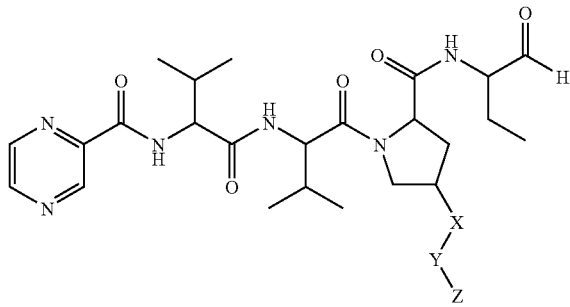

| | Z | X | Y | MS Data | HPLC |
|---|---|---|---|---|---|
| 9 | 3-(OCF3)phenyl | O | CH2 | (M + Na) = 700.9 | 40-80%B; 4.688 min.; 100% |
| 10 | 3,4-dichlorophenyl | O | CH2 | (M + Na) = 686.3 | 40-80%B; 4.630 min.; 94% |
| 11 | 2-biphenyl | O | CH2 | (M + H) = 671.1, (M + Na) = 693.2 | 40-80%B; 5.323 min.; 6.435 min.; 88:12, fast:slow |
| 12 | 3,5-dimethylisoxazol-4-yl | O | CH2 | (M + H) = 613.7, (M + Na) = 636.2 | 20-60%B; 5.696 min.; 100% |
| 13 | 6-chlorobenzo[d][1,3]dioxol-5-yl | O | CH2 | (M + Na) = 695.3 | 20-60%B; 9.046 min.; 100% |
| 14 | 5-(2-methoxyphenyl)-1,2,4-oxadiazol-3-yl | O | CH2 | (M + Na) = 714.9 | 20-60%B; 7.729 min.; 100% |
| 15 | 4-cyanophenyl | O | CH2 | (M + Na) = 642.72 | 20-60%B; 7.133 min.; 100% |
| 16 | 3-(CF3)phenyl | O | CH2 | (M + Na) = 685.6 | 20-60%B; 10.177 min.; 100% |
| 17 | 4-(CF3)phenyl | O | CH2 | (M + Na) = 685.6 | 20-60%B; 10.265 min.; 100% |

TABLE 1-continued

Structures and analytical data - compounds 1-70.

| | Z | X | Y | MS Data | HPLC |
|---|---|---|---|---|---|
| 18 | 4-(trifluoromethoxy)phenyl | O | CH₂ | (M + Na) = 700.9 | 20-60%B; 10.696 min.; 100% |
| 19 | benzo[d][1,3]dioxine | O | CH₂ | (M + Na) = 709.4 | 30-70%B; 9.216 min.; 100% |
| 20 | naphthyl | O | CH₂ | (M + Na) = 667.3 | 20-60%B; 10.225 min; 100% |
| 21 | 3-cyanophenyl | O | CH₂ | (M + Na) = 641.8 | 20-60%B; 7.15 min.; 100% |
| 22 | 3,4-difluorophenyl | O | CH₂ | (M + Na) = 653.1 | 20-60%B; 8.822 min.; 100% |
| 23 | 5-chlorobenzo[b]thiophene | O | CH₂ | (M + Na) = 707.3 | 20-60%B; 11.362 min.; 100% |
| 24 | 2-(4-chlorophenyl)thiazole | O | CH₂ | (M + Na) = 733.9 | 20-60%B; 10.964 min.; 100% |
| 25 | 3,4-bis(benzyloxy)phenyl | O | CH₂ | (M + Na) = 828.2 | 40-80%B; 7.040 min.; 100% |

TABLE 1-continued

Structures and analytical data - compounds 1-70.

| | Z | X | Y | MS Data | HPLC |
|---|---|---|---|---|---|
| 26 | 1-naphthyl | O | CH₂ | (M + Na) = 667.5 | 30-70%B; 8.907 min.; 96% |
| 27 | 3,4-dichlorophenyl | O | C(O) | (M + H) = 677.3 | 10-60%B; 10.83 min; 80% |
| 28 | phenyl | O | C(O) | (M + H) = 609.3 | 10-60%B; 9.65 min; 98% |
| 29 | isobutyl | O | C(O) | (M + H) = 589.6 | 10-60%B; 9.52 min; 98% |
| 30 | HN-(2,4-dichlorophenyl) | O | C(O) | (M + H) = 692.3 | 10-60%B; 11.52 min; 98% (slow RT); 10-60%B; 10.73 min; 90% (fast RT) |
| 31 | HN-(2,3-dichlorophenyl) | O | C(O) | (M + H) = 692.3 | 10-60%B; 11.21 min; 98% (slow RT); 10-60%B; 10.23 min; 98% |
| 32 | HN-(3-chlorophenyl) | O | C(O) | (M + H) = 658.4 | 10-60%B; 10.72 min; 98% |

TABLE 1-continued

Structures and analytical data - compounds 1-70.

| | Z | X | Y | MS Data | HPLC |
|---|---|---|---|---|---|
| 33 | 4-amino-3,5-dichlorophenylamino | O | C(O) | (M + H) = 707.48 | 10-60%B; 9.9 min; 98% |
| 34 | 3-nitro-4-(piperidin-1-yl)phenylamino | O | C(O) | (M + H) = 752.6 | 10-60%B; 10.37 min; 98% |
| 35 | benzothiazol-6-ylamino | O | C(O) | (M + H) = 681.5 | 10-60%B; 8.40 min; 98% |
| 36 | 3-acetylphenylamino | O | C(O) | (M + H) = 666.6 | 10-60%B; 8.57 min; 86% |
| 37 | 4-acetylphenylamino | O | C(O) | (M + H) = 666.6 | 10-60%B; 8.70 min; 86% |

TABLE 1-continued
Structures and analytical data - compounds 1-70.
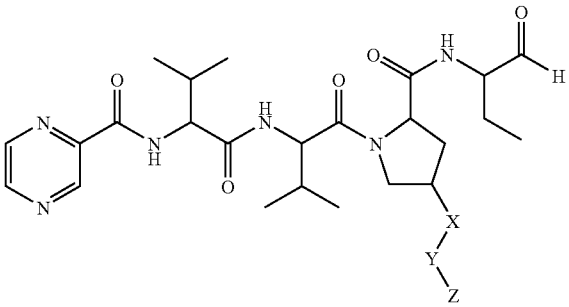
| | Z | X | Y | MS Data | HPLC |
|---|---|---|---|---|---|
| 38 | 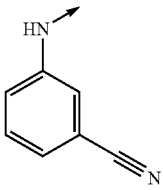 | O | C(O) | (M + H) = 649.6 | 10-60%; 9.44 min; 98% |
| 39 | 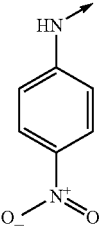 | O | C(O) | (M + H) = 669.6 | 10-60%B; 10.06 min; 94% |
| 40 | 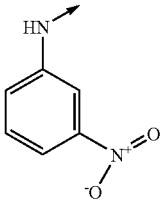 | O | C(O) | (M + H) = 669.6 | 10-60%B; 11.0 min; 96% (slow RT); 10-60%B; 10.12 min; 98% (fast RT) |
| 41 | 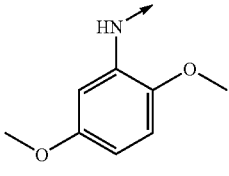 | O | C(O) | (M + H) = 684.6 | 10-60%B; 9.81 min; 95% |
| 42 | 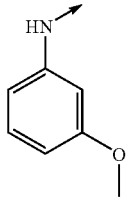 | O | C(O) | (M + H) = 654.6 | 10-60%B; 9.52 min; 98% |
| 43 | 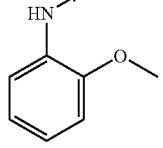 | O | C(O) | (M + H) = 654.6 | 10-60%B; 9.73 min; 93% |

TABLE 1-continued
Structures and analytical data - compounds 1-70.
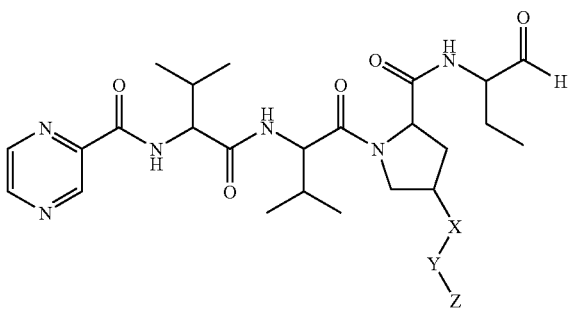
| | Z | X | Y | MS Data | HPLC |
|---|---|---|---|---|---|
| 44 | HN—benzo[d][1,3]dioxol-5-yl | O | C(O) | (M + H) = 668.56 | 10-60%B; 8.35 min; 92% |
| 45 | HN—2,6-dichlorophenyl | O | C(O) | (M + Na) = 716.5 | 10-60%B; 8.86 min; 80% |
| 46 | HN—3,4-dichlorophenyl | O | C(O) | (M + Na) = 716.1 | 10-60%B; 11.26/11.58 min (1:7); 98%; 10-60%B; 11.27/11.56 min (2:1); 98% |
| 47 | HN—4-methoxyphenyl | O | C(O) | (M + Na) = 678.1 | 10-60%B; 8.33 min; 96% |
| 48 | HN—naphthalen-1-yl | O | C(O) | (M + Na) = 697.8 | 10-60%B; 9.73 min; 90% |
| 49 | HN—phenyl | O | C(O) | (M + Na) = 647.2 | 10-60%B; 8.59 min; 90% |

TABLE 1-continued
Structures and analytical data - compounds 1-70.
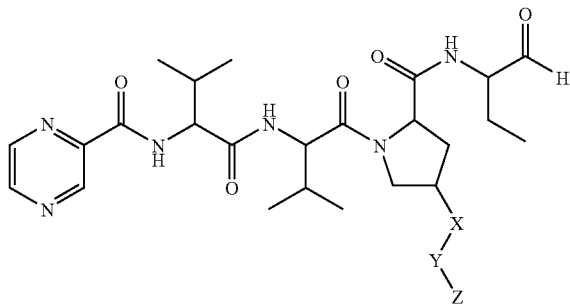
| | Z | X | Y | MS Data | HPLC |
|---|---|---|---|---|---|
| 50 | benzylamine | O | C(O) | (M + Na) = 660.6 | 10-60%B; 8.36 min; 94% |
| 51 | 2,6-dichloropyridin-4-ylamine | O | C(O) | (M + H) = 693.3 | 10-60%B; 9.42 min/10.37 min; 85% |
| 52 | 2-biphenylamine | O | C(O) | (M + H) = 700.4 | 10-60%B; 10.59 min; 98% |
| 53 | 3-phenoxyphenylamine | O | C(O) | (M + H) = 716.3 | 10-60%B; 11.24/12.18 min; 95% |
| 54 | 2-isopropylphenylamine | O | C(O) | (M + H) = 666.4 | 10-60%B; 9.97 min; 98% |
| 55 | methyl 2-aminobenzoate | O | C(O) | (M + H) = 682.3 | 10-60%B; 9.89 min; 98% |

TABLE 1-continued
Structures and analytical data - compounds 1-70.
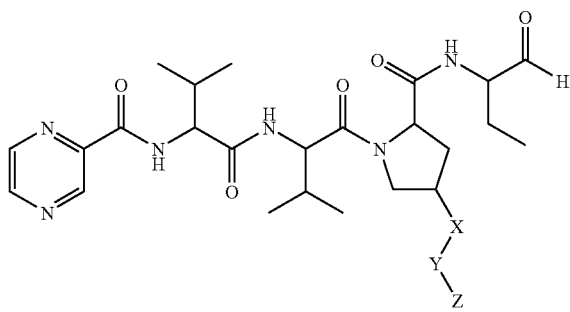
| | Z | X | Y | MS Data | HPLC |
|---|---|---|---|---|---|
| 56 | 3-(ethoxycarbonyl)phenylamino | O | C(O) | (M + H) = 696.3 | 10-60%B; 10.34 min; 98% |
| 57 | 3,4-dichlorophenyl | NH | C(O) | (M + H) = 676.31 | 20-60%B; 9.023 min.; 100% |
| 58 | benzylamino | NH | C(O) | (M + H) = 637.5 | 20-80%B; 5.152 min.; 100% |
| 59 | morpholino | NH | C(O) | (M + H) = 617.5 | 20-80%B; 3.216 min.; 100% |
| 60 | benzyloxy | NH | C(O) | (M + H) = 638.5 | 20-80%B; 6.221 min.; 100% |
| 61 | allyloxy | NH | C(O) | (M + H) = 588.4 | 20-80%B; 4.503 min.; 100% |
| 62 | phenyl | NH | C(O) | (M + H) = 608.5 | 20-80%B; 5.055 min.; 100% |
| 63 | phenethyl | NH | C(O) | (M + H) = 636.5 | 20-80%B; 5.697 min.; 100% |
| 64 | phenyl | NH | C(O)C(O) | (M + H) = 636.5 | 20-80%B; 5.548 min.; 100% |

TABLE 1-continued
Structures and analytical data - compounds 1-70.
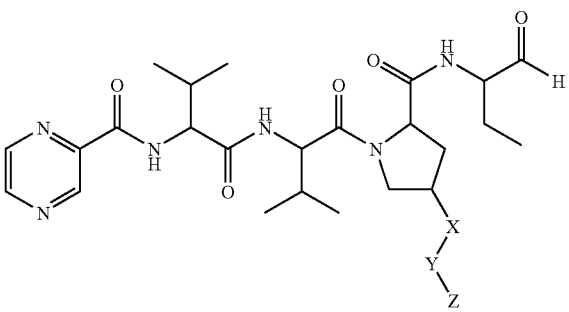
| | Z | X | Y | MS Data | HPLC |
|---|---|---|---|---|---|
| 65 | 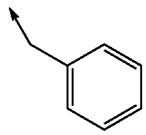 | NH | S(O)$_2$ | (M + H) = 658.4 | 20-80%B; 5.632 min.; 100% |
| 66 | 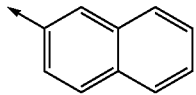 | NH | C(O) | (M + H) = 658.5 | 20-80%B; 6.690 min.; 100% |
| 67 | 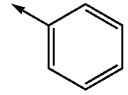 | NH | CH$_2$ | (M + H) = 594.5 | 20-80%B; 5.114 min.; 100% |
| 68 | 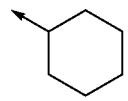 | NH | C(O) | (M + H) = 614.5 | 20-80%B; 5.559 min.; 100% |
| 69 | 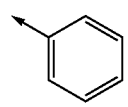 | O | CH$_2$ | (M + H) = 560.4 | 20-80%B; 8.062 min.; 100% |
| 70 | 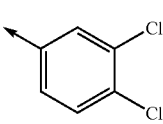 | O | CH$_2$ | (M + H) = 628.3 | 20-80%B; 9.990 min.; 100% |

TABLE 2
Structures and analytical data - compounds 71-79
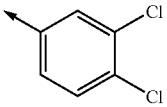
| | Z | W | MS Data | HPLC |
|---|---|---|---|---|
| 71 | 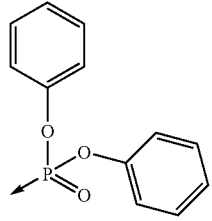 | 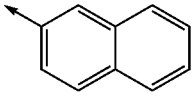 | (M + H) = 869.3 | 40-80%B; 8.812:8.920 min.; 2:1 mix at Abu; 100% |
| 72 | 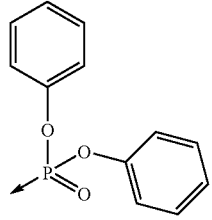 | 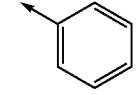 | (M + H) = 849.4 | 40-80%B; 8.380:8.539 min.; 2:1 mix at Abu; 100% |
| 73 | 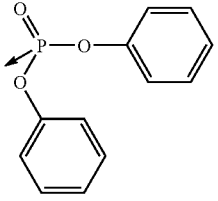 | 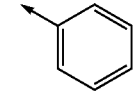 | (M + H) = 799.5 | 20-60%B; 12.519 min.; 95% |
| 74 | 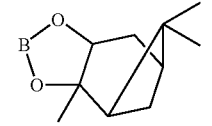 | 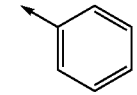 | (M + H) = 716 | 15.62 min.; >95% |
| 75 | 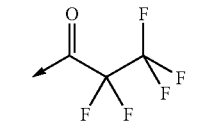 | 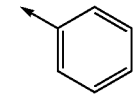 | (M + H) = 713 | 13.47 min. |
| 76 | 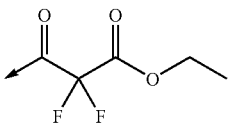 | 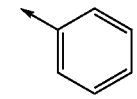 | (M + H) = 717 | 13.05 min.; >90% |
| 77 | 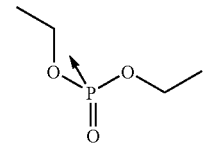 |  | (M + H) = 703 | 10-90%B; 8.5 min.; 8.6 min (2:1); >95% |

TABLE 2-continued
Structures and analytical data - compounds 71-79
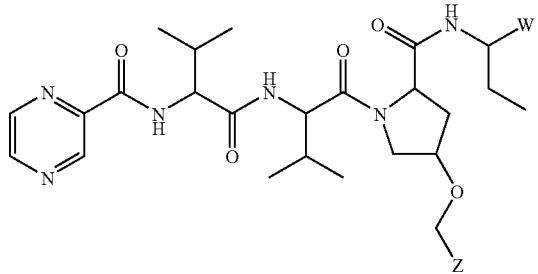
| | Z | W | MS Data | HPLC |
|---|---|---|---------|------|
| 78 | 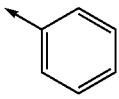 | 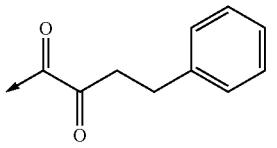 | (M + H) = 727 | 8.7 min.; 10 min. (2:1); 95% |
| 79 | 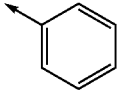 | 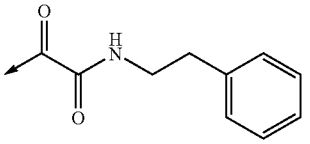 | (M + H) = 743 | 10-80%B; 5.4 min.; 95% |
TABLE 3
Structures and analytical data - compounds 80-88
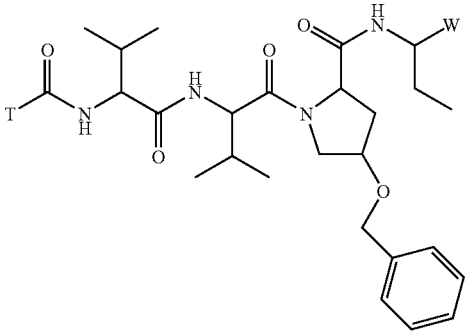
| | T | W | MS Data | HPLC |
|---|---|---|---------|------|
| 80 | 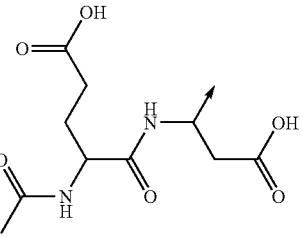 | 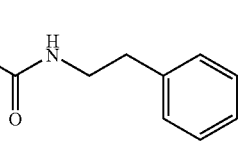 | (M + H) = 947 | 20-70%B; 6.15 min.; 95% |
| 81 | 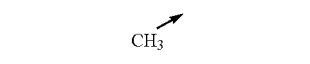 | C(O)H | (M + Na) = 553.60 | 5-45%B; 11.699 min.; 100% |
| 82 |  | C(O)H | (M + H) = 547.4 | 5-45%B; 11.083 min.; 100% |

TABLE 3-continued
Structures and analytical data - compounds 80-88
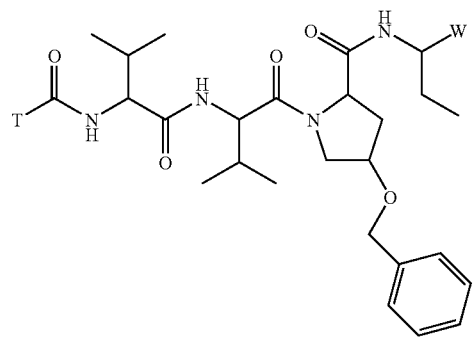
| | T | W | MS Data | HPLC |
|---|---|---|---|---|
| 83 | morpholine-N | C(O)H | (M + Na) = 625.3 | 5-45%B; 12.258 min.; 100% |
| 84 | HOOC-(CH2)3- | C(O)H | (M + Na) = 626.5 | 5-45%B; 11.083 min.; 100% |
| 85 | H3C-NH- | C(O)H | (M + Na) = 569.5 | 5-45%B; 11.606 min.; 100% |
| 86 | 3,5-dicarboxyphenyl-NH- | C(O)H | (M + Na) = 717.2 | 5-45%B; 7.942 min.; 100% |
| 87 | 2-carboxyphenyl-NH- | C(O)H | (M + H) = 655.3 | 15-55%B; 10.735 min.; 100% |
| 88 | PhCH2-O- | C(O)H | (M + Na) = 644.1 | 20-60%B; 11.360 min.; 98% |

TABLE 4
Structures and analytical data - compounds 89-126
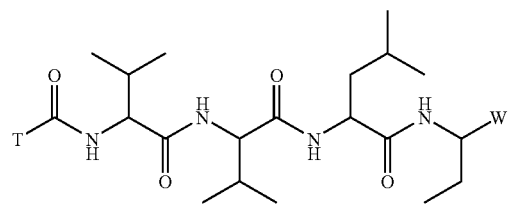
| | T | W | MS Data | HPLC |
|---|---|---|---|---|
| 89 |  | C(O)H | (M + H) = 555.9 | 5-45%B; 10.771 min.; 99% |
| 90 |  | C(O)H | (M + H) = 556.0 | 5-45%B; 13.055 min.; 95% |
| 91 |  | C(O)H | (M + H) = 522.4 | 5-45%B; 9.485 min.; 97% |
| 92 |  | C(O)H | (M + H) = 522.55 | 5-45%B; 9.072 min.; 100% |
| 93 |  | C(O)H | (M + H) = 506.33 | 5-45%B; 11.775 min.; 97% |
| 94 |  | C(O)H | (M + Na) = 526.6 | 5-45%B; 8.822 min.; 100% |
| 95 |  | C(O)H | (M + H) = 518. | 5-45%B; 8.484 min.; 100% |
| 96 |  | C(O)H | (M + H) = 619.6 | 5-45%B; 9.944 min.; 90% |
| 97 |  | C(O)H | (M + H) = 538.7 | 5-45%B; 9.099 min.; 100% |

TABLE 4-continued

Structures and analytical data - compounds 89-126

| | T | W | MS Data | HPLC |
|---|---|---|---|---|
| 98 | thiazole-pyridine | C(O)H | (M + H) = 588.6 | 5-45%B; 10.388 min.; 95% |
| 99 | morpholinopropyl | C(O)H | (M + H) = 541.1 | 5-45%B; 8.326 min.; 100% |
| 100 | 2,6-dimethoxypyridin-3-yl | C(O)H | (M + Na) = 587.3 | 35-75%B; 6.763 min.; 95% |
| 101 | Ac-Glu-Asp- | pyruvate | (M + H) = 729 | 10-80%B; 3.0 min; 95% |
| 102 | Ac-Glu-Asp- | benzyl-oxoacetamide | (M + H) = 819; (M + Na) = 840 | 20-70%B; 6.9 min; 95% |
| 103 | Ac-Glu-Asp- | 2-methoxybenzyl-oxoacetamide | (M + H) = 848; (M + Na) = 870 | 20-70%B; 6.3 min; 95% |

TABLE 4-continued

Structures and analytical data - compounds 89-126

| | T | W | MS Data | HPLC |
|---|---|---|---|---|
| 104 | Ac-Glu-Asp (T group) | phenethyl oxoacetamide | (M + H) = 833 | 20-70%B; 7.3 min; 95% |
| 105 | Ac-Glu-Asp | propyl oxoacetamide | (M + H) = 770; (M + Na) = 792 | 20-70%B; 6.0 min; 95% |
| 106 | Ac-Glu-Asp | 1-methoxypropan-2-yl oxoacetamide | (M + H) = 801; (M + Na) = 822 | 20-70%; 5.9 min; 95% |
| 107 | Ac-Glu-Asp | pyridin-4-ylmethyl oxoacetamide | (M + H) = 819; (M + Na) = 841 | 20-70%B; 3.24 min; 95% |
| 108 | Ac-Glu-Asp | tetrahydrofuran-2-ylmethyl oxoacetamide | (M + H) = 812; (M + Na) = 834 | 20-70%B; 4.9 min; 95% |

TABLE 4-continued

Structures and analytical data - compounds 89-126

| | T | W | MS Data | HPLC |
|---|---|---|---|---|
| 109 | (N-acetyl Glu-Asp fragment with OH groups) | morpholine amide of pyruvoyl | (M + H) = 798; (M + Na) = 820 | 20-70%B; 4.21 min; 95% |
| 110 | pyrazin-2-yl | pyruvic acid | (M + H) = 550 | 10-40%B; 7.0 min; 95% |
| 111 | pyrazin-2-yl | methyl pyruvate | (M + Na) = 886 | 10-50%B; 7.5 min; 95% |
| 112 | pyrazin-2-yl | N-benzyl pyruvamide | (M + H) = 638 | 10-80%B; 6.5 min; 95% |
| 113 | pyrazin-2-yl | N-[2-(3,4-dibenzyloxyphenyl)ethyl] oxoacetamide | (M + H) = 865 | 40-80%B; 5.7 min; 95% |
| 114 | pyrazin-2-yl | N-(2-methoxybenzyl) oxoacetamide | (M + H) = 669; (M + Na) = 693 | 25-40%B; 11.6 min; 95% |

TABLE 4-continued
Structures and analytical data - compounds 89-126
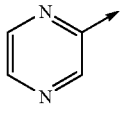
| | T | W | MS Data | HPLC |
|---|---|---|---|---|
| 115 | 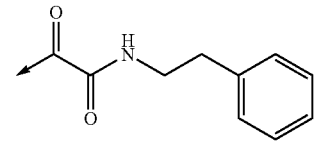 | 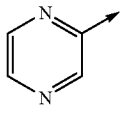 | (M + H) = 653 | 10-80%B; 6.80 min; 95% |
| 116 | 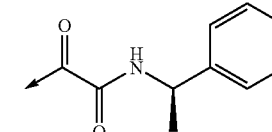 | 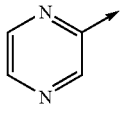 | (M + H) = 653 | 10-80%B; 6.7 min; 95% |
| 117 | 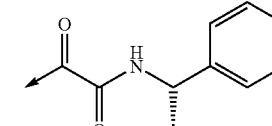 | 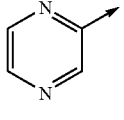 | (M + H) = 653 | 10-80%B; 6.7 min; 95% |
| 118 | 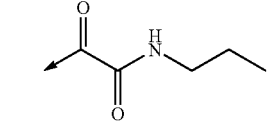 | 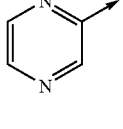 | (M + Na) = 611 | 10-80%B; 5.62 min; 95% |
| 119 | 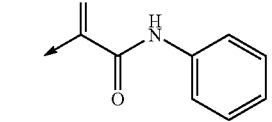 | 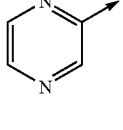 | (M + H) = 624 | 10-80%B; 12.1 min; 95% |
| 120 | 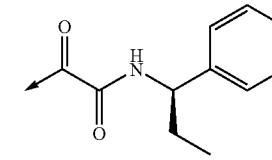 | 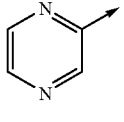 | (M + H) = 667 | 10-80%B; 13.4 min; 95% |
| 121 | 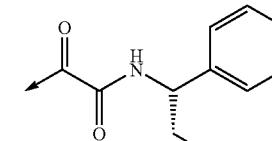 | 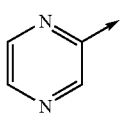 | (M + H) = 667 | 10-80%B; 13.3 min; 95% |
| 122 | 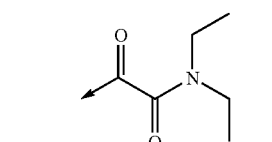 |  | (M + H) = 605 | 10-80%B; 11.0 min; 95% |

TABLE 4-continued
Structures and analytical data - compounds 89-126
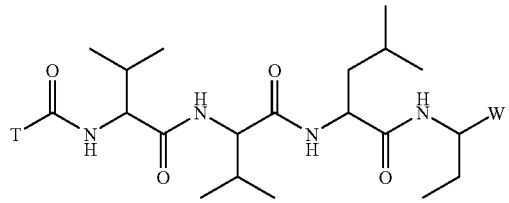
| | T | W | MS Data | HPLC |
|---|---|---|---|---|
| 123 | 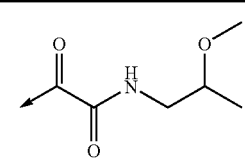 | 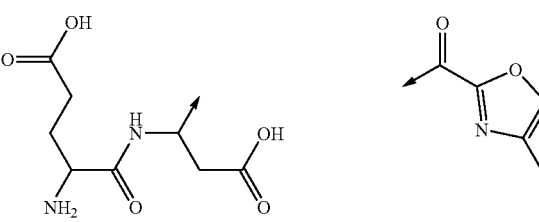 | (M + H) = 621 | 10-80%B; 9.7 min; 95% |
| 124 | 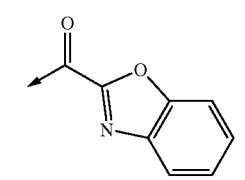 | 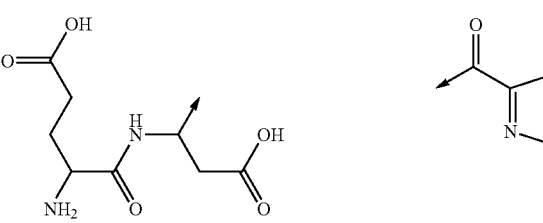 | (M + H) = 761 | 13.65 min.; 90% |
| 125 | 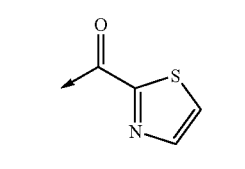 | 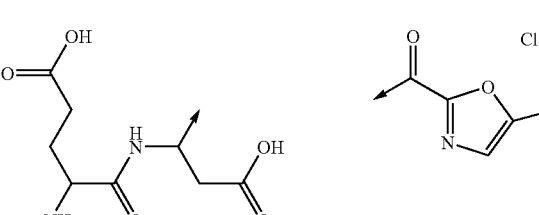 | (M + H) = 727 | ND |
| 126 | 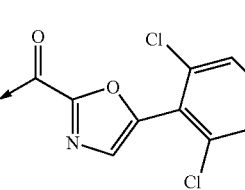 | | (M + H) = 856 | ND |

TABLE 5
Structures and analytical data - compounds 127-142
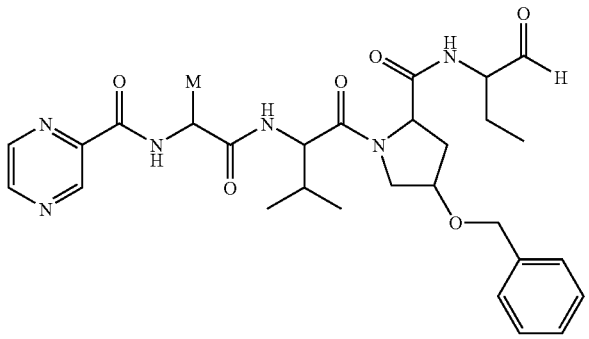
| | M | MS Data | HPLC |
|---|---|---|---|
| 127 | 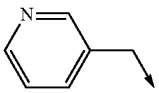 | (M + H) = 644.30 | 15-55%B; 6.08 min; 100% |
| 128 | 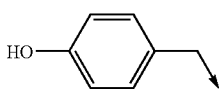 | (M + H) = 681.3 | 20-60%B; 8.11 min; 100% |
| 129 | 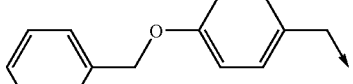 | (M + H) = 750.6 | 30-70%B; 6.99 min; 100% |
| 130 | 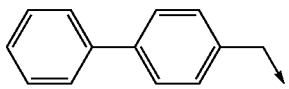 | (M + H) = 720.2 | 30-70%B; 6.71 min; 100% |
| 131 | 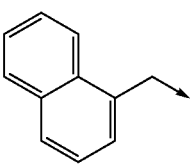 | (M + Na) = 715.4 | 30-70%B; 5.64 min; 100% |
| 132 | 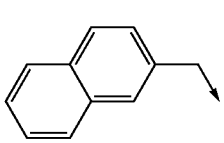 | (M + Na) = 715.2 | 30-70%B; 5.58 min; 100% |
| 133 | 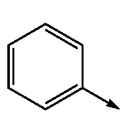 | (M + H) = 630.9 | 30-70%B; 3.78 min; 100% |
| 134 | 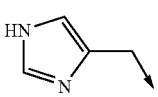 | (M + H) = 634.0 | 15-55%B; 5.90 min; 100% |
| 135 | 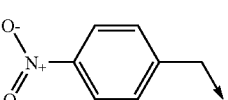 | (M + H) = 691.60 | 30-70%B; 4.22 min; 100% |
| 136 | 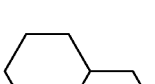 | (M + H) = 651.20 | 40-80%B; 5.59 min; 100% |

TABLE 5-continued
Structures and analytical data - compounds 127-142
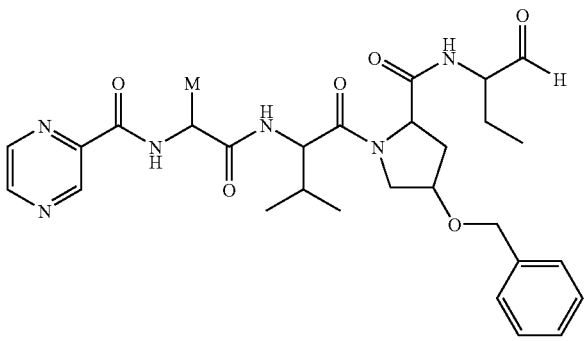
| | M | MS Data | HPLC |
|---|---|---|---|
| 137 | 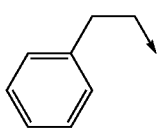 | (M + H) = 659.10 | 40-80%B; 4.65 min; 100% |
| 138 | 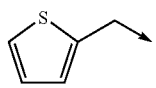 | (M + H) = 651.70 | 40-80%B; 3.83 min; 100% |
| 139 |  | (M + H) = 582.90 | 40-80%B; 2.34 min; 100% |
| 140 | 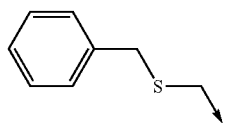 | (M + H) = 690.70 | 40-80%B; 5.15 min; 100% |
| 141 | 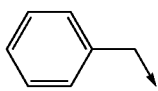 | (M + Na) = 664.80 | 40-80%B; 3.93 min; 100% |
| 142 | 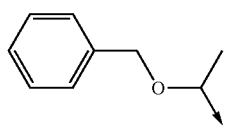 | (M + Na) = 708.80 | 40-80%B; 5.398 min; 100% |

TABLE 6

Structures and analytical data - compounds 143-197

| | T | U | MS Data | HPLC |
|---|---|---|---|---|
| 143 | benzyl | S(O₂) | (M + Na) = 566.71 | 20-80%B; 10.186 min.; >95% |
| 144 | phenyl | S(O₂) | (M + Na) = 552.26 | 20-80%B; 9.985 min.; 90% |
| 145 | anilino | C(O) | (M + Na) = 531.60 | 20-80%B; 9.978 min; 95% |
| 146 | styryl (cis) | C(O) | (M + Na) = 542.37 | 20-80%B; 10.404 min; 95% |
| 147 | phenethyl | C(O) | (M + Na) = 544.42 | 20-80%B; 10.246 min; 95% |
| 148 | H₃C— | C(O) | (M + Na) = 454.26 | 20-80%B; 7.109 min; 95% |
| 149 | phenyl | C(O) | (M + Na) = 516.05 | 20-80%B; 9.668 min; 95% |
| 150 | PhCH₂C(O)NH-C₆H₄-CH₂— | C(O) | (M + Na) = 649.17 | 20-80%B; 9.880 min; 95% |
| 151 | PhC(O)NH-C₆H₄-CH₂— | C(O) | (M + Na) = 648.45 | 20-80%B; 10.030 min; 95% |
| 152 | CH₃C(O)NH-C₆H₄-CH₂— | C(O) | (M + Na) = 587.08 | 20-80%B; 7.892 min; 95% |

TABLE 6-continued

Structures and analytical data - compounds 143-197

| | T | U | MS Data | HPLC |
|---|---|---|---|---|
| 153 | 2-pyrrolyl | C(O) | (M + Na) = 505.47 | 20-80%B; 8.583 min; 95% |
| 154 | 2-indolyl | C(O) | (M + Na) = 554.96 | 20-80%B; 10.411 min; 95% |
| 155 | 2-amino-4-thiazolylmethyl | C(O) | (M + Na) = 551.90 | 20-80%B; 6.737 min; 95% |
| 156 | 3-chloro-4-hydroxyphenyl | C(O) | (M + Na) = 566.11 | 20-80%B; 9.227 min; 95% |
| 157 | 2-amino-thiazol-4-yl (methoxyimino) | C(O) | (M + Na) = 594.59 | 20-80% B; 7.567 min; 95% |
| 158 | 1-isoquinolyl | C(O) | (M + Na) = 567.00 | 20-80%B; 10.409 min; 95% |
| 159 | 1-naphthyl | C(O) | (M + Na) = 566.10 | 20-80%B; 10.716 min; 95% |
| 160 | cyclohexylidene-cyanomethyl | C(O) | (M + Na) = 559.27 | 20-80%B; 10.597 min; 95% |

TABLE 6-continued

Structures and analytical data - compounds 143-197

| | T | U | MS Data | HPLC |
|---|---|---|---|---|
| 161 | 2-nitrobenzyl | C(O) | (M + Na) = 574.66 | 20-80%B; 9.723 min; 95% |
| 162 | 3-phenoxybenzyl | C(O) | (M + Na) = 607.43 | 20-80%B; 12.019 min; 95% |
| 163 | thiophen-3-ylmethyl | C(O) | (M + H) = 514.83 | 20-80%B; 6.170 min; 95% |
| 164 | α-methoxybenzyl | C(O) | (M + H) = 538.87 | 20-80%B; 7.094 min; 99%; 20-80%B; 6.712 min; 99% |
| 165 | diphenyl(hydroxy)methyl | C(O) | (M + Na) = 620.77 | 20-80%B; 8.390 min; 99% |
| 166 | 3-phenylpropyl | C(O) | (M + H) = 536.44 | 20-80%B; 7.787 min; 99% |
| 167 | α-fluorobenzyl | C(O) | (M + H) = 525.58 | 20-80%B; 7.023 min; 99% |
| 168 | 2-hydroxynaphth-1-ylmethyl | C(O) | (M + Na) = 582.25 | 20-80%B; 7.220 min; 98% |

TABLE 6-continued

Structures and analytical data - compounds 143-197

| | T | U | MS Data | HPLC |
|---|---|---|---|---|
| 169 | 2-(ethoxy)benzaldehyde group | C(O) | (M + H) = 552.32 | 20-80%B; 6.410 min; 99% |
| 170 | 1-phenyl-propan-1-one group | C(O) | (M + H) = 550.77 | 20-80%B; 6.663 min; 99% |
| 171 | 2-phenoxyethyl group | C(O) | (M + H) = 538.87 | 20-80%B; 7.101 min; 99% |
| 172 | 2-carboxyhexyl group | C(O) | (M + Na) = 554.79 | 20-80%B; 7.011 min; 99% |
| 173 | 1-phenoxypropyl group | C(O) | (M + H) = 551.59 | 20-80%B; 8.029 min; 96% |
| 174 | 1-phenylbutyl group | C(O) | (M + H) = 549.86 | 20-80%B; 7.320 min; 99% |
| 175 | indol-3-ylmethyl group | C(O) | (M + Na) = 554.79 | 20-80%B; 6.413 min; 99% |
| 176 | 2,3-dimethoxybenzyl group | C(O) | (M + H) = 555.05 | 20-80%B; 7.065 min; 99% |

TABLE 6-continued

Structures and analytical data - compounds 143-197

| | T | U | MS Data | HPLC |
|---|---|---|---|---|
| 177 | 2-phenylcyclopentyl | C(O) | (M + Na) = 584.55 | 20-80%B; 9.099 min; 99% |
| 178 | 1-phenylcyclopropyl | C(O) | (M + H) = 535.23 | 20-80%B; 8.038 min; 99% |
| 179 | 1,2,3,4-tetrahydroisoquinolin-3-yl | C(O) | (M + Na) = 569.07 | 10-80%B; 5.885; 98% |
| 180 | 1,2,3,4-tetrahydroisoquinolin-1-yl | C(O) | (M + H) = 548.03 | 10-80% B; 5.991; 99% |
| 181 | 3,5-dimethylisoxazol-4-yl | C(O) | (M + Na) = 533.91 | 10-80%B; 7.237; 99% |
| 182 | 3-(2-chlorophenyl)-5-methylisoxazol-4-yl | C(O) | (M + Na) = 630.91 | 10-80%B; 9.382; 95% |
| 183 | 1,2,3,4-tetrahydroacridin-9-yl | C(O) | (M + H) = 599.4 | 10-80% B; 7.0 min; 99% |

TABLE 6-continued

Structures and analytical data - compounds 143-197

| | T | U | MS Data | HPLC |
|---|---|---|---|---|
| 184 | (2-methyl-6-substituted phenol with HO) | C(O) | (M + Na) = 545.27 | 10-80%B; 6.89 min; 99% |
| 185 | 1-benzyl-indol-3-yl | C(O) | (M + Na) = 643.91 | 10-80%B; 10.43 min; 99% |
| 186 | 3-(2,6-dichlorophenyl)-5-methylisoxazol-4-yl | C(O) | (M + Na) = 664.69 | 10-80%B; 9.95 min; 99% |
| 187 | 1-phenyl-5-methylpyrazol-4-yl | C(O) | (M + Na) = 595.53 | 10-80%B; 8.61 min; 99% |
| 188 | 3-phenyl-5-methylisoxazol-4-yl | C(O) | (M + Na) = 596.45 | 10-80%B; 9.0 min; 92% |
| 189 | 2,5-dimethylfuran-3-yl | C(O) | (M + Na) = 533.73 | 10-80%B; 8.438; 99% |
| 190 | 1H-indol-3-yl | C(O) | (M + Na) = 554.20 | 10-80%B; 7.990; 99% |
| 191 | 2,4,6-trimethylphenyl | C(O) | (M + Na) = 557.74 | 10-80%B; 9.06 min; 99% |

TABLE 6-continued
Structures and analytical data - compounds 143-197
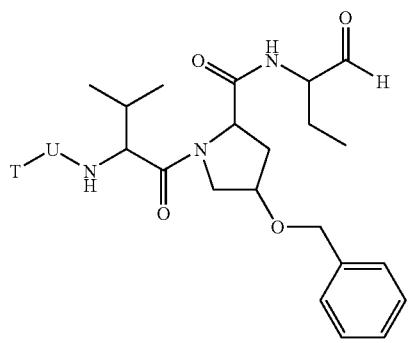
| | T | U | MS Data | HPLC |
|---|---|---|---|---|
| 192 | (2-methyl-6-methylphenol) | C(O) | (M + Na) = 545.70 | 10-80%B; 10.11 min; 99% |
| 193 | (2,3-dimethylphenyl) | C(O) | (M + Na) = 544.06 | 10-80%B; 8.41 min; 99% |
| 194 | (2-methoxyphenyl) | C(O) | (M + Na) = 545.49 | 10-80%B; 8.41 min; 96% |
| 195 | (2-bromophenyl) | C(O) | (M + Na) = 594.05 | 10-80%B; 8.3 min; 99% |
| 196 | (1-ethoxynaphthalenyl) | C(O) | (M + H) = 574.3 | 10-80%B; 8.84 min; 98% |
| 197 | (2-ethoxynaphthalenyl) | C(O) | (M + H) = 588.4 | 10-80%B; 9.37 min; 99% |

TABLE 7

Structure and analytical data - compound 198.

[Chemical structure of compound 198]

| | MS Data | HPLC |
|---|---|---|
| 198 | (M + Na) = 702.4 | 10-60% B; 4.2 min.; >95% |

Example 11

Insofar as compounds of formula (I) or (II) are able to inhibit NS3 serine protease, they are of evident clinical utility for the treatment of viral diseases, including HCV. These tests are predictive of the compound's ability to inhibit HCV in vivo.

Peptides and Assays.

Peptides EDVV abuCSMSY (Abu designates—aminobutyric acid), DEMEECSQHLPYI, ECTTPCSGSWLRD and EDVV AbuC-p-nitroanilide was purchased from AnaSpec Inc. (San Jose, Calif.).

Peptide content of purified, lyophilized peptides and in-house peptides was determined by quantitative nitrogen analysis and the appropriate values were used in preparing stock peptide solutions (Galbreath). pKa determinations were determined by Robertson Microlit Laboratories, Inc. (Madison, N.J.).

HPLC cleavage assays were performed using 25 nM to 3.0 µM enzyme in 100 µL volumes at 30 C. containing 50 mM HEPES-KOH (pH 7.8), 100 mM NaCl, 20% glycerol, 5 mM DTT and the appropriate amount of substrate (in DMSO), with or without NS4A peptide, such that the final concentration of DMSO did not exceed 4%. Separate control experiments verified that this percentage of DMSO did not effect enzymatic activity. Cleavage reactions were quenched by the addition of an equal volume of a mixture of 10% TFA:acetonitrile(1:1) and activity was assessed on a reversed phase HPLC column (Rainin C18 Microsorb-MV, 5 mm, 4.6×250 mm; 0-50% acetonitrile, 0.1% TFA @ 3.33% min) using a Hewlett Packard 1050 instrument with auto-injection and diode array detection at 210 nm and 280 nm (where appropriate). Peptide elution fragments were collected and identified by mass spectrometry and N-terminal sequence analysis. Fragment identity and concentration was further verified by authentic, synthesized products. Initial rates of cleavage were determined at <20% substrate conversion and catalytic parameters were determined assuming Michaelis-Menten kinetics using the MultiFit program (Day Computing, Cambridge, Mass.).

Spectrophotometric assays were run in a 96-well microtiter plate at 30 C., using a SpectraMax 250 reader (Molecular Devices, Sunnyvale, Calif.) with kinetic capability. Cleavage of EDVV AbuC-p-nitroanilide (5A-pNA) substrate was performed with or without NS44 in the same buffer used for HPLC assays at 30 C., and pNA release was monitored at 405 nm. The extinction coefficient of p-nitroaniline is independent of pH at values of 5.5. and above [Tuppy, H., et al., *Hoppe-Seyler's Z. Physiol. Chem.*, 329, pp. 278-288 (1962)]; Raybuck and Luong, unpublished observations). The percentage of DMSO did not exceed 4% in these assays.

Determination of the pH dependence of Vmax, $K_m$ and $V_{max}/K_m$ was performed using a series of constant ionic strength buffers containing 50 mM MES, 25 Nm Tris, 25 mM ethanolamine and 0.1 M NaCl [Morrison, J. F. and Stone, R. F., *Biochemistry*, 27, pp. 5499-5506 (1988)]. The inflection point for log V data was calculated by nonlinear least squares fit of the data to the equation:

$$\log v = \log [V\max/(1+H/K_a)]$$

[Dixon, M. and Webb, E. C. *Enzymes*; Academic Press: New York; Vol., pp. 138-164 (1979)]. The inflection points for log(V/K) data were calculated by nonlinear least squares fit of the data to the equation $\log v = \log [V\max/(1+H/K_a+K_b/H)]$ [Dixon, M. and Webb, E. C. *Enzymes*; Academic Press: New York; Vol., pp. 138-164 (1979)]. The program KineTic (BioKin Ltd) was used in both cases.

Kinetic constants for the rapid equilibrium ordered bisubstrate reaction were determined from rate vs [4A], [EDVV AbuC-pNA] data by non-linear least squares fitting to equation 1 [Morrison, J. F. *Biochim. Biophys. Acta*, 185, pp. 269-286 (1969)] as described in the text. $K_{ii}$ and $K_{is}$ values for peptidyl inhibitors were determined from rate vs [inhibitor], [substrate] data and fitting to the equation for mixed inhibition:

$$\text{rate} = V\max[S]/\{Km(1+[I]/Kis)+[S](1+[I]/Kii)\}$$

The commercial program KinetAsyst (State College, Pa.) was used for both procedures. Ki values were calculated from rate vs [inhibitor] plots by a nonlinear least squares fit of the data to the equation of Morrison for tight binding competitive inhibition [Morrison, J. F. *Biochim. Biophys. Acta*, 185, pp. 269-286 (1969)]. The KineTic program (BioKin Ltd) was used for this procedure.

The results are shown in Table 8. $K_i$ values are expressed in µM. Category "A" indicates <1 µM inhibition; category "B" indicates 1-100 µM inhibition; category "C" indicates >100 µM. The designation "ND" indicates that the compound was not tested.

TABLE 8

Enzyme inhibition data for compounds 1-198.

| Cmpd. No. | Ki (µM) |
|---|---|
| 1 | B |
| 2 | B |
| 3 | B |
| 4 | B |
| 5 | B |
| 6 | B |
| 7 | B |
| 8 | B |
| 9 | B |
| 10 | B |
| 11 | B |
| 12 | B |
| 13 | B |
| 14 | B |
| 15 | B |
| 16 | B |
| 17 | B |
| 18 | B |
| 19 | B |
| 20 | B |
| 21 | B |
| 22 | B |
| 23 | B |
| 24 | B |

TABLE 8-continued

Enzyme inhibition data for compounds 1-198.

| Cmpd. No. | Ki (μM) |
|---|---|
| 25 | B |
| 26 | B |
| 27 | B |
| 28 | B |
| 29 | B |
| 30 | B |
| 31 | B |
| 32 | B |
| 33 | C |
| 34 | B |
| 35 | B |
| 36 | C |
| 37 | B |
| 38 | B |
| 39 | B |
| 40 | B |
| 41 | B |
| 42 | B |
| 43 | B |
| 44 | B |
| 45 | B |
| 46 | B |
| 47 | B |
| 48 | B |
| 49 | B |
| 50 | B |
| 51 | B |
| 52 | B |
| 53 | B |
| 54 | B |
| 55 | B |
| 56 | C |
| 57 | B |
| 58 | B |
| 59 | B |
| 60 | C |
| 61 | C |
| 62 | B |
| 63 | B |
| 64 | B |
| 65 | B |
| 66 | B |
| 67 | C |
| 68 | C |
| 69 | B |
| 70 | B |
| 71 | A |
| 72 | B |
| 73 | B |
| 74 | B |
| 75 | B |
| 76 | C |
| 77 | C |
| 78 | B |
| 79 | B |
| 80 | A |
| 81 | B |
| 82 | B |
| 83 | B |
| 84 | B |
| 85 | B |
| 86 | B |
| 87 | B |
| 88 | B |
| 89 | B |
| 90 | B |
| 91 | B |
| 92 | B |
| 93 | B |
| 94 | B |
| 95 | B |
| 96 | B |
| 97 | B |
| 98 | B |
| 99 | B |
| 100 | B |
| 101 | A |
| 102 | A |
| 103 | A |
| 104 | A |
| 105 | A |
| 106 | A |
| 107 | A |
| 108 | A |
| 109 | B |
| 110 | B |
| 111 | C |
| 112 | B |
| 113 | B |
| 114 | C |
| 115 | B |
| 116 | B |
| 117 | B |
| 118 | B |
| 119 | C |
| 120 | B |
| 121 | C |
| 122 | C |
| 123 | B |
| 124 | B |
| 125 | B |
| 126 | C |
| 127 | C |
| 128 | B |
| 129 | B |
| 130 | C |
| 131 | B |
| 132 | B |
| 133 | B |
| 134 | C |
| 135 | B |
| 136 | B |
| 137 | B |
| 138 | B |
| 139 | C |
| 140 | B |
| 141 | B |
| 142 | B |
| 143 | C |
| 144 | C |
| 145 | B |
| 146 | B |
| 147 | C |
| 148 | C |
| 149 | B |
| 150 | B |
| 151 | C |
| 152 | C |
| 153 | B |
| 154 | B |
| 155 | B |
| 156 | B |
| 157 | B |
| 158 | B |
| 159 | B |
| 160 | B |
| 161 | C |
| 162 | B |
| 163 | C |
| 164 | C |
| 165 | C |
| 166 | C |
| 167 | C |
| 168 | B |
| 169 | C |
| 170 | C |
| 171 | C |
| 172 | C |
| 173 | C |
| 174 | B |

TABLE 8-continued

Enzyme inhibition data for compounds 1-198.

| Cmpd. No. | Ki (µM) |
|---|---|
| 175 | B |
| 176 | C |
| 177 | C |
| 178 | C |
| 179 | B |
| 180 | C |
| 181 | C |
| 182 | C |
| 183 | B |
| 184 | B |
| 185 | B |
| 186 | C |
| 187 | C |
| 188 | C |
| 189 | C |
| 190 | C |
| 191 | C |
| 192 | C |
| 193 | C |
| 194 | C |
| 195 | B |
| 196 | B |
| 197 | B |
| 198 | A |

While we have hereinbefore presented a number of embodiments of this invention, it is apparent that the basic construction can be altered to provide other embodiments which utilize the methods of this invention. Therefore, it will be appreciated that the scope of this invention is to be defined by the claims appended hereto rather than the specific embodiments which have been presented hereinbefore by way of example.

What is claimed is:

1. A compound of the formula (II):

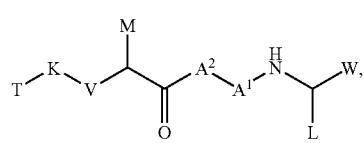

(II)

wherein

W is:

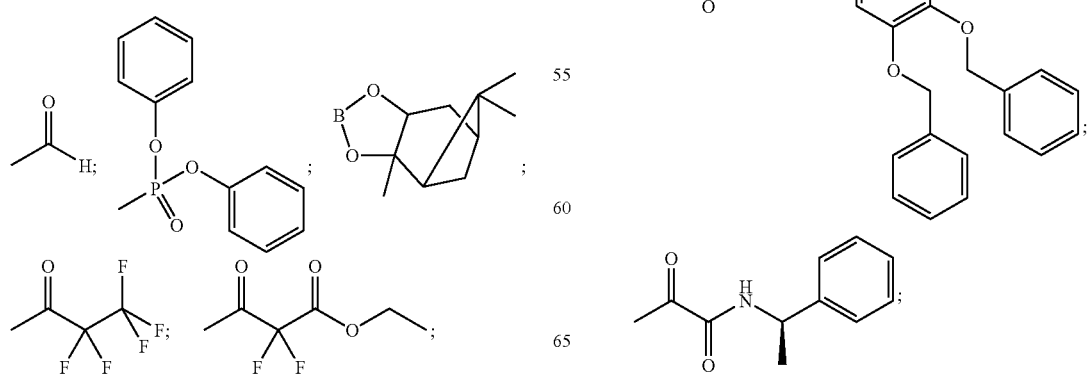

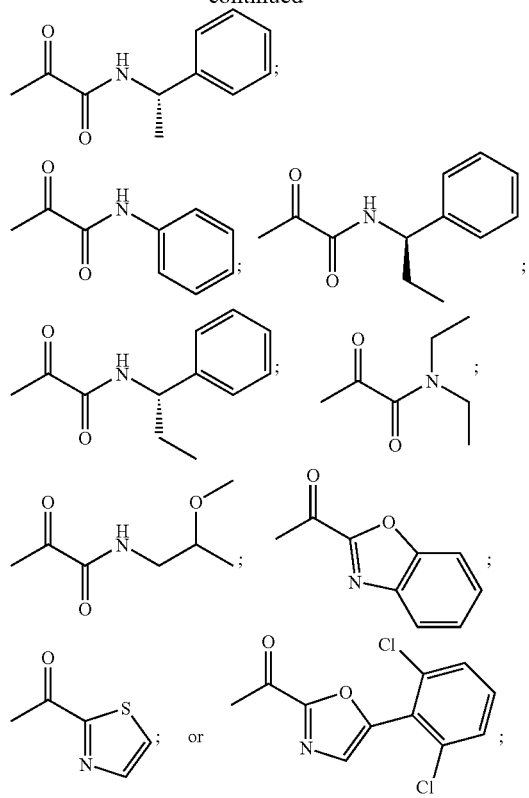
L is ethyl;
A¹ is
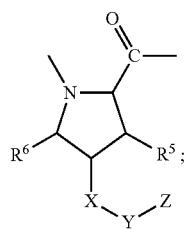
R⁴ is —CH₂—CH(CH₃)₂;
R⁵ and R⁶ are H;
X is O or NH;
Y is CH₂; C(O); C(O)(O); or S(O)₂;
Z is
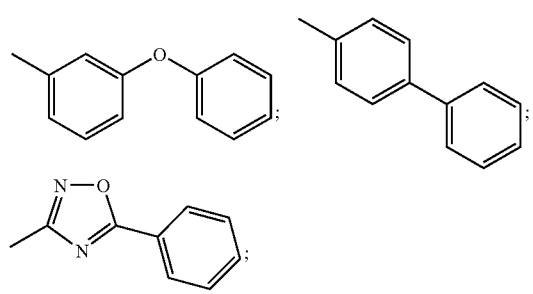
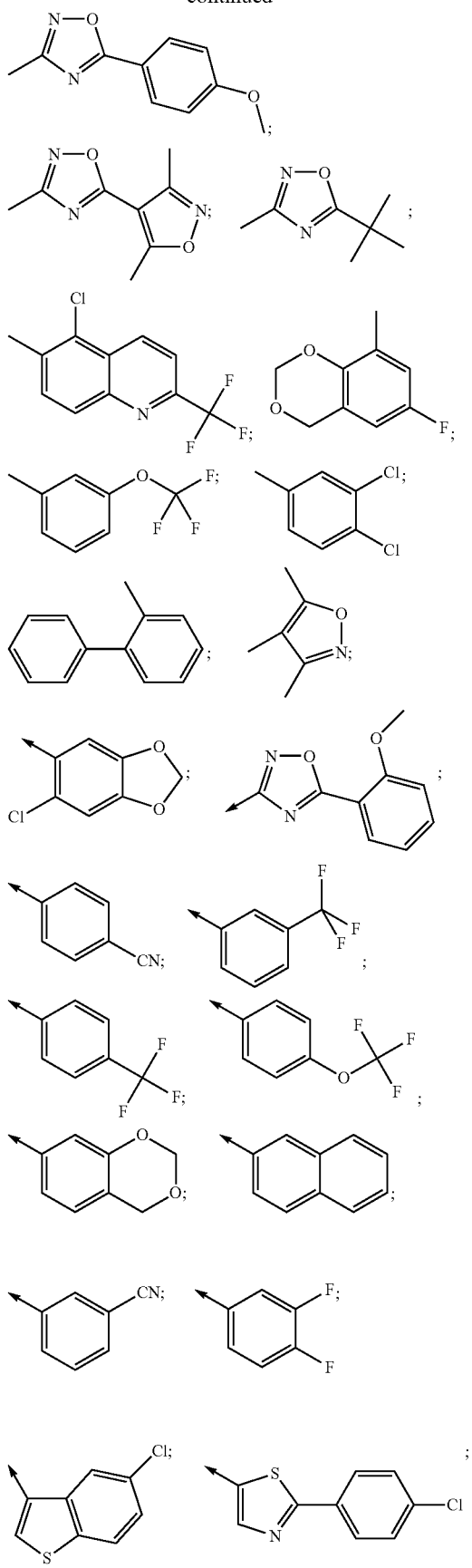

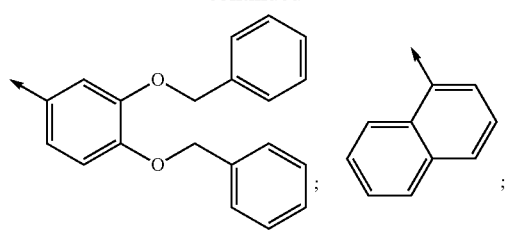
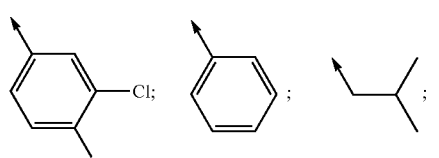
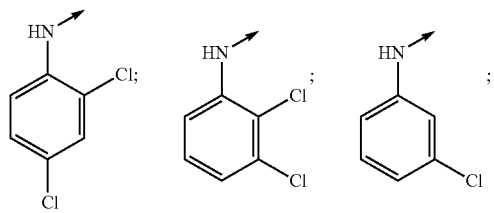
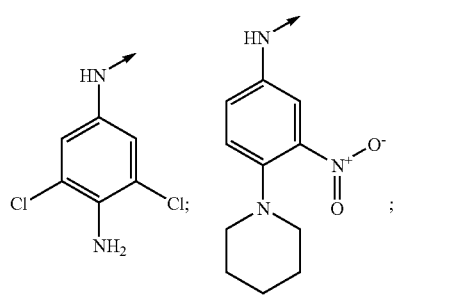
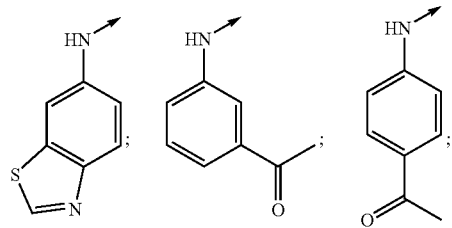
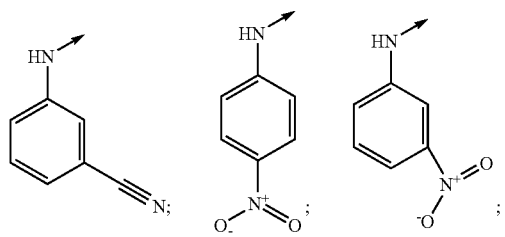
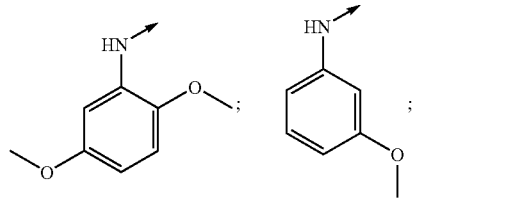
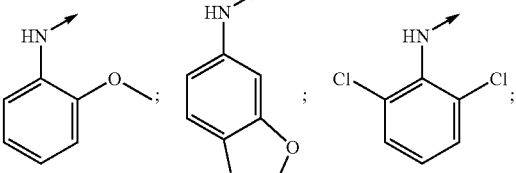
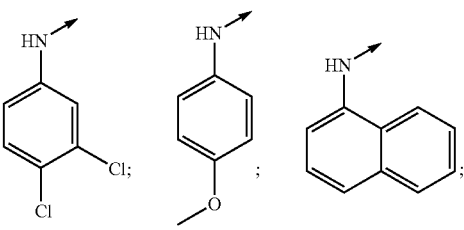
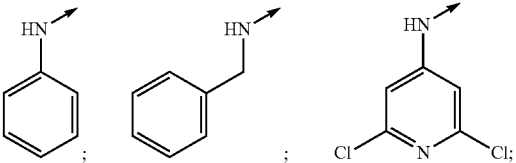
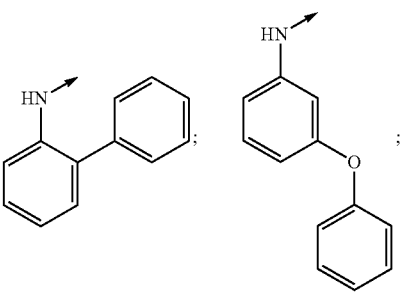
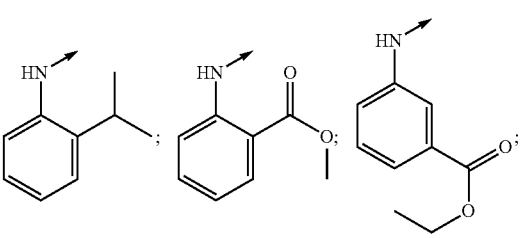
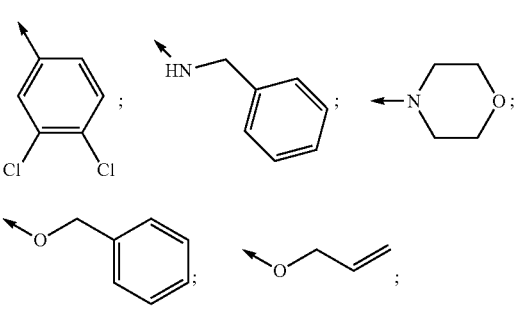
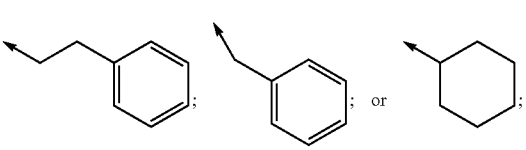

$A^2$ is
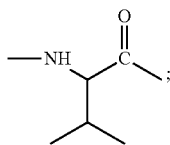
M is —CH(CH$_3$)$_2$;
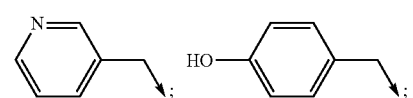
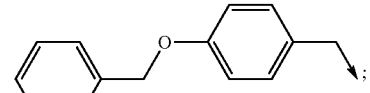
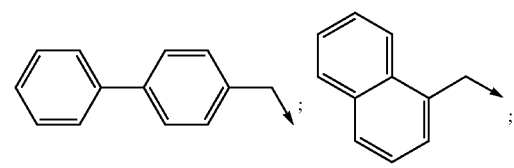
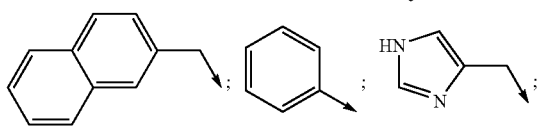
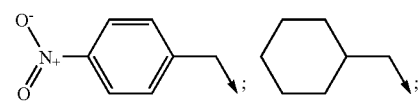
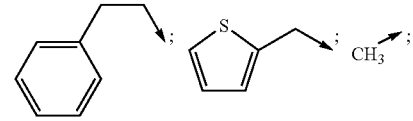
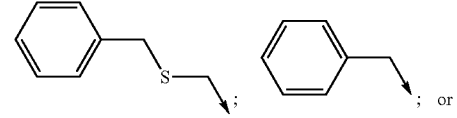
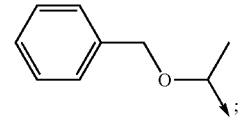
V is NH;
K is C(O) or S(O)$_2$; and
T is
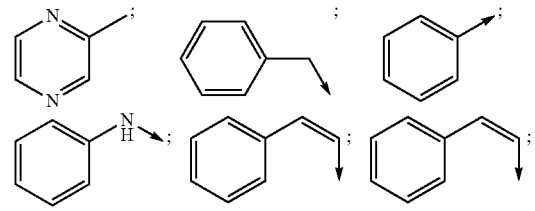
-continued
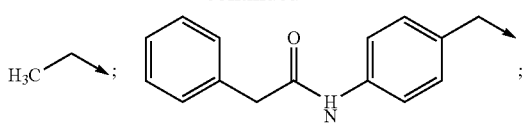
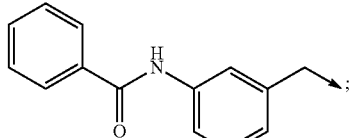
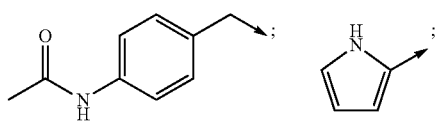
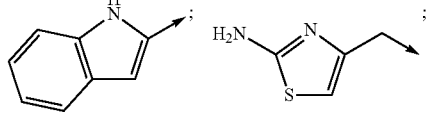
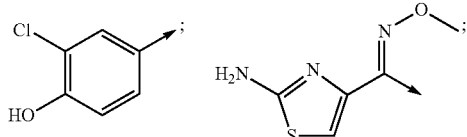
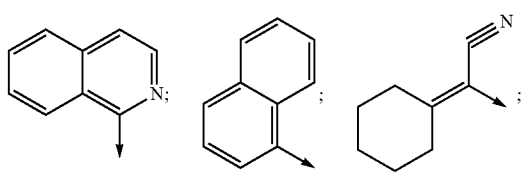
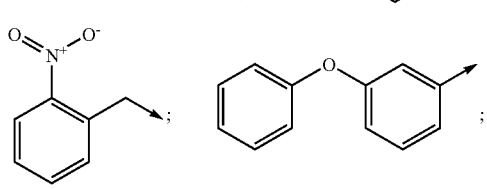
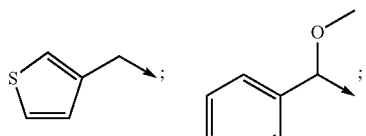
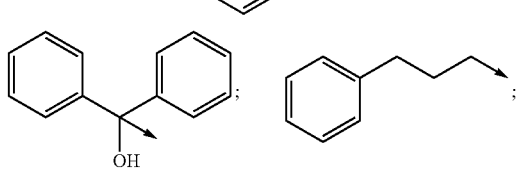
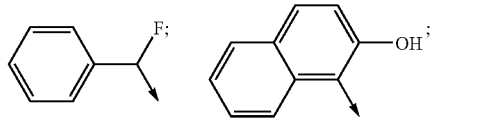
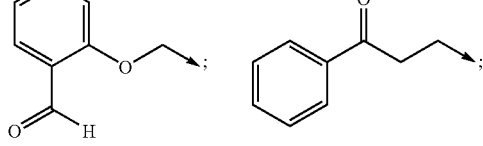

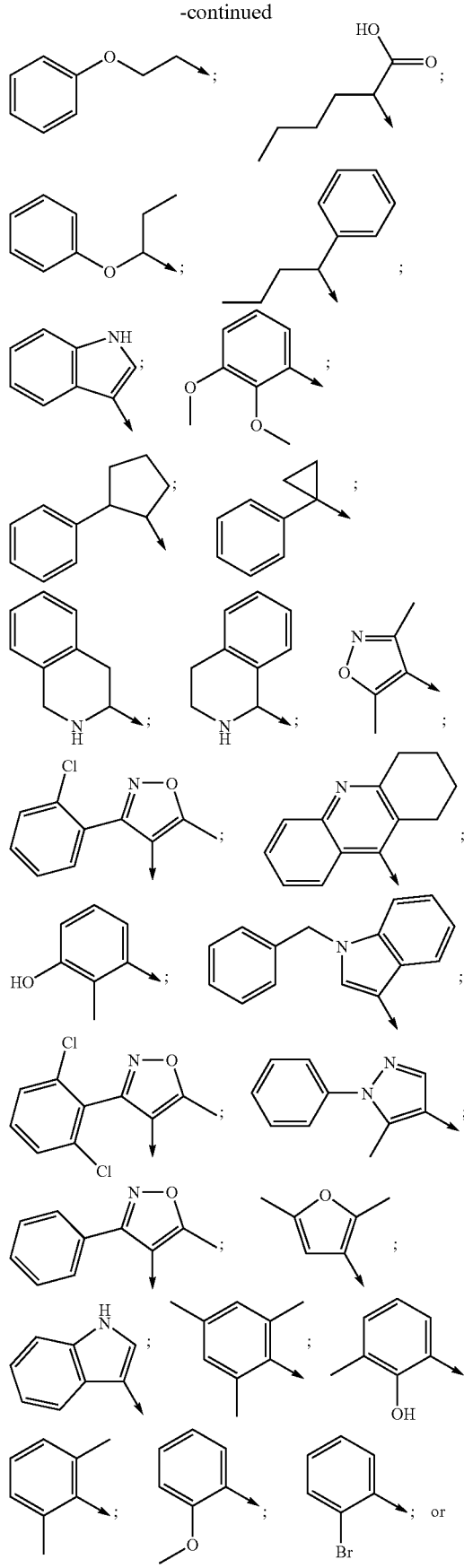
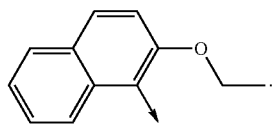
2. The compound according to claim 1, wherein the compound has the following formula:
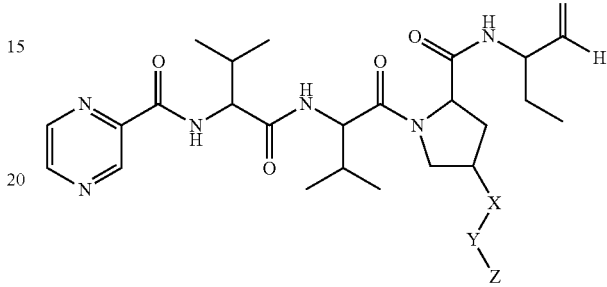
and wherein if X is O and Y is CH$_2$; then Z is
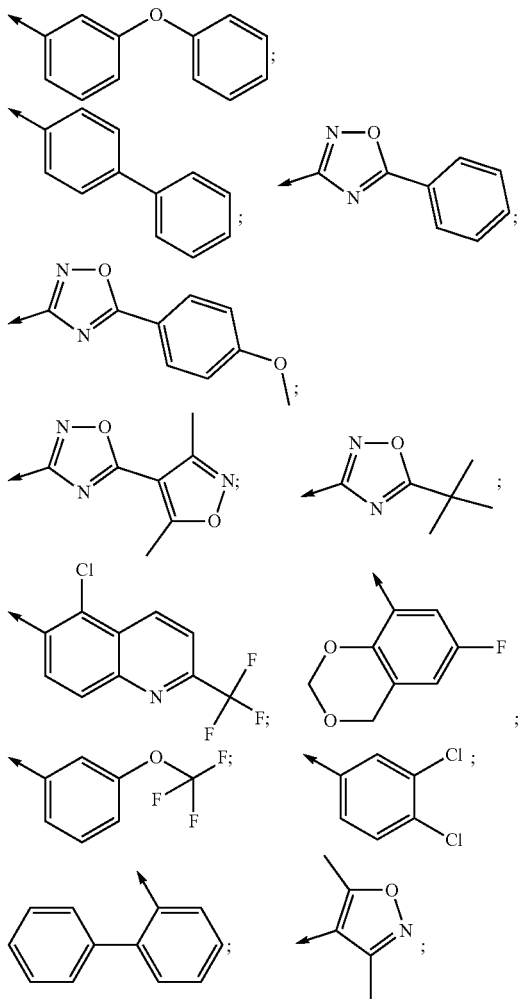

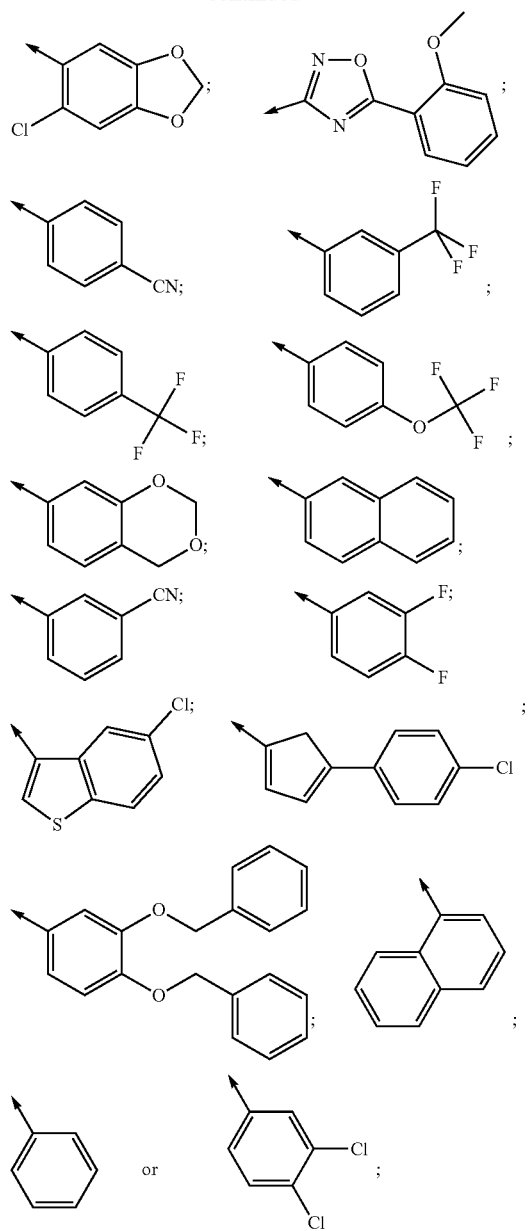
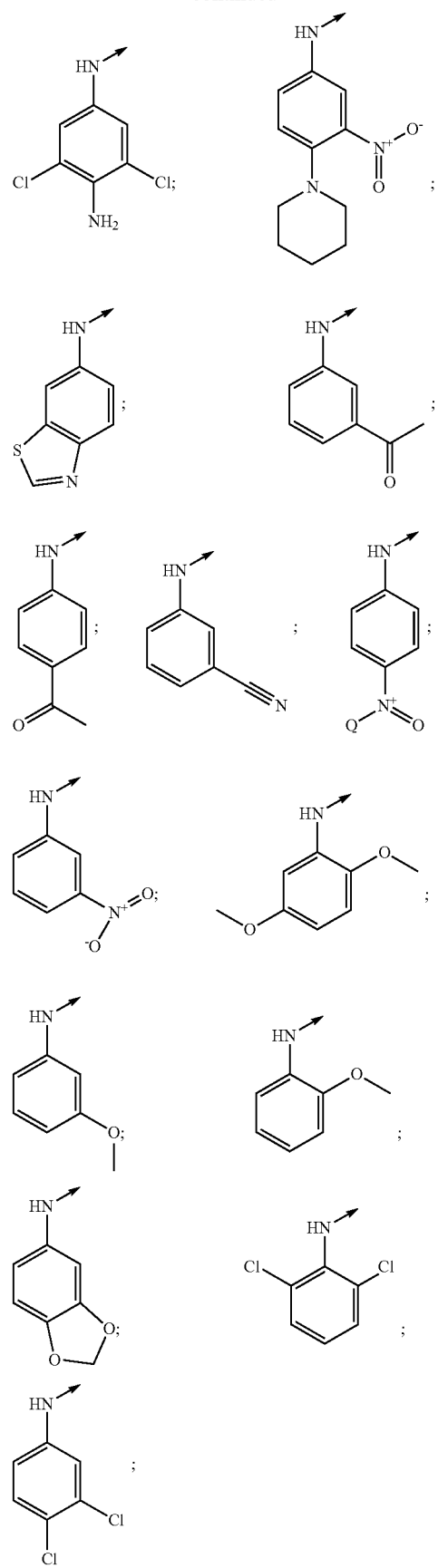
and wherein if X is O and Y is C(O); then Z is
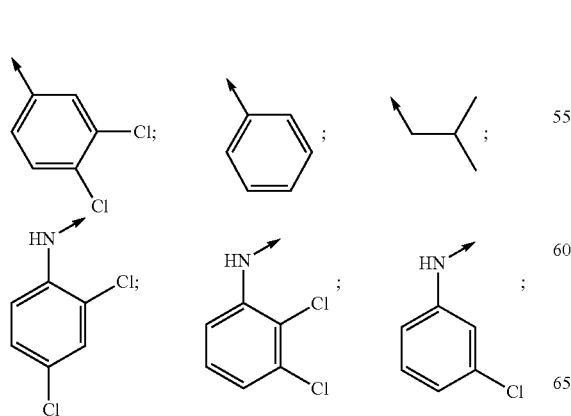

-continued
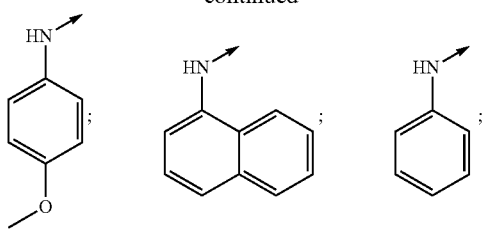
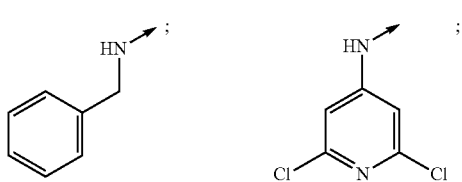
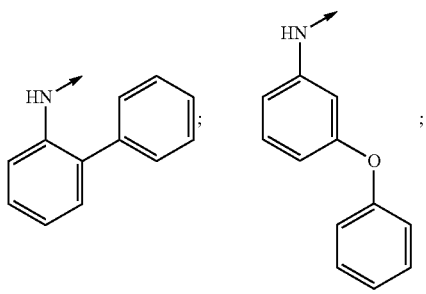
and wherein if X is NH and Y is C(O); then Z is
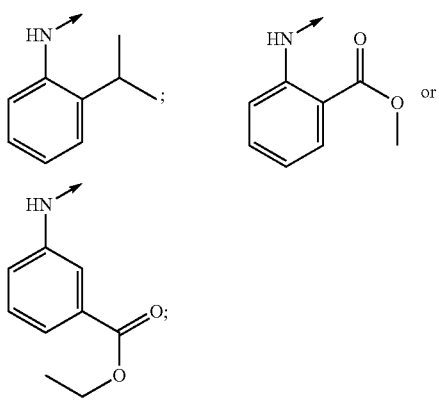
and wherein if X is NH and Y is C(O); then Z is
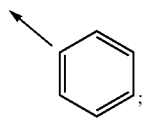;
and wherein if X is NH and Y is $S(O)_2$; then Z is
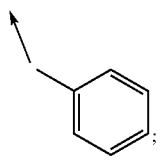;
and wherein if X is NH and Y is $CH_2$; then Z is
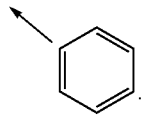.
3. The compound according to claim 1, wherein the compound has the following formula:
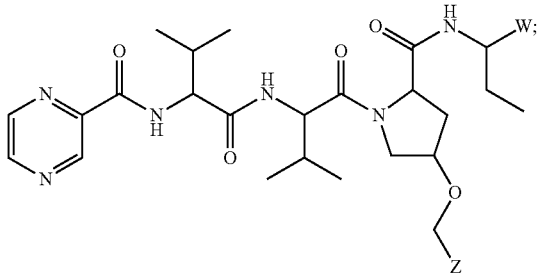
wherein if W is
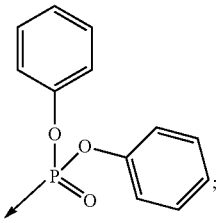
then Z is
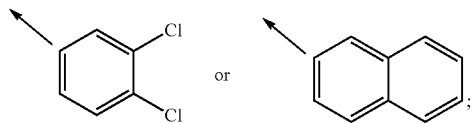

and wherein if Z is
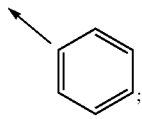
then W is
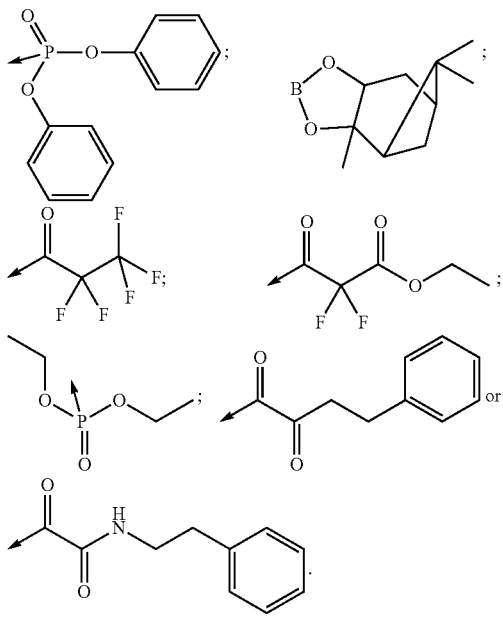
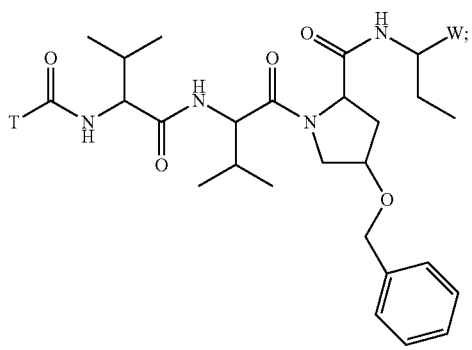
4. The compound according to claim 1, wherein the compound has the following formula:
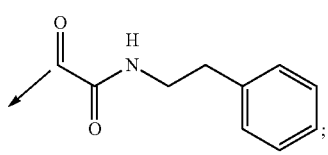
wherein if W is
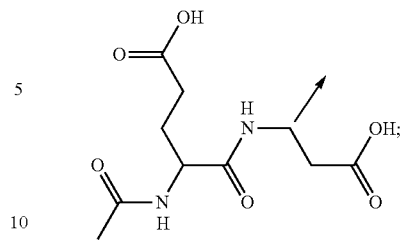... (continuing)
and wherein if W is C(O)H, then T is:
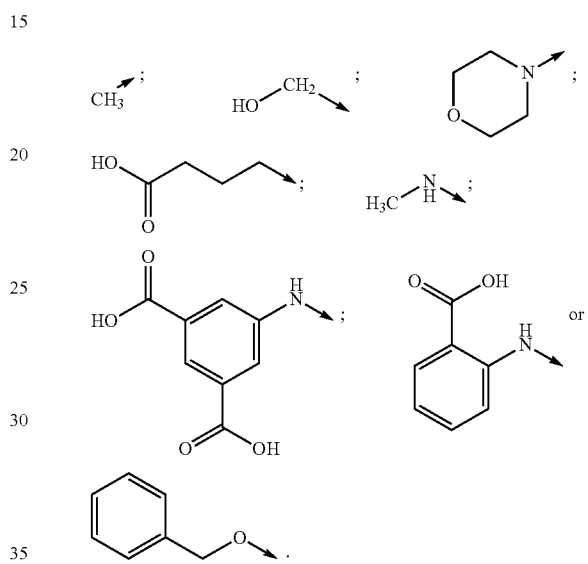
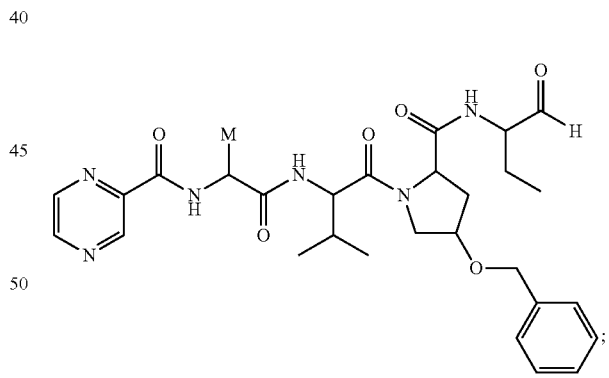
5. The compound according to claim 1, wherein the compound has the following formula:
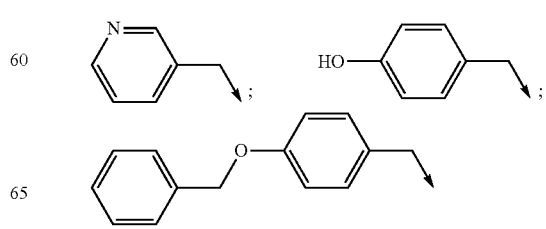
wherein M is:
then T is -continued

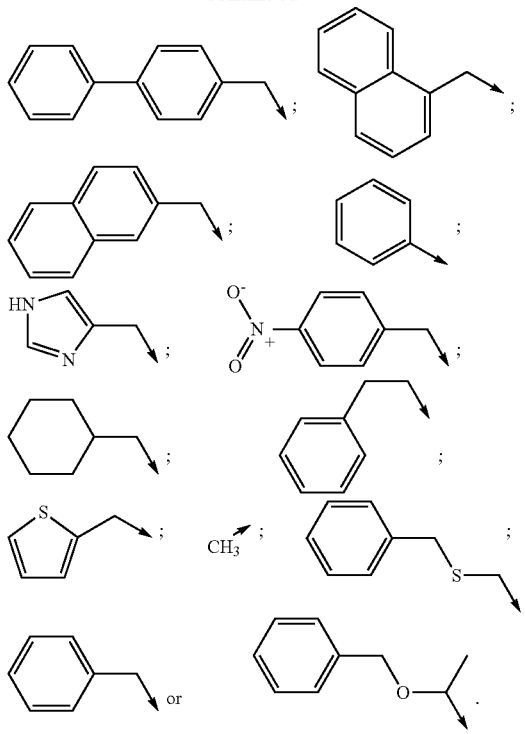

6. A compound of the formula:

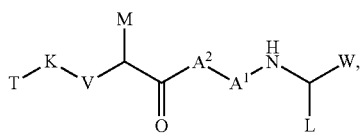

wherein
W is:

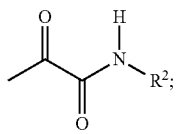

R² is cylcoalkyl;
L is alkyl;
A¹ is

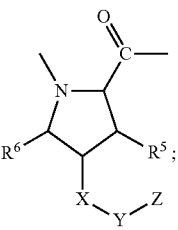

R⁵ is hydrogen;
R⁶ is hydrogen;
X is —O—;
Y is a bond;
Z is a heteroaryl substituted with a J group; wherein the J group is a halo;
A² is

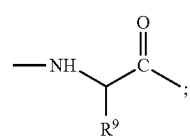

R⁹ is tert-butyl;
M is cylcoalkyl;
V is —N(R¹¹)—;
R¹¹ is hydrogen;
K is —C(O)—;
T is R¹²; and
R¹² is heteroaryl.

7. A pharmaceutically acceptable composition comprising:
a) a compound according to any of claims 1, 2, 3, 4, 5 and 6; and
b) a pharmaceutically suitable carrier.

8. A method for inhibiting serine protease activity in a patient comprising the step of administering to said patient a compound according to any one of claims 1, 2, 3, 4, 5 and 6.

9. The method according to claim 8, wherein the serine protease is HCV NS3 protease.

* * * * *

UNITED STATES PATENT AND TRADEMARK OFFICE
CERTIFICATE OF CORRECTION

PATENT NO. : 8,314,141 B2  
APPLICATION NO. : 12/031486  
DATED : November 20, 2012  
INVENTOR(S) : Tung et al.

Page 1 of 1

It is certified that error appears in the above-identified patent and that said Letters Patent is hereby corrected as shown below:

In the Claims:

In Claim 2, column 135, line 30, the structure 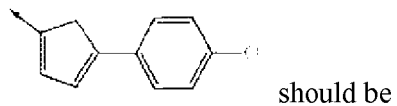 should be replaced with 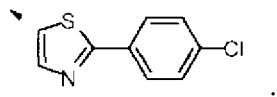 .

Signed and Sealed this  
Fourteenth Day of May, 2013

Teresa Stanek Rea  
*Acting Director of the United States Patent and Trademark Office*